United States Patent
Rajagopalan et al.

(10) Patent No.: US 10,980,590 B2
(45) Date of Patent: Apr. 20, 2021

(54) DEVICES AND METHODS FOR THE TREATMENT OF TISSUE

(71) Applicant: Fractyl Laboratories Inc., Lexington, MA (US)

(72) Inventors: Harith Rajagopalan, Wellesley Hills, MA (US); Jay Caplan, Belmont, MA (US); J. Christopher Flaherty, Auburndale, FL (US); Philip S. Levin, Storrs, CT (US)

(73) Assignee: Fractyl Laboratories, Inc., Lexington, MA (US)

( * ) Notice: Subject to any disclaimer, the term of this patent is extended or adjusted under 35 U.S.C. 154(b) by 124 days.

(21) Appl. No.: 15/917,480

(22) Filed: Mar. 9, 2018

(65) Prior Publication Data

US 2018/0193078 A1    Jul. 12, 2018

Related U.S. Application Data

(63) Continuation of application No. 13/945,138, filed on Jul. 18, 2013, which is a continuation of application No. PCT/US2012/021739, filed on Jan. 18, 2012.
(Continued)

(51) Int. Cl.
*A61B 18/00* (2006.01)
*A61N 7/02* (2006.01)
(Continued)

(52) U.S. Cl.
CPC ........ *A61B 18/00* (2013.01); *A61B 17/32002* (2013.01); *A61B 18/0206* (2013.01);
(Continued)

(58) Field of Classification Search
CPC ...... A61F 2002/041; A61F 2/04; A61F 7/123; A61M 27/008; A61M 25/10;
(Continued)

(56) References Cited

U.S. PATENT DOCUMENTS

| | | |
|---|---|---|
| 5,084,044 A | 1/1992 | Quint |
| 5,190,540 A | 3/1993 | Lee |

(Continued)

FOREIGN PATENT DOCUMENTS

| | | |
|---|---|---|
| CA | 2666661 C | 1/2015 |
| CN | 1771888 A | 5/2006 |

(Continued)

OTHER PUBLICATIONS

"Office action dated Mar. 7, 2019 for U.S. Appl. No. 13/945,138.".
(Continued)

*Primary Examiner* — Katherine M Shi
(74) *Attorney, Agent, or Firm* — Wilson Sonsini Goodrich & Rosati

(57) ABSTRACT

Systems, methods and devices for the treatment of tissue are disclosed. A system includes an elongate tube with a distal portion. A treatment element is positioned on the elongate tube distal portion, the treatment element constructed and arranged to treat target tissue. In one embodiment, gastrointestinal tissue is modified for the treatment of diabetes.

10 Claims, 18 Drawing Sheets

Related U.S. Application Data

(60) Provisional application No. 61/434,319, filed on Jan. 19, 2011, provisional application No. 61/538,601, filed on Sep. 23, 2011.

(51) Int. Cl.

| | |
|---|---|
| *A61B 17/32* | (2006.01) |
| *A61B 18/14* | (2006.01) |
| *A61B 18/02* | (2006.01) |
| *A61B 18/04* | (2006.01) |
| *A61B 18/06* | (2006.01) |
| *A61B 18/18* | (2006.01) |
| *A61B 18/20* | (2006.01) |
| *A61M 5/178* | (2006.01) |
| *A61B 90/00* | (2016.01) |
| *A61B 17/34* | (2006.01) |
| *A61B 18/24* | (2006.01) |
| *A61B 17/00* | (2006.01) |

(52) U.S. Cl.
CPC ............ *A61B 18/042* (2013.01); *A61B 18/06* (2013.01); *A61B 18/1492* (2013.01); *A61B 18/1815* (2013.01); *A61B 18/20* (2013.01); *A61M 5/178* (2013.01); *A61N 7/022* (2013.01); *A61B 17/3478* (2013.01); *A61B 18/24* (2013.01); *A61B 2017/00557* (2013.01); *A61B 2017/00818* (2013.01); *A61B 2017/32007* (2017.08); *A61B 2018/0022* (2013.01); *A61B 2018/00196* (2013.01); *A61B 2018/00208* (2013.01); *A61B 2018/00291* (2013.01); *A61B 2018/00494* (2013.01); *A61B 2018/00577* (2013.01); *A61B 2018/00601* (2013.01); *A61B 2018/00642* (2013.01); *A61B 2018/00648* (2013.01); *A61B 2018/00702* (2013.01); *A61B 2018/00821* (2013.01); *A61B 2018/00875* (2013.01); *A61B 2018/00982* (2013.01); *A61B 2018/044* (2013.01); *A61B 2018/1807* (2013.01); *A61B 2090/064* (2016.02); *A61B 2090/065* (2016.02); *A61B 2090/3614* (2016.02); *A61B 2218/002* (2013.01); *A61B 2218/007* (2013.01)

(58) Field of Classification Search
CPC .... A61B 2018/044; A61B 2018/00577; A61B 18/1492; A61B 2018/0022; A61B 18/02; A61B 18/04; A61B 2018/0212; A61B 2018/00791; A61B 2018/00214; A61B 2018/046; A61B 2018/0262; A61B 2018/00041; A61B 2017/320069; A61B 2018/00011; A61B 17/00234; A61B 201/00994; A61B 2018/00488; A61B 2018/00702; A61B 17/32; A61B 2018/00642; A61B 2018/00821; A61B 2018/00482; A61B 2018/00494; A61B 2018/00553
USPC .................. 607/40, 133; 623/23.7, 23.64
See application file for complete search history.

(56) References Cited

U.S. PATENT DOCUMENTS

| | | |
|---|---|---|
| 5,423,754 A | 6/1995 | Cornelius et al. |
| 5,471,982 A | 12/1995 | Edwards et al. |
| 5,496,311 A | 3/1996 | Abele et al. |
| 5,515,100 A | 5/1996 | Nogo |
| 5,542,928 A | 8/1996 | Evans et al. |
| 5,549,559 A | 8/1996 | Eshel |
| 5,575,772 A | 11/1996 | Lennox |
| 5,704,934 A | 1/1998 | Neuwirth et al. |
| 5,730,719 A | 3/1998 | Edwards |
| 5,800,484 A | 9/1998 | Gough et al. |
| 5,827,269 A | 10/1998 | Saadat |
| 5,859,037 A | 1/1999 | Whitcomb et al. |
| 5,869,037 A | 2/1999 | Crystal et al. |
| 5,871,525 A | 2/1999 | Edwards et al. |
| 5,879,347 A | 3/1999 | Saadat |
| 5,957,962 A | 9/1999 | Wallsten et al. |
| 5,964,753 A | 10/1999 | Edwards |
| 6,009,877 A | 1/2000 | Edwards |
| 6,053,937 A | 4/2000 | Edwards et al. |
| 6,056,744 A | 5/2000 | Edwards |
| 6,066,132 A | 5/2000 | Chen et al. |
| 6,077,257 A | 6/2000 | Edwards et al. |
| 6,112,123 A | 8/2000 | Kelleher et al. |
| 6,293,909 B1 | 9/2001 | Chu et al. |
| 6,325,777 B1 | 12/2001 | Zadno-Azizi et al. |
| 6,325,798 B1 | 12/2001 | Edwards et al. |
| 6,338,726 B1 | 1/2002 | Edwards et al. |
| 6,358,245 B1 | 3/2002 | Edwards et al. |
| 6,402,744 B2 | 6/2002 | Edwards et al. |
| 6,405,732 B1 | 6/2002 | Edwards et al. |
| 6,409,723 B1 | 6/2002 | Edwards |
| 6,425,887 B1 | 7/2002 | McGuckin et al. |
| 6,443,947 B1 | 9/2002 | Marko et al. |
| 6,544,226 B1 | 4/2003 | Gaiser et al. |
| 6,673,070 B2 | 1/2004 | Edwards et al. |
| 6,712,814 B2 | 3/2004 | Edwards et al. |
| 6,802,841 B2 | 10/2004 | Utley et al. |
| 6,905,496 B1 | 6/2005 | Ellman et al. |
| 6,962,587 B2 | 11/2005 | Johnson et al. |
| 6,974,456 B2 | 12/2005 | Edwards et al. |
| 7,077,841 B2 | 7/2006 | Gaiser et al. |
| 7,111,627 B2 | 9/2006 | Stack et al. |
| 7,122,031 B2 | 10/2006 | Edwards et al. |
| 7,125,407 B2 | 10/2006 | Edwards et al. |
| 7,156,860 B2 | 1/2007 | Wallsten |
| 7,165,551 B2 | 1/2007 | Edwards et al. |
| 7,241,295 B2 | 7/2007 | Maguire |
| 7,326,207 B2 | 2/2008 | Edwards |
| 7,371,215 B2 | 5/2008 | Colliou et al. |
| 7,387,626 B2 | 6/2008 | Edwards et al. |
| 7,422,587 B2 | 9/2008 | Bek et al. |
| 7,507,234 B2 | 3/2009 | Utley et al. |
| 7,507,238 B2 | 3/2009 | Utley et al. |
| 7,530,979 B2 | 5/2009 | Ganz et al. |
| 7,556,628 B2 | 7/2009 | Utley et al. |
| 7,585,296 B2 | 9/2009 | Edward et al. |
| 7,632,268 B2 | 12/2009 | Utley et al. |
| 7,632,291 B2 | 12/2009 | Stephens et al. |
| 7,648,500 B2 | 1/2010 | Edwards et al. |
| 7,758,623 B2 | 7/2010 | Dzeng et al. |
| 7,762,977 B2 | 7/2010 | Porter et al. |
| 7,947,038 B2 | 5/2011 | Edwards |
| 7,959,627 B2 | 6/2011 | Utley et al. |
| 7,993,336 B2 | 8/2011 | Jackson et al. |
| 7,997,278 B2 | 8/2011 | Utley et al. |
| 8,012,149 B2 | 9/2011 | Jackson et al. |
| 8,066,689 B2 | 11/2011 | Mitelberg et al. |
| 8,152,803 B2 | 4/2012 | Edwards et al. |
| 8,177,853 B2 | 5/2012 | Stack et al. |
| 8,192,426 B2 | 6/2012 | Stern et al. |
| 8,251,992 B2 | 8/2012 | Utley et al. |
| 8,273,012 B2 | 9/2012 | Wallace et al. |
| 8,323,229 B2 | 12/2012 | Shin et al. |
| 8,364,237 B2 | 1/2013 | Stone et al. |
| 8,377,055 B2 | 2/2013 | Jackson et al. |
| 8,641,711 B2 | 2/2014 | Kelly et al. |
| 8,740,894 B2 | 6/2014 | Edwards |
| 8,790,705 B2 | 7/2014 | Geigle et al. |
| 9,364,283 B2 | 6/2016 | Utley et al. |
| 9,555,020 B2 | 1/2017 | Pasricha et al. |
| 9,615,880 B2 | 4/2017 | Gittard et al. |
| 9,757,535 B2 | 9/2017 | Rajagopalan et al. |
| 9,844,641 B2 | 12/2017 | Rajagopalan et al. |
| 10,610,663 B2 | 4/2020 | Rajagopalan et al. |
| 10,765,474 B2 | 9/2020 | Kadamus et al. |

(56) References Cited

U.S. PATENT DOCUMENTS

| | | | |
|---|---|---|---|
| 10,864,352 B2 | 12/2020 | Rajagopalan et al. | |
| 10,869,718 B2 | 12/2020 | Rajagopalan et al. | |
| 2002/0013581 A1 | 1/2002 | Edwards et al. | |
| 2002/0077594 A1 | 6/2002 | Chien et al. | |
| 2002/0115992 A1 | 8/2002 | Utley et al. | |
| 2002/0192162 A1 | 12/2002 | Green | |
| 2003/0040804 A1 | 2/2003 | Stack et al. | |
| 2003/0093072 A1 | 5/2003 | Friedman | |
| 2003/0153905 A1 | 8/2003 | Edwards et al. | |
| 2003/0233065 A1 | 12/2003 | Steward et al. | |
| 2004/0082859 A1 | 4/2004 | Schaer | |
| 2004/0087936 A1* | 5/2004 | Stern | A61B 18/1492 606/41 |
| 2004/0133256 A1 | 7/2004 | Callister | |
| 2004/0148034 A1 | 7/2004 | Kagan et al. | |
| 2004/0204768 A1 | 10/2004 | Geitz | |
| 2004/0215180 A1* | 10/2004 | Starkebaum | A61B 18/1492 606/32 |
| 2004/0215296 A1 | 10/2004 | Ganz et al. | |
| 2004/0220559 A1 | 11/2004 | Kramer et al. | |
| 2005/0096638 A1 | 5/2005 | Starkebaum et al. | |
| 2005/0154386 A1 | 7/2005 | West et al. | |
| 2005/0165437 A1 | 7/2005 | Takimoto | |
| 2005/0171524 A1 | 8/2005 | Stern et al. | |
| 2005/0192652 A1* | 9/2005 | Cioanta | A61F 7/12 607/105 |
| 2005/0203489 A1 | 9/2005 | Saadat et al. | |
| 2005/0222558 A1 | 10/2005 | Baxter et al. | |
| 2005/0245943 A1 | 11/2005 | Zvuloni et al. | |
| 2005/0251116 A1 | 11/2005 | Steinke et al. | |
| 2005/0273090 A1 | 12/2005 | Nieman et al. | |
| 2006/0070631 A1 | 4/2006 | Scopton et al. | |
| 2006/0118127 A1* | 6/2006 | Chinn | A61B 18/04 128/898 |
| 2006/0135963 A1 | 6/2006 | Kick et al. | |
| 2006/0155261 A1 | 7/2006 | Bek et al. | |
| 2006/0205992 A1 | 9/2006 | Lubock et al. | |
| 2006/0247683 A1 | 11/2006 | Danek et al. | |
| 2006/0259030 A1 | 11/2006 | Utley et al. | |
| 2006/0293742 A1 | 12/2006 | Dann et al. | |
| 2007/0016262 A1 | 1/2007 | Gross et al. | |
| 2007/0032788 A1 | 2/2007 | Edwards et al. | |
| 2007/0100355 A1 | 5/2007 | Bonde et al. | |
| 2008/0045785 A1 | 2/2008 | Oyatsu | |
| 2008/0107744 A1 | 5/2008 | Chu | |
| 2008/0119788 A1 | 5/2008 | Winter | |
| 2008/0125760 A1 | 5/2008 | Gilboa | |
| 2008/0125803 A1 | 5/2008 | Sadamasa et al. | |
| 2008/0147056 A1 | 6/2008 | Van Der Weide et al. | |
| 2008/0207994 A1 | 8/2008 | Gonon | |
| 2008/0243112 A1 | 10/2008 | De Neve | |
| 2008/0275445 A1 | 11/2008 | Kelly et al. | |
| 2008/0319504 A1 | 12/2008 | Loushin et al. | |
| 2009/0012469 A1* | 1/2009 | Nita | A61B 17/22012 604/104 |
| 2009/0012512 A1* | 1/2009 | Utley | A61B 18/0218 606/21 |
| 2009/0012518 A1 | 1/2009 | Utley et al. | |
| 2009/0018533 A1 | 1/2009 | Perkins et al. | |
| 2009/0018604 A1 | 1/2009 | Mitelberg et al. | |
| 2009/0048593 A1 | 2/2009 | Ganz et al. | |
| 2009/0069805 A1 | 3/2009 | Fischer et al. | |
| 2009/0270851 A1 | 10/2009 | Babkin et al. | |
| 2010/0022891 A1 | 1/2010 | Zuluaga et al. | |
| 2010/0030190 A1 | 2/2010 | Singh | |
| 2010/0114087 A1 | 5/2010 | Edwards et al. | |
| 2010/0114325 A1 | 5/2010 | Yang et al. | |
| 2010/0168561 A1 | 7/2010 | Anderson | |
| 2010/0168624 A1 | 7/2010 | Sliwa | |
| 2010/0204673 A1 | 8/2010 | Miller | |
| 2010/0204688 A1 | 8/2010 | Hoey et al. | |
| 2010/0217151 A1 | 8/2010 | Gostout et al. | |
| 2010/0234840 A1 | 9/2010 | Jackson et al. | |
| 2010/0256775 A1 | 10/2010 | Belhe et al. | |
| 2010/0260703 A1 | 10/2010 | Yankelson et al. | |
| 2011/0046537 A1 | 2/2011 | Errico et al. | |
| 2011/0091564 A1 | 4/2011 | Chu | |
| 2011/0106273 A1 | 5/2011 | Belhe et al. | |
| 2011/0160648 A1 | 6/2011 | Hoey | |
| 2011/0172659 A1 | 7/2011 | Brannan | |
| 2011/0184401 A1 | 7/2011 | Iwata et al. | |
| 2011/0319809 A1 | 12/2011 | Smith | |
| 2012/0004654 A1 | 1/2012 | Jackson et al. | |
| 2012/0016364 A1 | 1/2012 | Mayse et al. | |
| 2012/0059364 A1 | 3/2012 | Baust et al. | |
| 2012/0197245 A1 | 8/2012 | Burnett et al. | |
| 2012/0271277 A1 | 10/2012 | Fischell et al. | |
| 2012/0271301 A1* | 10/2012 | Fischell | A61B 18/1492 606/41 |
| 2012/0289952 A1 | 11/2012 | Utley et al. | |
| 2013/0071466 A1 | 3/2013 | Chancellor et al. | |
| 2013/0178910 A1 | 7/2013 | Azamian et al. | |
| 2013/0345670 A1 | 12/2013 | Rajagopalan et al. | |
| 2014/0031773 A1 | 1/2014 | Mikkaichi | |
| 2014/0074077 A1 | 3/2014 | Lane | |
| 2014/0088529 A1 | 3/2014 | Bengtson | |
| 2014/0121646 A1 | 5/2014 | Lodin et al. | |
| 2014/0135661 A1 | 5/2014 | Garrison et al. | |
| 2014/0163664 A1 | 6/2014 | Goldsmith | |
| 2014/0187619 A1 | 7/2014 | Pasricha et al. | |
| 2014/0255458 A1 | 9/2014 | Li et al. | |
| 2014/0324037 A1 | 10/2014 | Hoey et al. | |
| 2014/0371736 A1 | 12/2014 | Levin et al. | |
| 2015/0045825 A1 | 2/2015 | Caplan et al. | |
| 2015/0141987 A1 | 5/2015 | Caplan et al. | |
| 2015/0148738 A1 | 5/2015 | Caplan et al. | |
| 2015/0359594 A1 | 12/2015 | Ben-Oren et al. | |
| 2016/0008050 A1 | 1/2016 | Rajagopalan et al. | |
| 2016/0081745 A1 | 3/2016 | Rajagopalan et al. | |
| 2016/0256663 A1 | 9/2016 | Rajagopalan et al. | |
| 2016/0310200 A1 | 10/2016 | Wang | |
| 2016/0354144 A1 | 12/2016 | Caplan et al. | |
| 2017/0007324 A1 | 1/2017 | Kadamus et al. | |
| 2017/0014596 A1 | 1/2017 | Rajagopalan et al. | |
| 2017/0191035 A1 | 7/2017 | Sia et al. | |
| 2017/0333122 A1 | 11/2017 | Rajagopalan et al. | |
| 2018/0193590 A1 | 7/2018 | Rajagopalan et al. | |
| 2018/0221622 A1 | 8/2018 | Rajagopalan et al. | |
| 2020/0001047 A1 | 1/2020 | Rajagopalan et al. | |
| 2020/0060942 A1 | 2/2020 | Rajagopalan et al. | |

FOREIGN PATENT DOCUMENTS

| | | |
|---|---|---|
| CN | 101212932 A | 7/2008 |
| EP | 1698296 A1 | 9/2006 |
| EP | 1886634 A1 | 2/2008 |
| EP | 3071286 A1 | 9/2016 |
| JP | 2002503512 A | 2/2002 |
| JP | 2003520068 A | 7/2003 |
| JP | 2004500184 A | 1/2004 |
| JP | 2004180934 A | 7/2004 |
| JP | 2006509536 A | 3/2006 |
| JP | 2006136726 A | 6/2006 |
| JP | 2007502690 A | 2/2007 |
| JP | 2008515464 A | 5/2008 |
| JP | 2010142661 A | 7/2010 |
| JP | 2010533036 A | 10/2010 |
| JP | 2011517599 A | 6/2011 |
| JP | 2013543423 A | 12/2013 |
| JP | 2014503256 A | 2/2014 |
| KR | 20080013945 A | 2/2008 |
| WO | WO-9418896 A1 | 9/1994 |
| WO | WO-9912489 A2 | 3/1999 |
| WO | WO-0207628 A2 | 1/2002 |
| WO | WO-02058577 A1 | 8/2002 |
| WO | WO-02096327 A2 | 12/2002 |
| WO | WO-02102453 A2 | 12/2002 |
| WO | WO-03033045 A2 | 4/2003 |
| WO | WO-03092609 A2 | 11/2003 |
| WO | WO-2004064600 A2 | 8/2004 |
| WO | WO-2006020370 A2 | 2/2006 |
| WO | WO-2007044244 A2 | 4/2007 |
| WO | WO-2007067919 A2 | 6/2007 |

(56) References Cited

FOREIGN PATENT DOCUMENTS

| WO | WO-2008002654 A2 | 1/2008 |
|---|---|---|
| WO | WO-2010042461 A1 | 4/2010 |
| WO | WO-2010125570 A1 | 11/2010 |
| WO | WO-2011060301 A1 | 5/2011 |
| WO | WO-2012009486 A2 | 1/2012 |
| WO | WO-2012099974 A2 | 7/2012 |
| WO | WO-2013130655 A1 | 9/2013 |
| WO | WO-2013134541 A2 | 9/2013 |
| WO | WO-2013159066 A1 | 10/2013 |
| WO | WO-2014022436 A1 | 2/2014 |
| WO | WO-2014026055 A1 | 2/2014 |
| WO | WO-2014055997 A1 | 4/2014 |
| WO | WO-2014070136 A1 | 5/2014 |
| WO | WO-2015038973 A1 | 3/2015 |
| WO | WO-2015077571 A1 | 5/2015 |
| WO | WO-2015148541 A1 | 10/2015 |
| WO | WO-2016011269 A1 | 1/2016 |
| WO | WO-2017004432 A1 | 1/2017 |
| WO | WO-2018089773 A1 | 5/2018 |
| WO | WO-2019018362 A1 | 1/2019 |
| WO | WO-2019136240 A1 | 7/2019 |

OTHER PUBLICATIONS

Final Office action dated Mar. 22, 2019 for U.S. Appl. No. 14/917,243.
Final Office action dated Apr. 5, 2019 for U.S. Appl. No. 14/609,334.
Final Office action dated Jun. 17, 2019 for U.S. Appl. No. 14/609,332.
Final Office action dated Jul. 10, 2019 for U.S. Appl. No. 15/274,948.
Office action dated Mar. 7, 2019 for U.S. Appl. No. 14/673,565.
Office action dated May 16, 2019 for U.S. Appl. No. 14/515,324.
Office action dated Jun. 6, 2019 for U.S. Appl. No. 15/683,713.
Tolman, et al. Spectrum of liver disease in type 2 diabetes and management of patients with diabetes and liver disease. Diabetes care 30.3 (2007): 734-743.
U.S. Appl. No. 15/274,948 Office Action dated Nov. 20, 2018.
U.S. Appl. No. 15/406,572 Office Action dated Feb. 7, 2019.
"Office action dated Oct. 4, 2018 for U.S. Appl. No. 14/515,324.".
"Office action dated Nov. 2, 2018 for U.S. Appl. No. 14/609,334".
Adams, et al. Theoretical design and evaluation of endoluminal ultrasound applicators for thermal therapy of pancreatic cancer under image guidance. AIP Conference Proceedings 1821, 110002 (2017); doi: http://dx.doi.org/10.1063/1.4977640.
Chathadi, et al. The role of endoscopy in ampullary and duodenal adenomas. Gastrointest Endosc. Nov. 2015;82(5):773-81. doi: 10.1016/j.gie.2015.06.027. Epub Aug. 7, 2015.
Cherrington, et al. Hydrothermal Duodenal Mucosal Resurfacing: Role in the Treatment of Metabolic Disease. Gastrointest Endosc Clin N Am. Apr. 2017;27(2):299-311. doi: 10.1016/j.giec.2016.12.002.
European search report and search opinion dated Mar. 8, 2016 for EP Application No. 13825257.2.
European search report and search opinion dated Mar. 17, 2016 for EP Application No. 13827149.9.
European search report and search opinion dated Aug. 4, 2015 for EP Application No. 13755156.0.
European Search Report and Search Opinion dated Aug. 7, 2017 for European Patent Application No. EP14864511.2.
European Search Report and Search Opinion dated Aug. 7, 2017 for European Patent Application No. EP15768945.6.
European search report and search opinion dated Nov. 25, 2015 for EP Application No. 13777572.2.
European search report with written opinion dated Feb. 1, 2018 for EP Application No. 15822378.
European search report with written opinion dated Dec. 2, 2016 for EP Application No. 14807116.
Galvao Neto, et al. Endoscopic Duodenal Mucosal Resurfacing Improves Glycemic and Hepatic Parameters in Patients With Type 2 Diabetes: Data From a First-in-Human Study. Gastroenterology. 829. Apr. 2016, vol. 150, Issue 4, Supplement 1, p. S174. 1 page. DOI: http://dx.doi.org/10.1016/S0016-5085(16)30672-2.

International search report and written opinion dated Feb. 20, 2015 for PCT Application No. US2014/711601.
International search report and written opinion dated Jun. 21, 2013 for PCT Application No. US2013/028082.
International search report and written opinion dated Jun. 26, 2015 for PCT Application No. US2015/022293.
International search report and written opinion dated Jul. 13, 2012 for PCT Application No. US2012/021739.
International search report and written opinion dated Aug. 8, 2013 for PCT Application No. US2013/037485.
International Search Report and Written Opinion dated Sep. 22, 2016 for International PCT Patent Application No. PCT/US2016/040512.
"International search report and written opinion dated Oct. 23, 2015 for PCT/US2015/040775.".
International search report and written opinion dated Nov. 8, 2013 for PCT Application No. US2013/052786.
International search report and written opinion dated Nov. 11, 2013 for PCT Application No. US2013/054219.
International search report and written opinion dated Dec. 24, 2014 for PCT Application No. US2014/055514.
International search report and written opinion dated Dec. 30, 2013 for PCT Application No. US2013/063753.
International search report dated Dec. 3, 2014 for PCT Application No. US2014/040957.
International search report with written opinion dated Jan. 9, 2018 for PCT/US2017/061074.
Miyawaki, et al. Inhibition of gastric inhibitory polypeptide signaling prevents obesity. Nat Med. Jul. 2002;8(7):738-42. Epub Jun. 17, 2002.
Notice of Allowance dated Jul. 7, 2017 for U.S. Appl. No. 15/274,764.
Notice of Allowance dated Sep. 14, 2017 for U.S. Appl. No. 15/274,809.
"Office Action date Jul. 11, 2018 for U.S. Appl. No. 14/917,243.".
"Office Action date Aug. 9, 2018 for U.S. Appl. No. 14/673,565.".
Office action dated Jan. 8, 2018 for U.S. Appl. No. 14/609,334.
Office Action dated Jan. 13, 2017 for U.S. Appl. No. 14/609,332.
Office action dated Feb. 29, 2016 for U.S. Appl. No. 14/609,334.
Office Action dated Mar. 7, 2017 for U.S. Appl. No. 15/274,764.
Office Action dated Mar. 7, 2017 for U.S. Appl. No. 15/274,809.
Office action dated Mar. 12, 2015 for U.S. Appl. No. 13/945,138.
Office action dated Mar. 19, 2018 for U.S. Appl. No. 14/470,503.
Office Action dated Mar. 23, 2017 for U.S. Appl. No. 13/945,138.
Office action dated Mar. 28, 2016 for U.S. Appl. No. 14/673,565.
Office action dated Apr. 4, 2018 for U.S. Appl. No. 15/156,585.
Office action dated May 18, 2018 for U.S. Appl. No. 14/956,710.
Office Action dated May 31, 2017 for U.S. Appl. No. 15/274,764.
Office Action dated Jun. 21, 2017 for U.S. Appl. No. 14/515,324.
Office Action dated Jun. 21, 2017 for U.S. Appl. No. 14/609,334.
Office Action dated Jun. 30, 2017 for U.S. Appl. No. 14/470,503.
Office action dated Aug. 5, 2015 for U.S. Appl. No. 13/945,138.
"Office action dated Sep. 7, 2018 for U.S. Appl. No. 14/609,332.".
Office Action dated Sep. 23, 2016 for U.S. Appl. No. 14/515,324.
Office Action dated Oct. 7, 2016 for U.S. Appl. No. 13/945,138.
Office Action dated Nov. 2, 2017 for U.S. Appl. No. 15/156,585.
Office Action dated Nov. 15, 2016 for U.S. Appl. No. 14/609,334.
Office action dated Nov. 16, 2017 for U.S. Appl. No. 14/609,332.
Office action dated Nov. 30, 2015 for U.S. Appl. No. 13/945,138.
Office action dated Nov. 30, 2017 for U.S. Appl. No. 14/673,565.
Office action dated Dec. 17, 2015 for U.S. Appl. No. 14/515,324.
Office action dated Dec. 18, 2017 for U.S. Appl. No. 14/515,324.
Office action dated Dec. 19, 2017 for U.S. Appl. No. 13/945,138.
Rajagopalan, et al. Endoscopic Duodenal Mucosal Resurfacing for the Treatment of Type 2 Diabetes: 6-Month Interim Analysis From the First-in-Human Proof-of-Concept Study. Diabetes Care Dec. 2016; 39(12): 2254-2261. https://doi.org/10.2337/dc16-0383.
Rubino, et al. Potential of surgery for curing type 2 diabetes mellitus. Ann Surg. Nov. 2002;236(5):554-9.
Sarriá, et al. Morphometric study of the layers of the canine small intestine at five sampling sites. Vet J. Jun. 2012;192(3):498-502. doi: 10.1016/j.tvjl.2011.06.041. Epub Nov. 3, 2011.
Tomizawa, et al. Clinical Outcome of Endoscopic Mucosal Resection (EMR) of Sporadic, Non-Ampullary Duodenal Adenoma

(56) References Cited

OTHER PUBLICATIONS (SNADA): Predictor Analysis of Safety and Efficacy From a High Volume U.S. Tertiary Referral Center. Gastrointestinal Endoscopy. 377. May 2017, vol. 85, Issue 5, Supplement, p. AB72. DOI: http://dx.doi.org/10.1016/j.gie.2017.03.089.
Van Baar, et al. Single Catheter for Duodenal Mucosal Resurfacing Demonstrates Similar Safety Profile with Improved Procedure Time when Compared to Original Dual Catheter: Multicenter Study of Subjects with Type 2 Diabetes. Gastroenterology. Apr. 2017vol. 152, Issue 5, Supplement 1, p. S825. DOI: http://dx.doi.org/10.1016/S0016-5085(17)32851-2.
"Office action dated Dec. 18, 2018 for U.S. Appl. No. 14/470,503.".
Co-pending U.S. Appl. No. 16/798,117, filed Feb. 21, 2020 by Rajagopalan, et al.
Co-pending U.S. Appl. No. 16/900,563, filed Jun. 12, 2020 by Kadamus, et al.
Co-pending U.S. Appl. No. 16/905,274, filed Jun. 18, 2020 by Rajagopalan, et al.
PCT/US2018/042438 International Search Report dated Sep. 14, 2018.
U.S. Appl. No. 14/917,243 Office Action dated Jun. 5, 2020.
U.S. Appl. No. 14/673,565 Office Action dated Jun. 12, 2020.
U.S. Appl. No. 15/274,948 Notice of Allowance dated May 14, 2020.
U.S. Appl. No. 15/406,572 Office Action dated Apr. 14, 2020.
U.S. Appl. No. 14/515,324 Office Action dated Mar. 31, 2020.
EP20150391.9 The Extended European Search Report dated Aug. 20, 2020.
U.S. Appl. No. 16/267,771 Notice of Allowance dated Aug. 10, 2020.
Co-pending U.S. Appl. No. 17/021,798, filed Sep. 15, 2020 by Rajagopalan; Harith et al.
EP20159816.6 The Extended European Search Report dated Aug. 17, 2020.
Co-pending U.S. Appl. No. 16/379,554, filed Apr. 9, 2019.
Co-pending U.S. Appl. No. 16/438,362, filed Jun. 11, 2019.
Co-pending U.S. Appl. No. 16/711,236, filed Dec. 11, 2019.
Co-pending U.S. Appl. No. 16/742,645, filed Jan. 14, 2020.
EP12736438.8 The Extended European Search Report dated Nov. 22, 2016.
EP14844285.8 The Extended European Search Report dated Apr. 25, 2017.
Grikscheit, et al. Tissue-engineered small intestine improves recovery after massive small bowel resection. Ann Surg., 2004, 240:748-754.
PCT/US14/66829 International Search Report dated Feb. 20, 2015.
PCT/US2019/012338 International Search Report dated Apr. 15, 2019.
Semkova, et al. Autologous transplantation of genetically modified iris pigment epithelial cells: A promising concept for the treatment of age-related macular degeneration and other disorders of the eye. Proc Natl Acad Sci U S A. Oct. 1, 2002; 99(20): 13090-13095.
Sen, et al. Autologous transplantation of endothelial progenitor cells genetically modified by adeno-associated viral vector delivering insulin-like growth factor-1 gene after myocardial infarction. Hum Gene Ther. Oct. 2010;21(10):1327-34..
U.S. Appl. No. 15/406,572 Office Action dated Nov. 15, 2019.
U.S. Appl. No. 13/945,138 Office Action dated Dec. 10, 2019.
U.S. Appl. No. 14/470,503 Notice of Allowance dated Feb. 27, 2019.
U.S. Appl. No. 14/609,334 Office Action dated Jan. 8, 2020.
U.S. Appl. No. 14/956,710 Notice of Allowance dated Jan. 9, 2019.
U.S. Appl. No. 15/683,713 Notice of Allowance dated Nov. 27, 2019.
U.S. Appl. No. 15/683,713 Office Action dated Oct. 10, 2019.
U.S. Appl. No. 16/267,771 Office Action dated Feb. 6, 2020.
U.S. Appl. No. 15/683,713 Notice of Allowance dated Mar. 10, 2020.
Co-pending U.S. Appl. No. 17/095,108, inventors Rajagopalan; Harith et al., filed Nov. 11, 2020.
Co-pending U.S. Appl. No. 17/096,855, inventors Rajagopalan; Harith et al., filed Nov. 12, 2020.
Co-pending U.S. Appl. No. 17/110,720, inventors J.; Kadamus Christopher J. et al., filed Dec. 3, 2020.
U.S. Appl. No. 13/945,138 Notice of Allowance dated Dec. 22, 2020.
U.S. Appl. No. 14/515,324 Office Action dated Dec. 4, 2020.
U.S. Appl. No. 14/609,334 Notice of Allowance dated Dec. 10, 2020.
U.S. Appl. No. 14/609,334 Office Action dated Oct. 29, 2020.
U.S. Appl. No. 15/406,572 Notice of Allowance dated Oct. 28, 2020.
U.S. Appl. No. 16/711,236 Office Action dated Dec. 10, 2020.
U.S. Appl. No. 16/900,563 Notice of Allowance dated Dec. 17, 2020.
U.S. Appl. No. 16/900,563 Office Action dated Nov. 9, 2020.
U.S. Appl. No. 14/673,565 Office Action dated Dec. 24, 2020.

\* cited by examiner

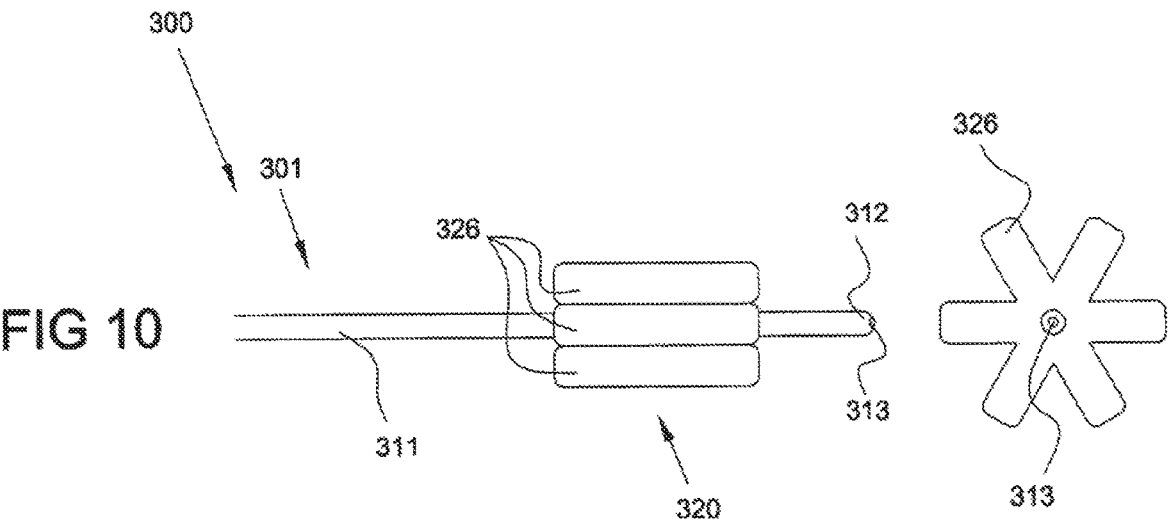
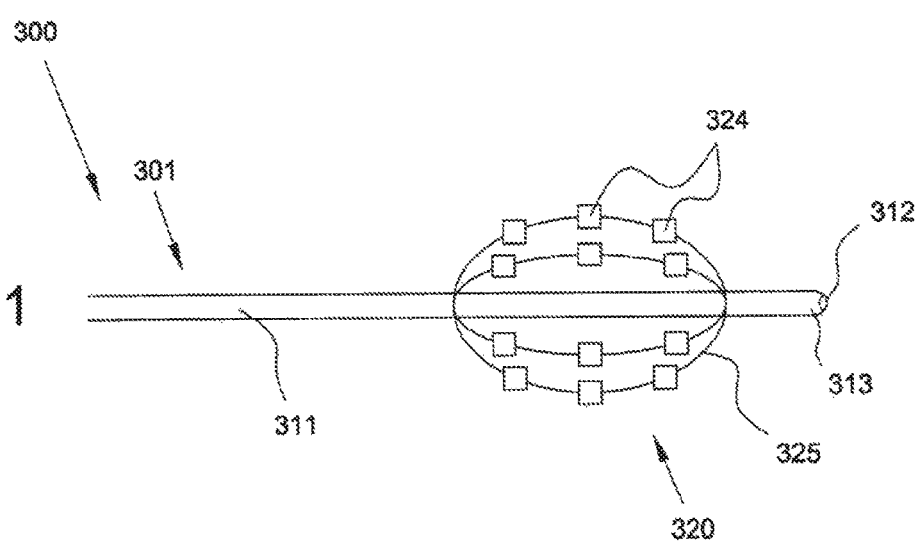

DEVICES AND METHODS FOR THE TREATMENT OF TISSUE

RELATED APPLICATIONS

This application is a continuation of U.S. patent application Ser. No. 13/945,138, filed Jul. 18, 2013, which is a continuation of PCT Application No. PCT/US2012/021739, filed Jan. 18, 2012, which claims the benefit of prior U.S. Provisional Application 61/434,319, entitled Method and System for Treatment of Diabetes, filed Jan. 19, 2011, the entire content of which is incorporated herein by reference in its entirety and prior U.S. Provisional Application 61/538,601, entitled Devices and Methods for the Treatment of Tissue, filed Sep. 23, 2011, the entire content of which is incorporated herein by reference in its entirety.

TECHNICAL FIELD

The embodiments disclosed herein relate generally to systems, devices and methods for treating tissue, particularly gastrointestinal tissue. Methods of treating diabetes are also disclosed.

BACKGROUND

Diabetes is a metabolic disease in which a person develops high blood sugar because the person's body does not produce enough insulin or the cells of the body are incapable of effectively responding to the produced insulin. Primarily, diabetes is of two types: Type-1 and Type-2. Type-1 diabetes results due to the body's failure to produce enough insulin, and Type-2 diabetes results from the body's autoimmune destruction of pancreatic beta cells and, consequently, the body's failure to produce enough insulin, and Type 2 diabetes is a complex metabolic derangement that causes hyperglycemia through insulin resistance (in which the body's cells fail to properly utilize the produced insulin) and inadequate insulin production to meet the body's needs.

Currently, there are several procedures aimed at treating diabetes based on the above concept. The procedures require major surgery, removal of portions of the GI tract, and/or long-term implants. As with any major surgery, gastric bypass surgery carries a risk of complications.

Devices have been developed to deliver energy to the body. For example, cardiac ablation devices have been designed to deliver ablative energy to coronary tissue. Additionally, urethral resection devices have been designed to burn or cut away portions of a prostate. Each of these technologies has been modified and adapted toward effective usage in the particular portion of the body to be treated as well as the particular disease to be treated.

There is a need for systems and methods that can provide a therapeutic treatment of the GI tract by the application of energy to the GI tract. Specifically, there is a need to provide a treatment of diabetes with a procedure in the GI tract that is less invasive than gastric bypass surgery and has other advantages for patients.

SUMMARY

The systems, methods and devices of the present inventive concepts treat target tissue of a patient, such as to provide a therapy for a patient disease or disorder. A system for treating diabetes in a patient comprises a viewing component, a selecting component and a treating component. The viewing component allows the duodenal mucosa to be evaluated. The selecting component selects a target area of the patient's duodenal mucosa to treat. The treating component treats a treatment area of the patient's duodenal mucosa such that the treatment leaves the patient's duodenum anatomically intact with respect to the patient's stomach and jejunum. The treatment area includes an area of the duodenal mucosa that is contiguous with an area in at least one of the patient's jejunal mucosa and gastric mucosa.

The treating component may be adapted to remove the patient's duodenal mucosa and the treatment may comprise eliminating stem cells in the duodenal mucosa.

The treating component may be adapted to ablate tissue in the duodenal mucosa.

The treating component may be adapted to ablate tissue in the duodenal mucosa and may comprise a balloon equipped with an ablative subcomponent for ablating the duodenal mucosa.

The treating component may be adapted to remove the patient's duodenal mucosa and may comprise a shaver and/or scraper for shaving and/or scraping at least a portion of the duodenal mucosa. The shaver and/or scraper may comprise a balloon equipped with a cutting device for treating the duodenal mucosa.

The system may further comprise a tissue expansion device, such as a tissue expansion device constructed and arranged to expand submucosal tissue of the duodenum.

According to another aspect of the invention, a system for treating a patient includes an elongate tube and a treatment element. The elongate tube, typically a flexible shaft, includes a distal portion, and the treatment element is positioned on the elongate tube distal portion. The treatment element is constructed and arranged to treat target tissue and to avoid adversely affecting non-target tissue. A method is provided wherein the system is provided and target tissue is treated with the treatment element.

Selection of target tissue and target tissue treatments are applicable to numerous patient diseases or disorders, including but not limited to: Diabetes; Type-1 Diabetes; Type-2 Diabetes; hypercholesterolemia; a metabolic syndrome; disease; celiac disease; obesity; cancer such as bronchoalveolar carcinoma; and cystitis. In some embodiments, no chronic implant (e.g. no implant left within the body for more than twenty four hours), is used. In other embodiments, a chronically implanted device may be included, such as a device selected from the group consisting of: a stent; a sleeve; and a drug delivery device such as a coated stent, a coated sleeve and/or an implanted pump; and combinations of these.

The treatment element is configured to target tissue in one or more locations of the patient. The target tissue comprises a three dimensional volume of tissue, and may include a first portion, a treatment portion, whose treatment has a therapeutic benefit to a patient; as well as a second portion, a safety margin portion, whose treatment has minimal or no adverse effects to the patient. Non-target tissue may be identified which is tissue whose damage or other adverse effect caused by the treatment element is reduced or avoided.

The target tissue treatment may include one or more effects to the target tissue such as an effect selected from the group consisting of: modification of cellular function; cell death; apoptosis; instant cell death; cell necrosis; denaturing of cells; removal of cells; and combinations of these. Target tissue may be selected such that after treatment the treated target tissue and/or tissue that replaces the target tissue functions differently than the pre-treated target tissue. The treatment of target tissue may initiate an inflammatory response. The treatment of target tissue may cause target tissue cells to become non-functional and/or prevent cellular secretions. The treatment of target tissue may alter cellular autocrine and/or paracrine signaling. The modified and/or replacement tissue may have different secretions or quantities of secretions than the pre-treated target tissue, such as to treat diabetes or obesity. The modified and/or replacement tissue may have different absorptive properties than the target tissue, such as to treat diabetes; obesity and/or hypercholesterolemia. The new tissue may comprise different cholesterol absorption properties. The effect of the treatment may occur acutely, such as within twenty four hours, or after longer periods of time such as greater than twenty four hours or greater than one week.

Target tissue to be treated may comprise two or more tissue portions, such as a first tissue portion treated with a first treatment and/or a first treatment element, and a second tissue portion treated with a second treatment and/or second treatment element. The first and second tissue portions may overlap and they may be adjacent, such as comprising two adjacent partial circumferential portions of tissue. The first and second treatment and/or treatment elements may be similar or dissimilar. Dissimilarities may include type and/or amount of energy to be delivered by an energy delivery treatment element. Other dissimilarities may include but are not limited to: target tissue area treated; target tissue depth treated; target tissue circumferential portion treated; energy delivery type; and energy delivery rate and/or amount. The system may be constructed and arranged to sequentially treat a first target tissue portion and a second target tissue portion. The first and second target tissue portions may include similar or dissimilar tissue characteristics. Similar or dissimilar tissue characteristics may be selected from the group consisting of: tissue type such as tissue layer type; tissue density; tissue thickness; and combinations of these. The first target tissue portion may be treated in a similar or dissimilar manner than the treatment of the second tissue portion. Dissimilarities between a first treatment and a second treatment may be selected from the group consisting of: energy level; delivery duration; tissue temperature during delivery and combinations of these. The first tissue portion may be thinner than the second tissue portion, and the system may be configured to treat the first tissue portion at a lower temperature than the second tissue portion, at a lower energy level than the second tissue portion, and/or for a shorter treatment duration than the second tissue portion.

Target tissue may include tissue of the duodenum, such as tissue including all or a portion of the mucosal layer of the duodenum, such as to treat diabetes or obesity while leaving the duodenum anatomically connected. Replacement tissue may comprise cells that have migrated from one or more of gastric mucosa; jejunal mucosa; or an untreated portion of the duodenum whose mucosal tissue functions differently than the treated mucosal tissue functions prior to treatment. In some embodiments, target tissue includes treatment tissue comprising the mucosal layer of the duodenum, and safety margin tissue comprising a full or partial layer of the submucosal layer of the duodenum. In some embodiments, the target tissue comprises the entire length of the mucosal layer of the duodenum, and may include a portion of the pylorus contiguous with the duodenal mucosa and/or a portion of the jejunum contiguous with the duodenal mucosa. Treatment of duodenal tissue may be performed to treat a disease or disorder selected from the group consisting of: diabetes; obesity; insulin resistance; a metabolic disorder and/or disease; and combinations of these. A full circumferential portion (e.g. 360°) of the mucosal layer is typically treated. In some embodiments, the target tissue comprises at least a circumferential portion of an innermost mucosal partial layer along at least a segment of the duodenum. In these embodiments, the target tissue may comprise a tissue portion selected from the group consisting of: at least a circumferential portion of an innermost mucosal partial layer along the full length of the duodenum; a full circumferential portion of the innermost mucosal partial layer; a full circumferential portion of an innermost mucosal partial layer along the full length of the duodenum; the stem cells at the base of the crypts; the transit amplifying cells; and combinations of these. The target tissue may comprise a full circumferential portion of an innermost mucosal partial layer along the full length of the duodenum. The target tissue may comprise at least a portion of the submucosal layer of the duodenum. In these embodiments, the target tissue may comprise tissue selected from the group consisting of: at least a circumferential portion of an innermost submucosal partial layer along at least a segment of the duodenum; at least a circumferential portion of the innermost submucosal partial layer along the full length of the duodenum; a full circumferential portion of the innermost submucosal partial layer; a full circumferential portion of the innermost submucosal partial layer along the full length of the duodenum; and combinations of these. The target tissue may comprise one or more longitudinal portions of the duodenum. The target tissue may comprise a distal portion of the stomach, such as target tissue spanning from a distal portion of the stomach to a proximal portion of the jejunum. The target tissue may comprise tissue spanning from the pylorus to the ligament of Treitz. The target tissue may comprise a partial circumferential portion of the duodenum, such as a partial circumferential portion of the duodenum proximate the Ampulla of Vater and/or a partial circumferential portion of the duodenum proximate the pancreas. The target tissue may comprise a depth of tissue such as a pre-determined depth of tissue. The tissue depth may comprise a full mucosal layer and/or a full submucosal layer. The target tissue depth may comprise a partial tissue layer, such as a partial submucosal layer depth selected from the group consisting of: one percent of the depth of the full submucosal layer; twenty five percent of the full submucosal depth; fifty percent of the full submucosal depth; and combinations of these. The target tissue may comprise a depth, a length and a width, and the depth of target tissue may be relatively uniform along the length and/or the width. Alternatively, the target tissue may comprise a depth, a length and a width, and the depth of the target tissue may vary along the length and/or the width. The target tissue may be selected based on a patient anatomical and/or physiologic condition, such as a an anatomical and or physiologic condition selected from the group consisting of: hyperglycemic hyperosmolar state; diabetic ketoacidosis; insulin resistance; pre-diabetes; hypertriglyceridemia; and combinations of these. The target tissue may be selected based on gross anatomical and/or functional borders of the target tissue, such as gross anatomical and/or functional borders selected from the group of locations consisting of: tissue between the duodenum and adjacent tissue of the gastrointestinal tract; tissue between the four parts of the duodenum; and combinations of these.

Target tissue may comprise tissue of the terminal ileum, such as to treat hypercholesterolemia or diabetes. Target tissue may extend into the proximal ileum and/or the colon.

Target tissue may comprise gastric mucosal tissue, such as regions that produce ghrelin and/or other appetite regulating hormones, such as to treat obesity or an appetite disorder.

Target tissue may comprise bladder wall tissue, such as to treat a disease or disorder selected from the group consisting of: interstitial cystitis; bladder cancer; bladder polyps; pre-cancerous lesions of the bladder; and combinations of these.

Target tissue may comprise tissue selected from the group consisting of: large and/or flat colonic polyps; margin tissue remaining after a polypectomy; and combinations of these. These tissue locations may be treated to treat residual cancer cells.

Target tissue may comprise airway lining tissue, such as to treat a disease or disorder selected from the group consisting of: bronchoalveolar carcinoma; other lung cancers; pre-cancerous lung lesions; and combinations of these.

Target tissue may comprise at least a portion of the intestinal tract afflicted with inflammatory bowel disease, such that Crohn's disease or ulcerative colitis may be treated.

Target tissue may comprise issue of the oral cavity, such as to treat one or more of: oral cancers and a pre-cancerous lesion of the oral cavity.

Target tissue may comprise tissue of the nasopharynx, such as to treat nasal polyps.

Target tissue may comprise gastrointestinal tissue selected to treat Celiac disease and/or to improve intestinal barrier function.

The treatment elements, systems, devices and methods may be constructed and arranged to avoiding treating certain tissue, termed "non-target tissue" herein. Depending on the location of treatment, different non-target tissue may be applicable. In certain embodiments, non-target tissue may comprise tissue selected from the group consisting of: the tunica serosa, the tunica muscularis and/or the outermost partial layer of the submucosa such as during mucosal treatment; Ampulla of Vater such as during mucosal treatment proximate the Ampulla of Vater; Sphincter of Oddi; pancreas; bile duct; pylorus; body organ; and combinations of these.

The treatment elements of the present inventive concepts may comprise a transducer or other functional element configured to deliver energy, such as an element selected from the group consisting of: sound delivery elements such as piezo transducers and ultrasound crystals; electromagnetic energy delivery elements such as electrodes; laser energy deliver elements such as optical fibers, prisms, lenses and other optical components; a cutting element such as a blade, a roughened surface or an abrasive mesh; and combinations of these. The treatment elements of the present inventive concepts may be advanceable and/or retractable, and may be radially expandable, radially extendable and/or radially compressible. Radially expandable elements may comprise one or more of a balloon; a cage; and radially deployable arms, such as a balloon with an abrasive element or surface, or a balloon containing one or more electrodes configured to deliver electromagnetic energy. Treatment elements may comprise three or more energy delivery elements, such as three or more energy delivery elements configured in a radially expandable array. Treatment elements may treat tissue in a radially expanded state, such as to compress tissue (e.g. during energy delivery); prevent perfusion of blood; and/or to bring a treatment element such as an energy delivering electrode into contact with tissue. Treatment elements may be configured to conform to the topography of target tissue, such as treatment elements comprising a topography conformable balloon and/or a topography conformable expandable cage. The treatment elements may be configured to perform a full circumferential tissue treatment in a single step, or partial circumferential tissue treatments in multiple steps. Treatment elements may be configured to expand to a diameter of at least 1 cm or to a diameter of at least 2 cm. Treatment elements may be constructed and arranged to cause blood proximate the target tissue to migrate away from the target tissue, such as to avoid an undesired heat sinking effect.

A second treatment element may be included in the systems, devices and methods of the present inventive concepts, such as a first treatment element mounted to a first elongate tube and a second treatment element mounted to a second elongate tube slidingly received by the first elongate tube. The first and second treatment elements may be configured to deliver different tissue treatments, such as a first treatment with a first form of energy and a second treatment with a different form of energy. The second treatment element is typically mounted to a distal portion of the first elongate shaft or a second elongate tube.

A balloon may be configured as a treatment element, such as a balloon containing fluid between 43° C. and 100° C., typically between 65° C. and 90° C. to treat the target tissue. A balloon may comprise one or more electrodes, such as one or more segmented or flexible electrodes configured to deliver electromagnetic energy (e.g. RF energy) to tissue in a monopolar mode (e.g. by passing energy between a balloon electrode and a patch or other skin electrode) and/or a bipolar mode (e.g. by passing energy between two balloon electrodes). Multiple balloons may be included, such as a balloon configured as a tissue abrader and a balloon configured for tissue ablation. In some multiple balloon embodiments, a first balloon treats tissue with hot fluid ablation and/or electromagnetic energy ablation and a second balloon is configured to abrade tissue. The second balloon may be positioned distal to or proximal to the first balloon. A treatment element may comprise a multiple lobed balloon, such as a multiple lobed balloon configured to deliver energy to target tissue via a hot fluid and/or a multiple lobed balloon including one or more energy delivery electrodes on its one or more lobes. Balloons configured as treatment elements may be expanded with a fluid such as air, $CO_2$ and/or saline.

Treatment elements of the present inventive concepts may be configured to deliver energy, such as in a continuous, pulsed, and/or variable energy delivered by an energy delivery element. In one configuration, a first energy application is delivered followed by a similar or dissimilar second energy application, to the same or different tissue portions. Energy delivery may be varied, within a single application or from a first application to a second application, such as to accommodate different target tissue thicknesses, such as different thicknesses of duodenal mucosa or duodenal submucosa. In some embodiments, electromagnetic energy is delivered in a first application and a second application. The first application may be delivered to a first layer of tissue and the second application, at a higher energy level than the first, delivered to a second, deeper layer of tissue. Energy delivery may be varied, within a single application or from a first application to a second application, such as to avoid undesired treatment to non-target tissue. Varied energy delivery may comprise varying of level of energy delivered. Pulsed energy delivery may comprise pulse width modulated energy delivery and/or time division multiplexing energy delivery.

Energy delivered may be in one or more forms, such as an energy selected from the group consisting of: electromagnetic energy such as radiofrequency and microwave energy; plasma energy such as argon plasma energy used for coagulation; sound energy such as ultrasound energy and subsonic sound energy; light energy such as laser light energy, infrared light energy and visible light energy; chemical energy; thermal energy such as heat or cryogenic energies; mechanical energy such as mechanical energy delivered by one or more cutting and/or abrading elements; and combinations of these. Energy delivered may be electromagnetic energy selected form the group consisting of: non-ionizing energy; ionizing energy; non-plasma forming energy; plasma forming energy; and combinations of these. Electromagnetic energy may be delivered to remove tissue, ablate tissue, shrink tissue, modify tissue and/or provide hemostasis. The system may include a saline delivery assembly constructed and arranged to deliver saline solution proximate the target tissue during energy delivery. Energy delivered may be laser energy, such as laser energy selected from the group consisting of: CO2 Laser; KTP Laser; Er:YSGG Laser; Er:glass; Ho:YAG Laser; Ho:YSGG laser; nd:YAG Laser; Nd:YSGG; Nd:doped Laser; Semiconductor Laser; Excimer Laser; Xenon Chloride Laser; Argon Fluoride Laser; and combinations of these. Laser energy may be delivered from a laser selected from the group consisting of: a rare earth doped crystal laser; an argon or krypton gas laser; a liquid laser such as a dye laser; and combinations of these. Chemical energy delivered may be in the form of a chemical peeling agent delivered to target tissue, such as an agent selected from the group consisting of: an acid; phenol; phenol/croton; and combinations of these. Agents may be delivered through an outlet port, such as an outlet port selected from the group consisting of: a nozzle; an opening; a membrane; and combinations of these. Delivered agents may be configured to be absorbed by one or more forms of energy, such as a chromophore configured to support photodynamic and/or ultrasonic energy delivery. The delivered agent may comprise a dye. Heat energy may be delivered to treat the target tissue, such as via a hot fluid filled balloon such as a conformal balloon. The hot fluid may be a fluid selected from the group consisting of: water; saline; glycerin; steam; and combinations of these. Heat energy may be delivered by a heating and/or heatable component such as a cage; a cutter; a wire; and combinations of these. Heat energy may be applied in a first energy delivery and a second energy delivery, such as when the first energy delivery is performed at a higher temperature than the second energy delivery. Heat energy may be delivered by magnetic particles such as particles heated by an MRI field and/or particles configured to bind to tissue such as duodenal tissue. Cryogenic energy may be delivered to treat the target tissue, such as when the system includes a cryogenic source selected from the group consisting of: CO2; argon; nitrous oxide; liquid nitrogen; and combinations of these. Mechanical energy may be delivered to tissue, such as via a mechanical abrader comprising one or more of: a balloon with a surrounding abrasive mesh; a balloon with embedded abrasives; and a mechanical abrader configured to remove tissue. Mechanical abraders may be configured to rotate and/or translate, such as via a motion assembly of the system. Target tissue may be treated by a fluid jet, such as a fluid jet constructed and arranged to deliver a fluid selected from the group consisting of: water; air; $CO_2$; steam; and combinations of these. A water jet may be configured to remove target tissue and/or to cause the target tissue to become non-functional, such as to reduce, prevent or modify cellular secretions of the target tissue. Two or more different forms of energy may be delivered, by one or more energy delivery elements. Two more different forms of energy may be delivered simultaneously and/or sequentially. Energy may be delivered with a treatment element in contact with target tissue, such as when configured as a hot liquid filled balloon or an assembly including one or more radiofrequency electrodes. Alternatively or additionally, energy may be delivered with a treatment element separated from target tissue by a gap comprising liquid or air, such as when configured as a laser delivery element or a high intensity ultrasound energy delivery element. An energy delivery conduit such as a wire or optical fiber may be configured to transmit energy to a treatment element. A gel may be included to improve transfer of energy to tissue, such as a gel positioned on or near a treatment element. The gel may comprise a gel selected from the group consisting of: a thermally conductive gel; an electrically conductive gel; an optically transmissive gel; and combinations of these. The treatment element may be constructed and arranged to deliver energy to target tissue via sonophoresis and/or iontophoresis.

A sensor may be used to measure energy delivery or other parameters, such as a sensor comprising one or more sensors constructed and arrange to provide a signal. In some embodiments, a sensor is used to treat tissue with closed loop energy delivery such as a sensor providing a signal representing: amount of energy delivered; cumulative amount of energy delivered; depth of energy penetration; depth of resultant treatment; tissue temperature; tissue physical characteristics such as color; and combinations of these. The sensor may comprise a temperature sensor and/or an impedance sensor, constructed and arranged to regulate energy delivery such as radiofrequency energy delivery. The sensor may comprise a sensor configured to provide information related to tissue thickness, such as an image sensor such as an ultrasound sensor, an OCT sensor and/or an OCDR sensor. The sensor may comprise a sensor configured to provide energy delivery information, such as depth of energy delivery information. The sensor may be mounted to the elongate tube and/or the treatment element, such as an expandable treatment element. The sensor may be positioned to contact a tissue wall, such as a duodenal tissue wall. The sensor may be positioned to penetrate or otherwise reside within a layer of tissue, such as to reside within a layer of submucosal tissue, such as during a submucosal injection procedure to measure one or more of temperature, flow rate and pressure. The system may include an Electromyographic sensor, such as when the system is constructed and arranged to deliver energy based on electromyography of the muscularis mucosa. The system may include a calorimetry sensor and/or a serum level sensor. The system may include an imaging sensor, such as when the system is constructed and arranged to quantify a change in tissue color such as villi tissue color.

The elongate tubes of the present inventive concepts may be inserted into a body lumen such or body cavity, such as a body location selected from the group consisting of: gastrointestinal tract; esophagus; stomach; pylorus; duodenum; jejunum; lung; bladder; nasopharynx; bladder; colon; airway; oral cavity; and combinations of these. The elongate tubes may further be configured for insertion into a body access device, such as an endoscope, a laparoscopic port; a transgastric access device, o a vascular introducer, such as by being front loaded o back loaded. The elongate tubes may be rotated and may have one or portions such as a distal portion deflected, such as via a pull wire connected to a control mounted on a proximal handle an insertable curved mandrel such as a mandrel constructed of shaped memory material configured to change shape as it transitions from room temperature to body temperature, and/or another deflection assembly. The deflection assembly may be configured to cause or otherwise improve contact of a treatment element with target tissue. Multiple elongate tubes may be included, such as a first elongate tube including a first treatment element, and a second elongate tube including a second treatment element. The second elongate tube may be slidingly received by the first elongate tube, or it may be placed alongside the first elongate tube.

One or more expandable elements may be included in the system and devices of the present invention, such as an expandable element mounted to an elongate tube. The expandable elements may be used to expand and make contact with tissue, such as to circumferentially contact the inner wall of a body lumen such as a portion of the gastrointestinal tract. Expandable elements may comprise an expandable balloon or cage, and one or more treatment elements may comprise the expandable element and/o be mounted to the expandable element. The expandable elements may be pressurized, such as to apply a varying force to tissue. Varied applied force may be used to vary treatment to tissue, such as to vary contact of an electrode or hot fluid balloon to tissue thus modifying amount of treatment, depth of treatment, force of treatment, impedance of an electrode with tissue, and combinations of these.

One or more numerous forms and types of sensors may be included in the systems, devices and methods of the present inventive concepts. Sensors may be mounted to an elongate tube, a treatment element and/or a radially expandable element. Sensors may include but are not limited to: heat sensors such as thermocouples; impedance sensors such as tissue impedance sensors; pressure sensors; blood sensors; optical sensors such as light sensors; sound sensors such as ultrasound sensors; electromagnetic sensors such as electromagnetic field sensors; and combinations of these. Treatment may be monitored based on one or more signals received from one or more sensors. Sensors may be positioned in, on or proximate to tissue such as target tissue. Sensors may provide patient parameter information, such as information selected from the group consisting of: temperature information such as tissue temperature information or treatment element temperature; impedance information such as tissue impedance information; pressure information; blood flow information; blood sugar levels; insulin levels; glucagon levels; GIP, GLP-1, GLP-2 and/or other gastrointestinal hormone levels; and combinations of these. The sensor may comprise an image sensor, such as an image sensor providing information about a change in tissue color. Imaging sensors can be configured to produce an image selected from the group consisting of: image tissue thickness; image tissue vascularity; image ice ball found in cryogenic energy delivery; and combinations of these. Imaging sensors may be selected from the group consisting of: X-Ray such as fluoroscopy; CT imaging; MRI; Ultrasound imaging; Molecular Imaging; Nuclear Imaging such as Nuclear imaging with or without glucose tolerance testing; OCT; Spectroscopy such as Tera-Hertz spectroscopy; and combinations of these.

One or more functional elements may be included in the systems, methods and devices of the present inventive concepts. A functional element may be mounted to an elongate tube, such as a functional element selected from the group consisting of: a sensor; a transducer; a vacuum port; a visualization element or device such as an ultrasound crystal or an optical assembly; and combinations of these. A vacuum pot may be configured to remove tissue and/or to bring at least a portion of the system into contact with tissue, such as to bring the elongate tube and/or a treatment element in contact with tissue. A system functional element may comprise a visualization device, such as a visualization device selected from the group consisting of: visible light camera; ultrasound imager; optical coherence tomography imager; and combinations of these.

A body lumen pressurization assembly may be included such as to deliver a pressurization fluid. The pressurization fluid may be delivered through a lumen, such as a lumen of an endoscope or an elongate tube. The pressurization assembly may comprise a source of pressurized fluid such as insufflation fluid comprising a liquid and/or a gas, such as a liquid and/or a gas configured to distend a body lumen such as a lumen of the gastrointestinal tract. One or more occlusive elements, such as a balloon mounted to an elongate tube, may be included to limit migration of pressurization fluid (e.g. maintain pressure in a lumen such as the duodenum). Insufflation pressures may be maintained at a pressure greater than 0.5 cm of $H_2O$ and less than 15 cm of $H_2O$. The system may include a second elongate tube configured to deliver the pressurization fluid. The second elongate tube may be constructed and arranged to be slidingly received by a body access device, such as an endoscope constructed and arranged t slidingly receive both the first elongate tube and the second elongate tube.

A body access device may be included, such as an endoscope configured to receive an elongate tube comprising a treatment element. An imaging device may be included, such as: a body inserted visualization device such as a visible light camera integral to or inserted into an endoscope, an ultrasound imager; and/or an OCT imager. Alternatively or additionally, an external visualization device may be included such as: an X-ray; a fluoroscope; an ultrasound image; an MRI; a PET Scanner; and combinations of these.

An energy delivery unit may be included, such as a unit configured to deliver one or more forms of energy. Energy may comprise closed loop energy delivery, such as closed loop delivery based on tissue temperature or tissue impedance. A controller and user interface may be included such as to enter one or more system input parameters or to view one or more system output parameters. System input parameters may include but are not limited to: type of energy to be delivered such as RF energy, thermal energy and/or mechanical energy; quantity of energy to be delivered such as a cumulative number of joules of energy to be delivered or peak amount of energy to be delivered; types and levels of combinations of energies to be delivered; energy delivery duration; pulse width modulation percentage of energy delivered; number of reciprocating motions for an abrasive device to transverse; temperature for a treatment element such as target temperature or maximum temperature; insufflation pressure; insufflation duration; and combinations of these. System input parameters may include but are not limited to a pre-procedural or peri-procedural parameter selected from the group consisting of: mucosal density and/or thickness; mucosal "lift" off of submucosa after a submucosal injection; longitudinal location of target tissue within the GI tract; and combinations of these. System output parameters may include but are not limited to: temperature information such as tissue and/or treatment element temperature information; pressure information such as balloon pressure information or insufflation pressure information; force information such as level of force applied to tissue information; patient information such as patient physiologic information recorded by one or more sensors; and combinations of these. The user may be constructed and arranged to initiate, moderate and/or cease treatment delivered by the treatment element, such as energy delivery treatment delivered by the treatment element.

A motion transfer assembly may be included, such as to rotate and/or translate the elongate tube and/or one or more treatment elements. In some embodiments, a tissue abrader is rotated and translated during tissue treatment. In some embodiments, a light energy delivery element such as a laser or ultrasound energy delivery element is rotated and/or translated during tissue treatment. The motion transfer assembly may be motor driven or hand driven by an operator of the system, and may be configured to simultaneously rotate and/or translate one or more treatment elements. The motion transfer assembly may move one or more energy delivery elements in a reciprocating motion.

A protective cap may be included to protect non-target tissue from undesired effects, such as a cap placed in, on or near the Ampulla of Vater and/or the Sphincter of Oddi. The protective cap may be constructed and arranged to be removed within twenty four hours of placement in the patient.

A tissue expanding device may be included such as a tissue expanding device configured to deliver expansion fluid to tissue such as the submucosal layer of the duodenum. The tissue expanding device may include a water jet or deployable needle configured to introduce fluid into the tissue to be expanded.

A tissue manipulating device may be included, such as a radially expandable tissue manipulating device comprising an element selected from the group consisting of: an inflatable balloon; an expandable cage; a deployable arm such as radially deployable arm; and combinations of these. A tissue manipulating device may comprise two or more expandable elements such as expandable balloons or cages that are expanded to contact tissue, and axially advanced or retracted to apply forces to tissue. The tissue manipulating device may perform a function selected from the group consisting of: axial straightening such as straightening of the duodenum or other intestinal tissue; tensioning such as axial and/or radial tensioning; thickness expansion such as expansion of the submucosa of the intestine with an injected fluid (e.g. injected liquid or gas); applying an axial force to tissue; applying opposing axial forces to tissue; applying a radial force to tissue; compressing tissue such as compressing the villi of the duodenum; inducing localized edema or angioedema; expanding the duodenum radially such as to reduce the protrusions of plicae circulares and prevent or reduce under treatment of plicae due to folding over of those plicae by a treatment element; and combinations of these. In some embodiments, two radially expandable elements are mounted to two separate elongate tubes configured to be independently advanced and retracted. A second elongate tube may be slidingly received by the first elongate tube. Alternatively, the first elongate tube and the second elongate tube may be configured in a side-by-side arrangement. In some embodiments, the tissue manipulating device comprises an insufflation device. The tissue manipulating device may comprise one or more tissue penetrating elements.

An agent may be included such as a pharmaceutical or other agent selected form the group consisting of: antibiotics; steroids; mucosal cytoprotective agents such as sucralfate; proton pump inhibitors or other acid blocking drugs; and combinations of these. The agent may be delivered to the patient systemically or at a specific anatomical site.

A procedure completion algorithm may be included such as a time based or action based algorithm configured to indicate when a target tissue treatment is complete, or treatment of a portion of target tissue has been adequately treated. The algorithm may be based on a parameter selected from the group consisting of: a time duration has elapsed; an energy level is achieved; a power level is achieved; a level of energy has been delivered such as a pre-determined number of joules of RF energy; a number of mechanical cycles such as a set of reciprocating motions has been achieved; a tissue change has occurred such as a color change, a texture change or other visual change has occurred; tissue impedance and/or a change is tissue impedance has reached a threshold; a temperature and/or a change is temperature such as a temperature and/or change of tissue temperature has reached a threshold; blood flow and/or a change in blood flow has reached a threshold; a serum hormone level and/or a change in a serum hormone level has reached a threshold; blood sugar level and/or a change in blood sugar level has reached a threshold; submucosal connective tissue is exposed such as when detected by visual inspection or chemical and/or biological detection mechanisms; and combinations of these.

According to another aspect of the invention, a method for treating a patient comprises providing a system including a treatment element, and treating target tissue with the treatment element. The system further comprises an elongate tube with a distal portion, and the treatment element is positioned on the elongate tube distal portion. The patient is typically treated for a disease selected from the group consisting of: Diabetes; Type-1 Diabetes; Type-2 Diabetes; hypercholesterolemia; a metabolic syndrome; disease; celiac disease; obesity; cancer such as bronchoalveolar carcinoma; cystitis; and combinations of these. The system may include one or more of the embodiments listed hereabove, singly or in combination. In some embodiments, a tissue expansion step is performed, such as an injection of fluid into the submucosal space when the target tissue includes mucosal tissue.

The method may further comprise implanting a chronic implant, such as an implant selected from the group consisting of: stent; a sleeve; and a drug delivery device such as a coated stent, a coated sleeve and/or an implanted pump; and combinations of these.

The method may comprise treating tissue such that the new tissue that replaces the treated target tissue functions differently than the pre-treated target tissue. Functional changes may include a change in the types of secretions and/or quantities of secretions from the pre-treated mucosal tissue, such as to treat diabetes and/or obesity. Functional changes may comprise different absorptive properties than the pre-treated tissue.

The method may comprise treating target tissue comprising mucosa of the duodenum, such that the mucosal tissue that replaces the treated mucosa functions differently than the pre-treated mucosal tissue. Replacement mucosal cells may have migrated from one or more of: gastric mucosa and jejunal mucosa. Replacement mucosal cells may exhibit different functions than the pre-treated mucosal cells.

The method may comprise treating tissue such that the new tissue that replaces the treated target tissue has different absorptive properties than the pre-treated target tissue. Changes to absorptive properties can be made to treat one or more patient diseases of conditions including but not limited to hypercholesterolemia, such as when the treated target tissue comprises terminal ileum tissues and/or when the replacement tissue exhibits different cholesterol absorption properties than the pre-treated target tissue.

The method may avoid damage and/or otherwise adversely affecting non-target tissue, such as non-target tissue selected from the group consisting of: tunica serosa of the intestine; the Ampulla of Vater; pancreatic tissue; the tunica muscularis of the intestine; the outermost partial layer of the submucosa of the intestine; bile duct tissue; the pylorus; tissue of a body organ; the Sphincter of Oddi; and combinations of these.

The method may treat target tissue comprising a first portion and a second portion. The first portion may be treated simultaneously with the treatment of the second portion, or sequentially. The first tissue portion may overlap tissue of the second tissue portion. The first tissue portion may be adjacent to the second tissue portion. The first tissue portion and second tissue portion may comprise adjacent partial circumferential tissue portions.

The method may comprise a first tissue treatment and a second tissue treatment, similar or dissimilar to the first tissue treatment. Tissue treatment differences may include but are not limited to: target tissue area treated; target tissue depth treated; target tissue circumferential portion treated; energy delivery type; energy delivery rate and/or amount; and combinations of these.

Treatment of the target tissue may comprise a cellular modification of the tissue selected from the group consisting of: cell death; apoptosis; instant cell death; cell necrosis; denaturing of cells; removal of cells; and combinations thereof. Treatment of the target tissue may comprises one or more of: removal of target tissue cells; initiation of an inflammatory response; and combinations of these. Treatment of target tissue may comprise one or more of: making the target tissue cells non-functional; altering cellular secretions of the target tissue cells such as to prevent cellular secretions; and altering the autocrine and/or paracrine signaling of the target tissue cells.

Treatment of target tissue may cause cells of the target tissue to be replaced, such as replacement by cells with different cellular function such as different cellular secretions.

Treatment of target tissue may result in an acute change such as a change that occurs within twenty four hours of treatment. Alternatively or additionally, treatment of target tissue may occur of an extended period of time, such as a time period greater than twenty four hours or a time period greater than one week.

The method may further comprise selecting the target tissue to be treated. The selection may be based on the patient disease or disorder to be treated, such as a disease or disorder selected from the group consisting of: diabetes including Type-1 and Type-2 diabetes; hypercholesterolemia; a metabolic syndrome and/or disease; celiac disease; obesity; cancer such as bronchoalveolar carcinoma; cystitis; and combinations of these. The target tissue selected may be based on a patient anatomical or physiologic condition, such as an anatomical or physiologic condition selected from the group consisting of: hyperglycemic hyperosmolar state; diabetic ketoacidosis; insulin resistance; pre-diabetes; hypertriglyceridemia; and combinations of these. The target tissue selected may be based on the gross anatomical and/or functional borders of the target tissue. In some embodiments, the target tissue is based on the functional borders between the duodenum and adjacent tissue of the gastrointestinal tract. In some embodiments, the target tissue is based on the functional borders between the four parts of the duodenum.

Target tissue may comprise treatment tissue whose treatment causes a desired therapeutic effect. Target tissue may further comprise a safety margin of tissue comprising tissue proximate the treatment tissue, wherein the safety margin tissue is minimally affected by the tissue treatment, such as safety margin tissue comprising a partial layer of submucosa when the treatment tissue comprises mucosal tissue.

In some embodiments, target tissue comprises at least a portion of the duodenum, typically at least a portion of the mucosal layer of the duodenum. The target tissue may comprises at least a circumferential portion of an innermost mucosal partial layer along at least a segment of the duodenum, such as target tissue comprising tissue selected from the group consisting of: at least a circumferential portion of the innermost mucosal partial layer along the full length of the duodenum; a full circumferential portion of the innermost mucosal partial layer; a full circumferential portion of the innermost mucosal partial layer along the full length of the duodenum; the stem cells at the base of the crypts; the transit amplifying cells; and combinations of these. The target tissue may comprise a full circumferential portion of the mucosal layer along at least a segment of the duodenum, typically spanning the majority of or the full length of the duodenum. In addition to duodenal mucosa, the target tissue may comprise at least a portion of the submucosal layer, such as at least a circumferential portion of an innermost submucosal partial layer along at least a segment of the duodenum. Submucosal target tissue may comprise tissue selected from the group consisting of: at least a circumferential portion of the innermost submucosal partial layer along the full length of the duodenum; a full circumferential portion of the innermost submucosal partial layer; a full circumferential portion of the innermost submucosal partial layer along the full length of the duodenum; and combinations of these. Target tissue may comprise one or more longitudinal portions of the duodenum, and may include the entire length of the duodenum Target tissue may comprise a distal portion of the stomach. Target tissue may comprise a portion of the pylorus contiguous with the duodenum. Target tissue may span tissue between a distal portion of the stomach and a proximal portion of the jejunum. Target tissue may comprise tissue spanning from the pylorus to the ligament of Treitz. Target tissue may comprise a least a portion of the jejumum. The target tissue may comprise a full circumferential portion of the duodenum. Target tissue may comprise a partial circumferential portion of the duodenum, such as a partial circumferential portion of the duodenum proximate the Ampulla of Vater and/or the pancreas. Treatment of duodenal tissue may be performed to treat a disease or disorder selected from the group consisting of: diabetes; obesity; insulin resistance; a metabolic disorder and/or disease; and combinations of these. Treatment of target tissue including duodenal tissue is typically accomplished leaving the duodenum anatomically connected after treatment.

The target tissue may include a depth comprises a full tissue layer, such as a full mucosal layer and/or a full submucosal layer. The target tissue may include a depth comprising a partial tissue layer, such as a partial submucosal layer comprising at least one percent of the full submucosal depth, at least twenty five percent of the full submucosal depth, or at least fifty percent of the full submucosal depth. The target tissue may comprise a depth, a length and a width, and the depth may remain relatively uniform along a majority of the length and the width. Alternatively, the target tissue may comprise a depth, a length and a width, and the depth may vary along the length and/or the width. Varied depth target tissue treatment may be performed in multiple treatment steps, such as multiple steps comprising different energy levels and/or duration of treatment.

In some embodiments, the target tissue comprises at least a portion of terminal ileum tissue extending into the proximal ileum and/or the colon, such as to treat hypercholesterolemia and/or diabetes.

In some embodiments, the target tissue comprises at least a portion of the gastric mucosa, such as when the target tissue comprises tissue that produces ghrelin and/or other appetite regulating hormones and/or when the target tissue treatment is performed to treat an appetite disorder.

In some embodiments, the target tissue comprises bladder wall tissue, such as when the target tissue treatment is performed to treat a disease or disorder selected from the group consisting of: interstitial cystitis; bladder cancer; bladder polyps; pre-cancerous lesions of the bladder; and combinations of these.

In some embodiments, the target tissue comprises tissue selected from the group consisting of: large and/or flat colonic polyps; margin tissue remaining after a polypectomy; and combinations of these, such as when the target tissue treatment is performed to treat cancer cells such as residual cancer cells.

In some embodiments, the target tissue comprises airway lining tissue, such as when the target tissue treatment is performed to treat a disease or disorder selected from the group consisting of: bronchoalveolar carcinoma; other lung cancers; pre-cancerous lung lesions; and combinations of these.

In some embodiments, the target tissue comprises at least a portion of the intestinal tract afflicted with inflammatory bowel disease, such as when the target tissue treatment is performed to treat one or more of: Crohn's disease and ulcerative colitis.

In some embodiments, the target tissue comprises tissue of the oral cavity, such as when the target tissue treatment is performed to treat one or more of: an oral cancer and a pre-cancerous lesion of the oral cavity.

In some embodiments, the target tissue comprises tissue of the nasopharynx, such as when the target tissue treatment is performed to treat nasal polyps.

In some embodiments, the target tissue comprises one or more portions of gastrointestinal tissue selected to treat celiac disease.

In some embodiments, the target tissue comprises one or more portions of gastrointestinal tissue selected to improve intestinal barrier function.

The method may further comprise advancing, retracting and/or rotating the treatment element.

The method may further comprise radially expanding and/or radially extending the treatment element. The treatment element may comprise and/or be mounted to an element selected from the group consisting of: a balloon; a cage; at least one radially deployable arm; and combinations of these. The target tissue may be treated while the treatment element is in a radially expanded state. The treatment element may be configured to radially expand to a diameter of at least 1 cm, or at least 2 cm. Radial expansion of the treatment element may be configured to cause blood to migrate away from tissue proximate the treatment element. Radial expansion of the treatment element may be configured to reduce perfusion of blood in tissue proximate the treatment element. Radial expansion of the treatment element may be configured to compress target tissue, such as when compression of the target tissue is performed during delivery of energy to target tissue.

The treatment element may comprise a deployable cage. The cage may comprise a first deployable arm with a first mounted electrode and at least a second deployable arm with a second mounted electrode. The cage may be expanded to create a full circumferential target tissue treatment (e.g. ablation) without need to reposition the cage. Alternatively the cage may be repositioned multiple times to perform a full circumferential tissue treatment.

The treatment element may comprise an expandable balloon. The balloon may be filled with fluid at an elevated temperature, such as to deliver heat energy to the target tissue. In one embodiment, the fluid may be at a temperature between 65° C. to 90° C. In another embodiment, the fluid is at a temperature above 43° C., typically below 100° C. The balloon may be filled with one or more fluids selected from the group consisting of: air; CO2; saline; and combinations of these. The balloon may include one or more electrodes, such that electromagnetic energy such as radiofrequency energy can be delivered to the target tissue from the one or more electrodes. The one or more electrodes may comprise a flexible electrode. Multiple segmented electrodes may be mounted to the balloon. The treatment element may be a multiple lobed balloon, such as a multiple lobed balloon filled with fluid at an elevated temperature and/or a multiple lobed balloon comprising at least one electrode configured to delivery electromagnetic energy. The treatment element may comprise a second balloon, such as when the treatment element comprises a first balloon filled with hot fluid and a second balloon configured to abrade tissue when the second balloon is translated and/or rotated. In some embodiments, the method includes radially compressing the treatment element, such as radial compression of a balloon, a cage, and/or a radially compressible arm.

The method may comprise conforming the treatment element to the topography of the target tissue, such as when the treatment element includes a conformable balloon and/or a conformable cage.

The method may include treating tissue with a second treatment element, such as a second treatment element mounted to the elongate tube distal portion. Alternatively, a second treatment element may be mounted to the distal portion of a second elongate tube, such as a second elongate tube slidingly received by the first elongate tube. The method may include advancing and/or retracting the first treatment element and/or a second treatment element. The method may include treating target tissue with a second treatment element in a different configuration than the treatment performed by the first treatment element, such as a different form of energy delivery.

Treating of the target tissue may comprise the delivering energy from the treatment element to the target tissue. The energy delivery may comprise a continuous energy delivery. The energy delivery may comprise a pulsed energy delivery, such as energy delivered using pulse width modulation and/or time division multiplexing. The energy delivery may comprise a varied energy delivery such as a varied delivery selected from the group consisting of: varied forms of energy delivered; varied levels of energy delivered; energy varied in a single energy delivery application; energy varied between a first energy delivery and a second energy delivery; and combinations of these. The system may include an optical fiber and the method may comprise delivering energy through the optical fiber. The system may include a gel configured to improve transfer of energy to tissue, such as a gel selected from the group consisting of: thermally conductive gel; electrically conductive gel; optically transmissive gel; and combinations of these.

The target tissue treatment may comprise delivering a first energy delivery to a first portion of target tissue and a second energy delivery to a second portion of target tissue. The first energy delivery and the second energy delivery may comprise the same or different forms of energy. The first energy delivery may be delivered with a first set of energy delivery parameters and the second energy delivery may be delivered with a second, different set of energy delivery parameters.

The two sets of energy delivery parameters may be selected based on differences between the first target tissue portion and the second target tissue portion, such as differences in target tissue thicknesses and/or target tissue proximity to non-target tissue.

The target tissue treatment may comprise delivering energy in a form selected from the group consisting of: electromagnetic energy such as radiofrequency and microwave energy; plasma energy such as argon plasma energy used for coagulation; sound energy such as ultrasound energy; light energy such as laser light energy, infrared light energy and visible light energy; chemical energy; thermal energy such as heat or cryogenic energies; mechanical energy such as mechanical energy delivered by one or more cutting and/or abrading elements: and combinations of these. The energy may be delivered using sonophoresis and/or iontophoresis. The energy may be delivered when the treatment element is in contact with target tissue. Alternatively, the energy may be delivered when there is a gap (e.g. non-tissue such as a gap comprising gas and/or liquid) between the treatment element and target tissue, such as when the energy delivered is laser energy and/or ultrasound energy.

The target tissue treatment may comprise delivering energy in a closed loop energy delivery, such as energy delivered based on signals recorded by one or more sensors of the system. The sensor may comprise at least one temperature sensor and energy delivery controlled based on one or more measured temperature readings. The sensor may comprise an impedance sensor and energy delivery controlled based on one or more measured impedance readings, such as one or more measured tissue impedance readings. The sensor may comprise a sensor configured to provide tissue thickness readings, such as a sensor selected from the group consisting of: an ultrasound sensor; an OCT sensor; OCDR sensor; and combinations of these. Energy delivery may be controlled based on measured tissue thickness, such as measured target tissue thickness. Energy delivery may be varied based on measured depth of energy delivery provided by one or more system sensors. Energy delivery may be controlled based on a parameter selected from the group consisting of: amount of energy delivered; cumulative amount of energy delivered; depth of energy penetration; depth of resultant treatment; tissue temperature; tissue physical characteristics such as color; and combinations of these.

The target tissue treated may comprise a first target tissue portion and a second target tissue portion. The first target tissue portion may have one or more different characteristics than the second target tissue portion. Different characteristics include but are not limited to: tissue type such as tissue layer type; tissue density; tissue thickness; and combinations of these. The first target tissue portion may receive a different treatment than the second target tissue portion, such as a treatment difference selected from the group consisting of: energy level; energy delivery duration; tissue temperature during delivery; and combinations of these. The first target tissue portion may be thinner than the second target tissue portion and the first target tissue treatment may be different than the second target tissue treatment, such as a difference selected from the group consisting of: temperature of target tissue portion treatment; energy level applied during target tissue portion treatment; duration of target tissue portion treatment; and combinations of these.

The target tissue treatment may comprise delivering electromagnetic energy to the target tissue, such as delivery of radiofrequency and/or microwave energy to the target tissue. Radiofrequency energy delivered may comprise bipolar and/or monopolar radiofrequency energy, such as energy delivered through a single electrode and a skin electrode or through energy delivered through an array of electrodes. The electromagnetic energy may be delivered in a single application of energy to a target tissue portion or in multiple applications to a target tissue portion. The target tissue may comprise a first layer of tissue and a second layer of tissue deeper than the first layer of tissue and the system may deliver a first treatment to the first layer of tissue and deliver a second treatment to the second layer of tissue. The first energy delivery may comprise a energy delivery that is at a higher temperature, at a higher power level and/or at a longer duration than the second energy delivery. Delivered electromagnetic energy may be ionizing or non-ionizing energy delivery. Delivered electromagnetic energy may be plasma forming or non-plasma forming energy delivery. Electromagnetic energy may be delivered to cause one or more of: tissue removal; tissue ablation; tissue shrinkage; and hemostasis. Electromagnetic energy may be delivered in combination with delivery of saline proximate to the target tissue, such as sequential or simultaneous delivery of saline.

The target tissue treatment may comprise delivering sound energy to the target tissue, such as sound energy selected from the group consisting of: ultrasonic sound energy; subsonic sound energy; and combinations of these. The system may include at least one energy delivery element configured to deliver the sound energy, such as an energy delivery element comprising a crystal or piezo material. Multiple energy delivery elements may be configured to deliver high intensity focused ultrasound energy.

The target tissue treatment may comprise delivering light energy to the target tissue, such as light energy selected from the group consisting of: laser energy; infrared energy; visible light energy; and combinations of these. Delivered laser energy may comprise energy delivered by a laser selected from the group consisting of: CO2 Laser; KTP Laser; Er:YSGG Laser; Er:glass; Ho:YAG Laser; Ho:YSGG laser; nd:YAG Laser; Nd:YSGG; Nd:doped Laser; Semiconductor Laser; Excimer Laser; Xenon Chloride Laser; Argon Fluoride Laser; a rare earth doped crystal laser; an a gas laser such as an argon or krypton gas laser; a liquid laser such as a dye laser; and combinations of these.

The target tissue treatment may comprise delivering an agent and/or chemical energy to the target tissue. In some embodiments, the target tissue is treated with a chemical peeling agent, such as an agent selected from the group consisting of: an acid; phenol; phenol/croton; and combinations of these. The system may include an outlet port for delivering the agent to the target tissue, such as an outlet port selected from the group consisting of: a nozzle; an opening; a membrane; and combinations of these. The delivered agent may be used to improve or enable the delivery of energy to target tissue, such as when the agent is absorbed by one or more forms of energy and/or when the agent comprises a chromophore configured to support photodynamic and/or ultrasonic energy delivery. The agent may comprise a dye.

The target tissue treatment may comprise delivering heat energy to the target tissue, such as heat energy delivered from a treatment element comprising a hot fluid filled balloon, such as a conformable balloon filled with hot fluid. The hot fluid may comprise a fluid selected form the group consisting of: water; saline; glycerin; steam; and combinations of these. The treatment element may comprise a heatable component such as a heatable component selected from the group consisting of: a cage; a cutter; a wire; and combinations of these. The target tissue treatment may comprise a first energy delivery and a second energy delivery, such as a first energy delivery at a first temperature and a second energy delivery at a second temperature. The system may include magnetic particles configured to delivery heat energy, such as when exposed to a magnetic field such as a magnetic field produced by an MRI. The magnetic particles may be configured to bind to tissue, such as magnetic particles configured to bind to duodenal tissue.

The target tissue treatment may comprise delivering cryogenic energy to the target tissue, such as when the system includes a cryogenic source such as a source of one or more of: CO2; argon; nitrous oxide; and liquid nitrogen.

The target tissue treatment may comprise delivery of mechanical energy to the target tissue such as via an energy delivery element selected from the group consisting of: a cutting balloon; a cutting cage; an expandable element with an abrasive coating and/or an abrasive surface treatment; and combinations of these. The system may further comprise a motion transfer assembly such that the treatment element may be rotated and/or translated to deliver the mechanical energy, such as in a reciprocating motion.

The target tissue treatment may be delivered by at least one energy delivery element of the system, such as an energy delivery element selected from the group consisting of: an electrode; a crystal; a cutting surface; and combinations of these. The system may include at least three energy delivery elements, such as three or more energy delivery elements positioned in an array, such as a radially expandable array.

The target tissue treatment may comprise mechanically abrading the target tissue. The treatment element delivering the mechanical abrasion may comprise one or more of: a balloon with a surrounding abrasive mesh; a balloon with one or more embedded abrasives; and a balloon or other radially expandable element configured to remove tissue. The system may include a motion assembly used to rotate and/or translate one or more treatment elements to mechanical abrade the target tissue.

The target tissue treatment may comprise application of a fluid jet, such as a fluid jet delivering one or more of water; air, $CO_2$, and steam. The fluid jet treatment is typically configured to cause the target tissue to be removed or otherwise become non-functional.

The target tissue treatment may comprise delivering at least two forms of energy. The system may include a first treatment element for delivering a first form of energy and a second treatment element for delivering the second form of energy. The two forms of energy may be delivered simultaneously or sequentially. The first form of energy may be delivered to a first target tissue portion and the second form of energy may be delivered to a second target tissue portion. In one embodiment, the first form of energy comprises mechanically abrading the target tissue. The second form of energy may comprise delivery of heat energy from a hot fluid balloon and/or delivery of electromagnetic energy such as radiofrequency energy.

The method may further comprise inserting the elongate tube distal portion into a body lumen and/or body cavity of a patient. The body lumen and/or body cavity may be a location selected from the group consisting of: gastrointestinal tract; esophagus; stomach; pylorus; duodenum; jejunum; lung; bladder; nasopharynx; colon; airway; oral cavity; and combinations of these.

The method may further comprise inserting a least a portion of the elongate tube through a working channel of a body access device, such as a body access device selected from the group consisting of: an endoscope; a laparoscopic port; a transgastric access device; a vascular introducer; and combinations of these. The at least a portion of the elongate tube may be front-loaded or back-loaded into the body access device.

The method may further comprise advancing, retracting and/or rotating the elongate tube distal portion, such as to advance, retract, and/or rotate one or more treatment elements of the elongate tube.

The method may further comprise deflecting the elongate tube distal portion, such as by activating a deflecting assembly of the system. The deflecting assembly may comprise a pull wire which is retracted or advanced, or a curved mandrel which is inserted and may comprise a shaped memory material configured to change shape as it transition to body temperature. The elongate tube distal portion may be deflected to cause the elongate tube and/or the treatment element to contact the target tissue.

The method may further comprise advancing, retracting and/or rotating a second elongate tube, such as a second elongate tube slidingly received by the first elongate tube or positioned in a side-by-side configuration. The second elongate tube may comprise one or more treatment elements.

The method may further comprise expanding an expandable element, such as an expandable element comprising one or more of a balloon, a cage; and a radially deployable arm. The treatment element may comprise the expandable element or it may be mounted to the expandable element. The method may further comprise expanding a second expandable element, such as a second expandable element comprising a treatment element. The expansive force on the first or second expandable element may be varied, such as to vary the treatment applied to the target tissue, Variation in expansive force may modify one or more of: energy delivered; depth of treatment; and force applied by a mechanical abrasive element. Variation in expansive force may cause a variation in electromagnetic energy delivered, such as to increase radiofrequency energy delivered due to reduced impedance at high expansive forces.

The method may further comprise obtaining a signal from one or more sensors. One or more sensors may be mounted to the elongate tube and/or a treatment element. The one or more sensors may be mounted to an expandable member, and the method may include expanding the member such as to have a sensor contact tissue. The method may include adjusting the target tissue treatment based on one or more signals received from the one or more sensors, such as when the one or more sensors include a sensor selected from the group consisting of: heat sensors such as thermocouples; impedance sensors such as tissue impedance sensors; pressure sensors; blood sensors; optical sensors such as light sensors; sound sensors such as ultrasound sensors; electromagnetic sensors such as electromagnetic field sensors; and combinations of these. The method may comprise adjusting target tissue treatment based on a measured temperature, such as a temperature sensor mounted in, on or proximate to the treatment element. The method may comprise positioning the sensor on a tissue wall, such as a duodenal tissue wall. The method may comprise positioning the sensor within tissue, such as within submucosal tissue as placed during a submucosal injection procedure. The method may include obtaining patient parameter information from the one or more sensors. The patient parameter information may comprise information selected from the group consisting of: temperature information such as tissue temperature information or treatment element temperature; impedance information such as tissue impedance information; pressure information; blood flow information; blood sugar levels; insulin levels; glucagon levels; GIP, GLP-1, GLP-2 and/or other gastrointestinal hormone levels; and combinations of these. The method may comprise adjusting target tissue treatment based on a temperature and/or impedance reading, such as an adjustment to radiofrequency energy or hot fluid energy delivery. The method may comprise adjusting target tissue treatment based on signals received by an Electromyographic sensor, such as signals representing electromyography of the muscularis mucosa. The method may comprise adjusting target tissue treatment based on signals from a sensor selected from the group consisting of: a quantitative calorimetry sensor; a serum level sensor; an imaging sensor such as a sensor configured to produce a signal representative of tissue color such as villi tissue color; and combinations of these. The method may include adjusting the target treatment based on signals received from an imaging sensor, such as an imaging sensor producing signals representative of: image tissue thickness; image tissue vascularity; image ice ball found in cryogenic energy delivery; and combinations of these. The imaging sensor is typically an imaging sensor selected from the group consisting of: X-Ray such as fluoroscopy; CT imaging; MRI; Ultrasound imaging; Molecular Imaging; Nuclear Imaging such as Nuclear imaging with or without glucose tolerance testing; OCT; Spectroscopy such as Tera-Hertz spectroscopy; and combinations of these.

The method may further comprise activation of a functional element, such as a functional element mounted to the elongate tube and/or the treatment element. The functional element may be an element selected from the group consisting of: a sensor; a transducer; a vacuum port; a visualization element or device such as an ultrasound crystal or an optical assembly; and combinations of these. The functional element may comprise a vacuum port and the method include applying a vacuum to cause the treatment element, the elongate tube and/or another portion of the system to come into contact with tissue such as target tissue. The method may include removing tissue such as previously treated target tissue through the vacuum port. The functional element may comprise a visualization device, and the method may further comprise creating one or more images from the visualization device. Typical visualization devices include but are not limited to: visible light camera; ultrasound imager; optical coherence tomography imager; and combinations of these.

The method may further comprise delivering a pressurization fluid via a body lumen pressurization assembly of the system. One or more fluids, such as a liquid and/or a gas, are delivered to the patient through a lumen of the elongate tube and/or a lumen of a body access device such as an endoscope, such as to insufflate (e.g. distend) a body cavity or body lumen such as the duodenum. The fluid may be delivered through a second elongate tube of the system, such as a second elongate tube advanced through a body access device such as an endoscope along with the first elongate tube, in the same or different working channels of the endoscope. An occlusive element of the system may be expanded, such as to prevent migration of the delivered fluid or otherwise cause the delivered fluid to be maintained in a particular lumen or body cavity location. The occlusive element is typically mounted to the elongate tube. Fluid may be delivered and/or maintained at a pressure above approximate 0.5 cm of $H_2O$. Fluid may be delivered at a pressure below approximately 15 cm of $H_2O$.

The method may further comprise placing a body access device of the system into the patient, such as an endoscope. Alternatively or additionally, a body access device may be inserted into the patient may include one or more of: a laparoscopic port; a transgastric access device; and a vascular introducer. The elongate tube may be inserted into the body access device, such as via a front-loading or back-loading procedure.

The method may further comprise creating one or more patient images from an imaging device of the system. The imaging device may be inserted into the patient, such as through a body access device such as an endoscope. The imaging device may comprise an insertable imaging device selected from the group consisting of: visible light camera; ultrasound imager; OCT imager; and combinations of these. The imaging device may comprise an external imaging device such as an imaging device selected from the group consisting of: X-ray; a fluoroscope; an ultrasound image; an MRI; a PET Scanner; and combinations of these.

The method may further comprise activating an energy delivery unit, such as an energy delivery unit of the system configured to provide energy to one or more treatment elements. The energy delivery element may deliver one or more forms of energy in an open loop or closed loop delivery.

The method may further comprise activating a controller and/or a user interface. The user interface may comprise a graphical user interface used to adjust one or more system input parameters. System input parameters may include a parameter selected from the group consisting of: type of energy to be delivered such as RF energy, thermal energy and/or mechanical energy; quantity of energy to be delivered such as a cumulative number of joules of energy to be delivered or peak amount of energy to be delivered; types and levels of combinations of energies to be delivered; energy delivery duration; pulse width modulation percentage of energy delivered; number of reciprocating motions for an abrasive device to transverse; temperature for a treatment element such as target temperature or maximum temperature; insufflation pressure; insufflation duration; and combinations of these. The system input parameter may be a pre-procedural or peri-procedural parameter selected from the group consisting of: mucosal density and/or thickness; mucosal "lift" off of submucosa after a submucosal injection; longitudinal location of target tissue within the GI tract; and combinations of these. The method may further comprise displaying a system output parameter. System output parameters may comprise a parameter selected from the group consisting of: temperature information such as tissue and/or treatment element temperature information; pressure information such as balloon pressure information or insufflation pressure information; force information such as level of force applied to tissue information; patient information such as patient physiologic information recorded by one or more sensors; and combinations of these. The method may include initiating, moderating and/or ceasing treatment delivered by the treatment element. The method may include initiating, moderating and/or ceasing energy delivery by the treatment element. The method may include storing energy delivery information.

The method may include moving one or more system components, such as the elongate tube and/or one or more treatment elements, with a motion transfer element. The motion transfer element may cause one or more system components to rotate and/or translate, such as reciprocating rotation and/o translation. In some embodiments, a treatment element and/or or system component is rotated and translated simultaneously. In some embodiments, the treatment element comprises a mechanical abrader which is rotated and/or translated by the motion. The motion transfer element may comprise a motor driven element and/or an operator driven element.

The method may include placing a protective cap in, on or near non-target tissue such as the Ampulla of Vater and/or the Sphincter of Oddi. The method may include removing the protective cap, such as within twenty four hours of placement in the patient.

The method may include causing tissue to expand, such as target tissue or tissue proximate target tissue. The tissue expansion may comprise causing tissue to expand with a tissue expansion device of the system, such as a tissue expansion device configured to expand submucosal tissue of the duodenum. The tissue expansion device may comprise one or more needles or water jet nozzles, such as one or more deployable needles or deployable water jet nozzles configured to deliver tissue expansion fluid such as saline. Tissue expansion may be performed in multiple locations, such as expansions performed prior to and/or during treatment of a first target tissue portion and a second target tissue portion.

The method may include manipulating tissue, such as with a tissue manipulating device of the system. The tissue manipulation is typically configured to cause one or more of: axial straightening such as straightening of the duodenum or other intestinal tissue; tensioning such as axial and/or radial tensioning; thickness expansion such as expansion of the submucosa of the intestine with an injected fluid (e.g. injected liquid or gas); applying an axial force to tissue; applying opposing axial forces to tissue; applying a radial force to tissue; compressing tissue such as compressing the villi of the duodenum; inducing localized edema or angioedema; and expanding the duodenum radially such as to reduce the protrusions of plicae circulares and prevent or reduce under treatment of plicae due to folding over of those plicae by a treatment element. The method may comprise radially expanding one or more portions of a tissue manipulating device such as a portion including one or more of: an inflatable balloon; an expandable cage; and a deployable arm such as radially deployable arm. The method may include expanding two or more radially expanding portions of a tissue manipulating device. In some embodiments, a first radially expanding portion is mounted to a first shaft and a second radially expanding portion is mounted to a second shaft, the second shaft slidingly received by the first shaft. After expansion to contact tissue such as luminal wall tissue of the duodenum, relative positioning of the first expanding portion and second expanding portion, can be used to apply forces (e.g. tensioning forces) to the tissue. The method may include delivering an insufflation fluid, such as through an endoscope and/or the elongate tube of the system to manipulate tissue (e.g. to distend tissue). The method may include fully or partially occluding a lumen or body cavity, such as to prevent delivered insufflation fluids from migrating from an intending location to be distended or otherwise manipulated. The method may include advancing one or more tissue penetrators, such as to engage tissue and apply one or more forces to the tissue.

The method may further comprise delivering an agent, such as an agent delivered systemically to the patient. The agent may comprise an agent selected from the group consisting of: antibiotics; steroids; mucosal cytoprotective agents such as sucralfate; proton pump inhibitors or other acid blocking drugs; and combinations of these.

The method may further comprise activation of a procedure completion confirmation algorithm. The algorithm may comprise a time-based algorithm, such as an algorithm that monitors time that energy is delivered to target tissue. The algorithm may comprise an action-based algorithm, such as an algorithm that is based on a parameter selected from the group consisting of: an energy level is achieved; a power level is achieved; a level of energy has been delivered such as a pre-determined number of joules of RF energy; a number of mechanical cycles such as a set of reciprocating motions has been achieved; a tissue change has occurred such as a color change, a texture change or other visual change has occurred; tissue impedance and/or a change is tissue impedance has reached a threshold; a temperature and/or a change is temperature such as a temperature and/or change of tissue temperature has reached a threshold; blood flow and/or a change in blood flow has reached a threshold; a serum hormone level and/or a change in a serum hormone level has reached a threshold; blood sugar level and/or a change in blood sugar level has reached a threshold; submucosal connective tissue is exposed such as when detected by visual inspection or chemical and/or biological detection mechanisms; and combinations of these.

According to another aspect of the invention, a system to treat a disease and/or disorders of a patient comprises a treatment element. The treatment element is constructed and arranged to alter a region of the gastrointestinal tract, said alteration selected from the group consisting of: cellular absorptive capacity; cellular hormonal release; and combinations of these.

According to another aspect of the invention, a system to treat a disease and/or disorder of a patient comprises a treatment element and a tissue expansion assembly. The treatment element is constructed and arranged to treat target tissue and the tissue expansion assembly is constructed and arranged to expand the target tissue and/or tissue proximate the target tissue.

According to another aspect of the invention, a method of treating diabetes in a patient comprises selecting a target area of the patients duodenal to remove and removing the patient's duodenal mucosa while leaving the patient's duodenum anatomically intact with respect to the patient's stomach and jejunum. The target area includes an area of the duodenal mucosa that is contiguous with an area in at least one of the patient's jejunal mucosa and gastric mucosa.

The method may include eliminating stem cells in the duodenal mucosa.

The method may include removing the duodenal mucosa by ablating the duodenal mucosa. A balloon may be provided that includes an ablative element, such as an radiofrequency element, positioned in the duodenal mucosa to ablate the duodenal mucosa.

The method may include removing the duodenal mucosa by shaving and/or scraping the duodenal mucosa. A balloon may be provided that includes a cutting device to cause the shaving and/or scraping of the duodenal mucosa.

According to another aspect of the invention, a method of treating diabetes in a patient comprises removing the patient's duodenal mucosa and promoting the patient's jejunal mucosa to grow in a place of the removed duodenal mucosa. The removal of the patient's duodenal mucosa is performed such that the patient's duodenum remains anatomically intact with respect to the patient's stomach and jejunum.

The method may include eliminating stem cells in the duodenal mucosa.

The method may include removing the duodenal mucosa by ablating the duodenal mucosa. A balloon may be provided that includes an ablative element, such as an radiofrequency element, positioned in the duodenal mucosa to ablate the duodenal mucosa.

The method may include removing the duodenal mucosa by shaving and/or scraping the duodenal mucosa. A balloon may be provided that includes a cutting device to cause the shaving and/or scraping of the duodenal mucosa.

The method may include promoting the patient's jejunal mucosa to grow by providing a barrier to stomach mucosa, the barrier preventing the stomach mucosa from growing in the place of the removed duodenal mucosa.

According to another aspect of the invention, a method of treating diabetes in a patient comprises accessing the patient's bile salts and pancreatic enzymes, the bile salts and pancreatic enzymes are unreacted with food ingested by the patient; and delivering the unreacted bile salts and pancreatic enzymes to the patient's duodenum.

According to another aspect of the invention, a method of treating diabetes in a patient comprises accessing the patient's bile salts and pancreatic enzymes, the bile salts and pancreatic enzymes are unreacted with food ingested by the patient; preventing the ingested food from reacting with the patient's bile salts and pancreatic enzymes; preventing the ingested food from reacting with the patient's duodenal mucosa; and delivering the accessed bile salts and pancreatic enzymes to the patient's jejunum.

According to another aspect of the invention, a system for treating diabetes in a patient comprises a treatment device that removes the patient's duodenal mucosa such that the removal leaves the patient's duodenum anatomically intact with respect to the patient's stomach and jejunum. The effect of the treatment is that the patient's jejunal mucosa is promoted to grow in place of the removed duodenal mucosa.

The treatment device for removing the patient's duodenal mucosa may be adapted to eliminate stem cells in the duodenal mucosa.

The treatment device for removing the patient's duodenal mucosa may be adapted to ablate the duodenal mucosa. The treatment device may comprise a balloon configured to ablate the duodenal mucosa. The treatment device may use radiofrequency energy. The system may further comprise a shaving and/or scraping device configured to shave and/or scrape the duodenal mucosa. The shaving and/or scraping device may comprise a second balloon equipped with a cutting device. The treatment device may be adapted to create a barrier to stomach mucosa that prevents the stomach mucosa from growing in the place of the removed duodenal mucosa.

According to another aspect of the invention, a system for treating diabetes in a patient comprises a device that accesses the patient's bile salts and pancreatic enzymes wherein the bile salts and pancreatic enzymes are unreacted with food ingested by the patient; and a device for delivering the unreacted bile salts and pancreatic enzymes to the patient's duodenum.

According to another aspect of the invention, a system for treating diabetes in a patient comprises a device for accessing the patient's bile salts and pancreatic enzymes wherein the bile salts and pancreatic enzymes are unreacted with food ingested by the patient; a device adapted to prevent the ingested food from reacting with the patient's bile salts and pancreatic enzymes, wherein the ingested food is preventing from reacting with the patient's duodenal mucosa; and a device for delivering the accessed bile salts and pancreatic enzymes to the patient's jejunum.

The inventive concepts described herein, along with the attributes and attendant advantages thereof, will best be appreciated and understood in view of the following detailed description taken in conjunction with the accompanying drawings in which representative embodiments are described by way of example.

BRIEF DESCRIPTION OF THE DRAWINGS

The advantages of the technology described above, together with further advantages, may be better understood by referring to the following description taken in conjunction with the accompanying drawings. The drawings are not necessarily to scale, emphasis instead generally being placed upon illustrating the principles of the technology.

FIG. 10 illustrates side and end views of a distal portion of a tissue treatment system including an expandable treatment element comprising a multiple lobed balloon, according to embodiments of the present inventive concepts.

FIG. 11 illustrates a side view of a distal portion of a tissue treatment system including an expandable treatment element comprising a multi-electrode cage, according to embodiments of the present inventive concepts.

DETAILED DESCRIPTION OF THE DRAWINGS

Figure 1:
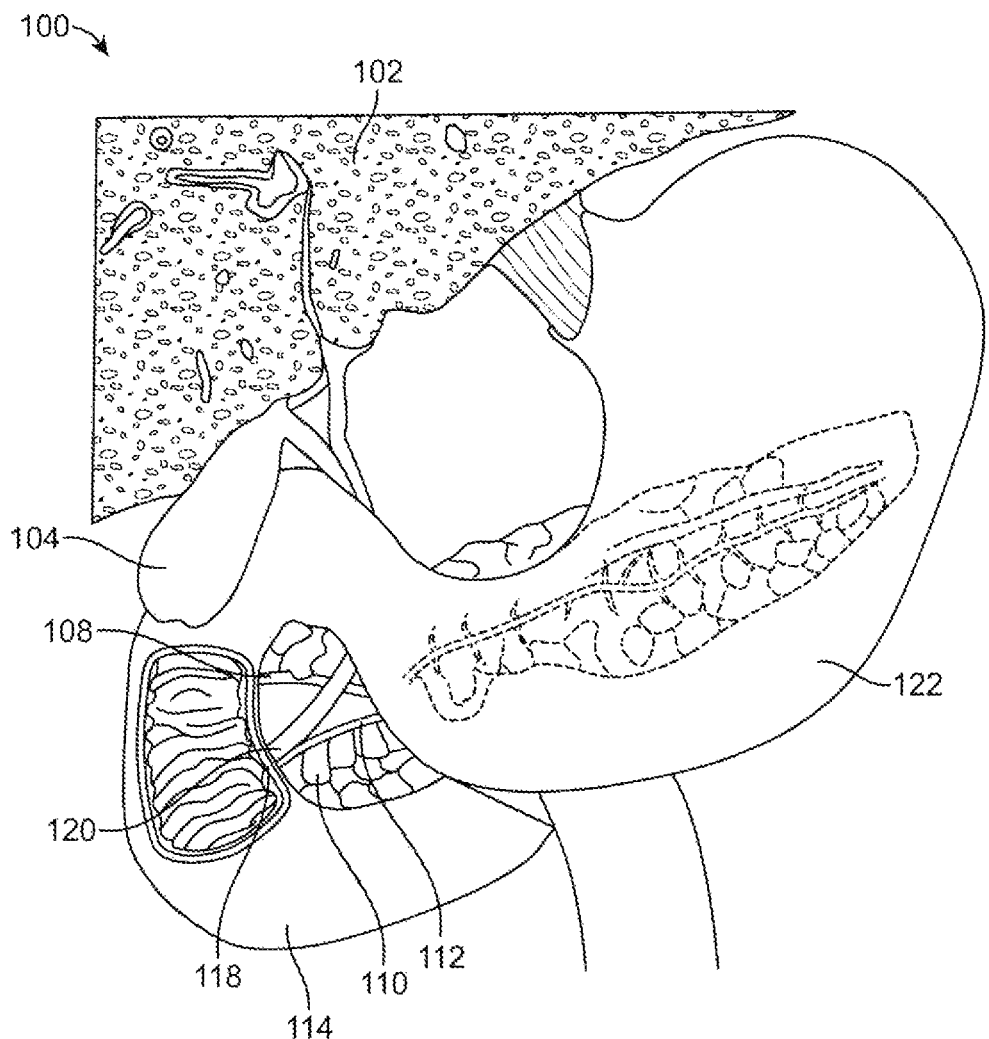
FIG. 1 illustrates certain relevant anatomical features of the human gastrointestinal (GI) tract.

Reference will now be made in detail to the present embodiments of the inventive concepts, examples of which are illustrated in the accompanying drawings. Wherever possible, the same reference numbers will be used throughout the drawings to refer to the same or like parts.

The terminology used herein is for the purpose of describing particular embodiments and is not intended to be limiting of the inventive concepts. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements, and/or components, but do not preclude the presence or addition of one or more other features, integers, steps, operations, elements, components, and/or groups thereof.

It will be understood that, although the terms first, second, third etc. may be used herein to describe various limitations, elements, components, regions, layers and/or sections, these limitations, elements, components, regions, layers and/or sections should not be limited by these terms. These terms are only used to distinguish one limitation, element, component, region, layer or section from another limitation, element, component, region, layer or section. Thus, a first limitation, element, component, region, layer or section discussed below could be termed a second limitation, element, component, region, layer or section without departing from the teachings of the present application.

It will be further understood that when an element is referred to as being "on" or "connected" or "coupled" to another element, it can be directly on or above, or connected or coupled to, the other element or intervening elements can be present. In contrast, when an element is referred to as being "directly on" or "directly connected" or "directly coupled" to another element, there are no intervening elements present. Other words used to describe the relationship between elements should be interpreted in a like fashion (e.g., "between" versus "directly between," "adjacent" versus "directly adjacent," etc.). When an element is referred to herein as being "over" another element, it can be over or under the other element, and either directly coupled to the other element, or intervening elements may be present, or the elements may be spaced apart by a void or gap.

The treatments performed by the systems, devices and treatment elements of the present inventive concepts and in the context of cells or tissues (e.g. a mucosal layer) can refer to the causing of cell death, apoptosis, instant cell death, cell necrosis, denaturing of cells; removal of cells, and/or other alteration of cells such that one or more of their secretions (e.g. the secretion of hormones), absorptions, or other functions is modified or prevented, and/or the treated cells are replaced by new cells that have different secretions or other functions than the pre-treated cells. These modifications to the target tissue cells may occur acutely (at the time of application, e.g. over a time period of less than 24 hours) or may occur over time (e.g. irreversible damage that subsequently results in cell death that typically occurs over a time period of greater than 24 hours, such as a time period of greater than one week). Other uses of the term "treatment" will be clear by context in the specification. Treated cells may be removed, such as via a mechanical abrader or via vaporization by a laser. Treated cells may remain present but be rendered non-functional. Treated cells, such as those treated by thermal ablation, are damaged by the high or low temperature exposure. The removal of these damaged cells is mediated by an inflammatory response, which recognizes the damage cell and removes it. Bacteria, such as bacteria found in the gut, may also break down and therefore remove damaged cells. Treated cells may also simply slough off from the intestinal wall and then be excreted by the body.

The systems, methods and devices of the present inventive concepts may be constructed and arranged to treat various diseases and disorders including diabetes. Recent studies on the mechanisms of diabetes causes and control have revealed that the cause and treatment of diabetes could be closely tied to the gastrointestinal (GI) tract and especially the small intestine. Patients who undergo gastric bypass surgery realize a reduction of Type-2 diabetes symptoms or a complete resolution of the disease. Some recent studies therefore suggest that bypassing of the duodenum and/or jejunum may be one method of treatment for Type-2 diabetes in patients. One theory is based on the concept that the upper intestine of diabetic patients may be the area where abnormal hormonal signaling is produced, causing or favoring the development of diabetes. Type-2 diabetes may result from over-secretion of anti-incretins in the duodenum and jejunum, thereby reducing insulin secretion and blocking the action of insulin. Incretins are gastrointestinal hormones that are produced in response to the flow of nutrients and that increase insulin production. Secretion of incretins increases the secretion and the action of insulin. Anti-incretins, however, suppress the secretion and the action of insulin. Type-2 diabetes may result from the over-secretion of postulated anti-incretins in the duodenum and jejunum, thereby reducing insulin secretion and blocking the action of insulin. Under this hypothesis, a correct balance between incretins and anti-incretins is required to maintain normal glucose levels in the blood. Diabetes results when human cells become resistant to the action of insulin (causing a condition of "insulin resistance"), and when the pancreas fails to produce enough insulin to deal with the glucose load experienced by the body. According to studies, gastrointestinal bypass surgical procedures appear to improve the clinical condition of patients with Type-2 diabetes by excluding the upper small intestine (including the areas of duodenum and proximal jejunum) from the transit of nutrients. This bypass alters the quantity of the hormones released from the hormone-producing cells of the GI tract (by increasing the production of incretins and potentially reducing the production of anti-incretins), thereby resulting in the improvement of Type-2 diabetes.

Portions of the human GI tract relevant to the inventive concepts disclosed herein are illustrated in FIG. 1. The illustrated GI organs include liver 102, gallbladder 104, common bile duct 108, pancreas 110, pancreatic duct 112, duodenum 114, Ampulla of Vater 118, Sphincter of Oddi 120, and stomach 122. The duodenum 114 is typically approximately 25 cm in length. It takes a C-shaped course around the head of the pancreas 110 beginning at the pylorus on the right side and ending at the duodenojejunal junction on the left side where it joins the jejunum. This junction usually takes the form of an acute angle, the duodenojejunal flexure, which is supported by the Ligament of Trietz (not shown). The ducts 112, 108 delivering bile and pancreatic juice from the liver and pancreas, join close to the duodenum 114 at a conversion point called the Ampulla of Vater 118 which empties into the duodenum 114 via the duodenal papilla. The Ampulla of Vater 118 is formed with the union of the pancreatic duct 112 and the common bile duct 108. The Ampulla of Vater 118 is located about halfway along the second part of the duodenum 114. The Sphincter of Oddi 120 is a valve that controls flow of digestive juices through the Ampulla of Vater 118 into the second part of the duodenum 114.

Figure 2:
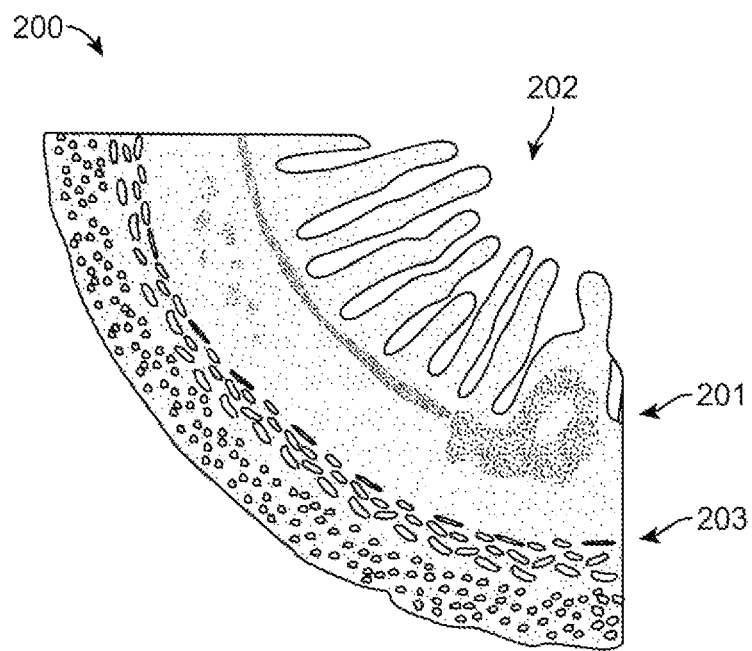
FIG. 2 illustrates a sectional view of the small intestine.

FIG. 2 illustrates a cross section of a small intestine 200. Duodenum 114, as illustrated in FIG. 1, is present in most vertebrates including humans and forms a first portion of the small intestine 200. The duodenum 114 precedes the jejunum (not shown in the figure), which forms a second section of the small intestine 200. The duodenum 114 also includes duodenal mucosa 201 that forms an innermost layer of the duodenum 114, and duodenal submucosa 203 that consists of a layer of connective tissues supporting the duodenal mucosa. Similar to the duodenal mucosa and submucosa, jejunal mucosa and jejunal submucosa (not shown) exist along the jejunum.

As illustrated in FIG. 2, the small intestine 200 includes intestinal villi 202. Intestinal villi 202 are tiny finger-like projections that extend from the wall of the small intestine 200. The intestinal villi 202 have additional projections called micro villi (not shown). Digested nutrients, including glucose, are absorbed into the body through the cells of the intestinal villi 202 and are then carried away by the circulating lymphatics and blood. The intestinal mucosa is composed of several anatomical layers that have varied architecture, function, and form. In the region of the small intestine 200, the intestinal mucosa is interdigitated with a lamina propria basal layer. The intestinal mucosa is composed of three secretory cell types (enteroendocrine, Goblet, and Paneth cells) and one absorptive cell type (the enterocyte). Nutrient transport and absorption occurs in the enterocyte and complex signaling occurs between the various cell types in the mucosa. In particular, the enteroendocrine cells release hormones in response to the presence or absence of local signals, often triggered by the presence and composition of nutrients in the lumen. Stem cells at the base of the crypts of the intestinal mucosa give rise to all four of these cell types and genetically and epigenetically define the behavior and properties of these cells. When the stem cells divide, they can either give rise to daughter stem cells or to a "transit amplifying" population of intestinal mucosa cells. The transit amplifying cells divide rapidly and begin to differentiate into the four cell types above. The enteroendocrine cells, enterocytes, and Goblet cells migrate toward the lumen of the intestine, whereas the Paneth cells migrate back into the base of the crypt, where they establish a stem cell niche with the resident stem cells. These cells migrate toward the lumen and eventually slough into the lumen as they are pushed out by newly dividing cells emerging beneath them. Because all of the cells of a single crypt-villous structure arise from the stem cells at the base of the crypt, an important aspect of this rejuvenative and regenerative process is that the phenotype, behavior, and characteristics of the crypt-villous structure is defined by the properties of the stem cells at the base of its crypt. In this way, regions of intestinal mucosa with different structures and phenotypes (such as gastric mucosa versus intestinal mucosa) behave differently (in large part) because of the different differentiation properties of the stem cells at the base of the gastric and intestinal mucosa, respectively. Circumferentially, the mucosa of any region of the small intestine is largely similar However, axially, there are dramatic differences, as observed by the differences in mucosal properties of the stomach, duodenum, jejunum, etc.

The term "Target Tissue" shall include all of the tissue to be treated by the systems, methods and devices of the present inventive concepts. Target tissue shall also include portions of tissue to be treated, such as a first portion that is treated before one or more other portions that are treated. Tissue of the patient, including the target tissue of the patient, may comprise volumes of tissues in various geometric shapes. Target tissue may include one or more layers of a tubular structure, such as one or more layers of a tubular portion of the gastrointestinal tract. Target tissue may be defined by a length, a width, and a depth, or it may be defined by other three dimensional defining parameters. Target tissue length may comprise a length of a tissue surface, such as the length of a tubular tissue conduit, such as a length of a portion of duodenum or other gastrointestinal tract tissue. Target tissue width may comprise the width of a tissue surface, such as a width comprising a circumferential portion of a tubular tissue conduit, such as a circumferential portion between 1° and 360° of a tubular tissue layer or layers. Partial circumferential target tissue shall refer to target tissue or portions of target tissue less than 360°. Full circumferential target tissue shall refer to target tissue or portions of target tissue covering a full circumference (e.g. 360° of one or more full or partial layers of the gastrointestinal tract). Target tissue depth may comprise the depth projection of tissue beneath a tissue surface, such as the depth of tissue projecting from an inner wall of a tubular tissue conduit such as a depth including at least the full mucosal layer of the duodenum. Tissue layers may comprise full layers or partial layers or anatomically classified tissue layers such as the mucosal and submucosal layers of the gastrointestinal tract. Full layers may comprise two or more partial layers, such as a submucosal layer of the duodenum that comprises a first innermost partial layer and a second outermost partial layer. Full or partial layers may have a constant depth (e.g. thickness) or a depth that varies over the length and or width of the target tissue.

In accordance with an embodiment of the present inventive concepts, duodenal mucosa may be treated (e.g. removed) while leaving the duodenum 114 anatomically connected (i.e., intact with respect to the GI tract). One or more longitudinal portions of the duodenum, typically the entire length of the duodenum or a substantial longitudinal segment thereof, may be treated. One or more layers of duodenal tissue may be treated, typically comprising a full circumferential (e.g. 360°) extent along the surface and full mucosal layer thickness. In one embodiment, the target tissue comprises a substantial portion of the full thickness of the mucosa, inclusive of the intestinal villi, the stem cell layer at the base of the mucosa, and the transit amplifying cells. This target tissue includes a substantially full circumferential and axially contiguous portion of tubular tissue that extends over a target treatment length of the intestine. The target tissue volume (defined by the target tissue length, depth and circumferential portion) is selected to achieve desired therapeutic effects. Treatment of the full thickness of duodenal mucosa (including the stem cell layer at the base of the mucosa) prevents the local regrowth of mucosa and causes a modification of the behavior of the cells of the intestinal mucosa within the treatment area. The treatment of a region of mucosa may alter the function and behavior of both the absorptive cells in a given region of the intestine as well as the secretory cells of that region. Treatments that modify the behavior of target tissue may be configured to alter the capacity of that region of intestine from absorbing nutrients from ingested food. The treatment may also be configured to alter the autocrine and paracrine signaling and/or secretions to and from enteroendocrine cells in the target region. In one embodiment, the treatment is configured, for a given region of intestine, to alter the secretions as well as the autocrine and paracrine signaling communications between absorptive and secretory cells. In another embodiment, the treatment is configured, for a given region of intestine, to alter the absorptive properties of cells. Numerous other target tissue locations should be considered within the spirit and scope of this application and may be chosen as are described in detail herebelow in reference to FIG. 3A.

Figure 3:
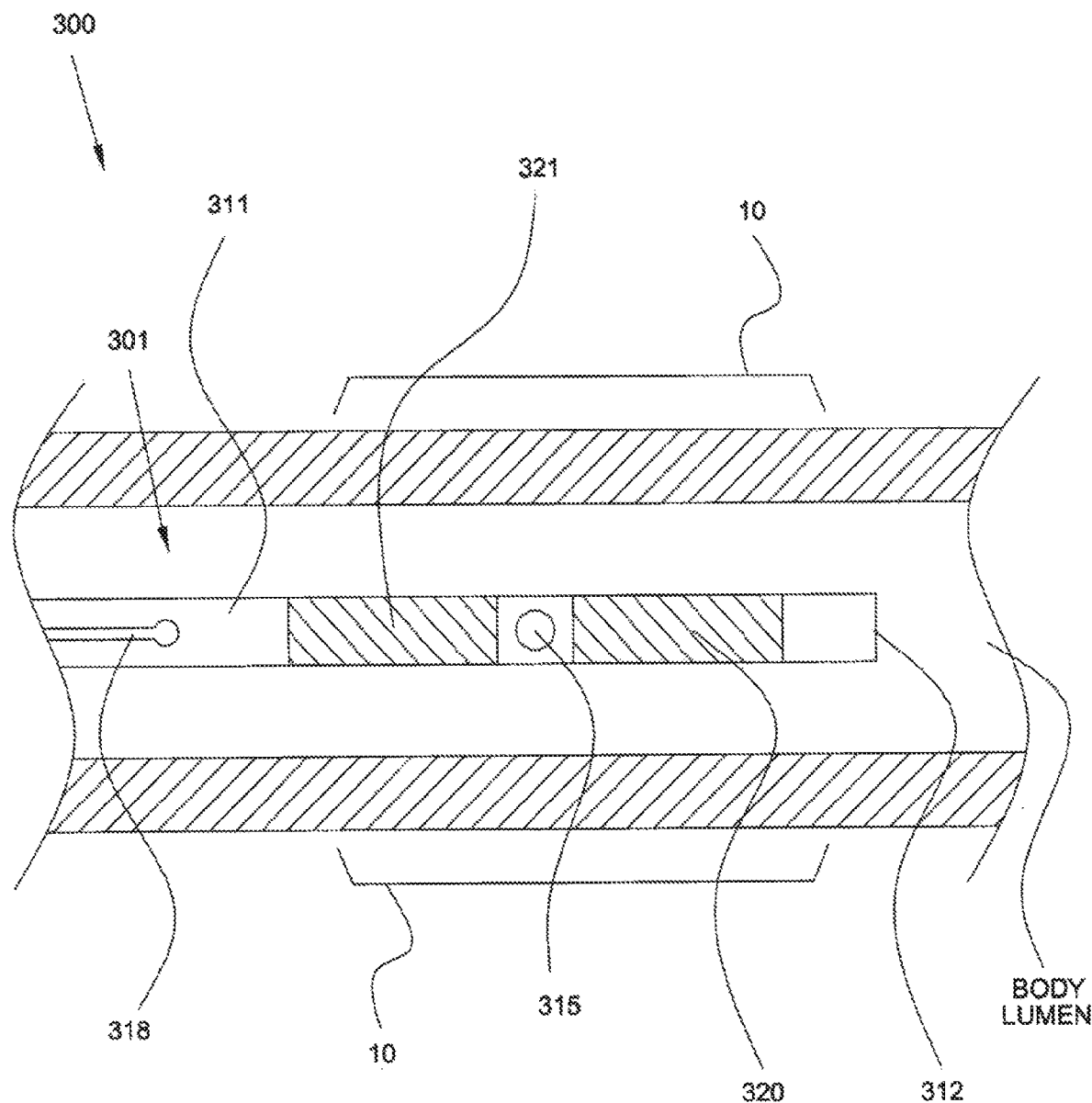
FIG. 3 illustrates a side sectional view of the distal portion of a system for treating tissue, according to embodiments of the present inventive concepts.

FIG. 3 illustrates a side sectional view of the distal portion of a system for treating tissue, inserted into a body lumen, according to embodiments of the present inventive concepts. System 300 is constructed and arranged to treat target tissue 10, including one or more tissue portions as described below in reference to FIG. 3A. System 300 includes elongate device 301 which has been inserted into a body lumen of a patient, such as the duodenum or other portion of the patient's gastrointestinal tract. Elongate device 301 includes shaft 311 with a distal end 312. Shaft 311 is typically a flexible shaft and may be configured to be inserted through a patient body access device, such as an endoscope, a laparoscopic port, a transgastric access device, or a vascular introducer. Shaft 311 may be configured to be front loaded and/or back loaded into an access device such as an endoscope. Back loading may be used when shaft 311 includes one or more distal components that may not be radially compressible or otherwise may not fit within a working channel of an endoscope. Device 301 further includes one or more tissue treatment elements, such as elements 320 and 321 each mounted to a distal portion of shaft 311, and each configured to treat target tissue as is described in numerous configurations throughout this application. Shaft 311 has been advanced, rotated and/or otherwise positioned such that treatment elements 320 and/or 321 are positioned proximate to tissue to be treated, target tissue 10. In one embodiment, treatment elements 320 and 321 are mounted to two different shafts, second shaft not shown, but typically coaxial and slidingly engaged with shaft 111 such that treatment element 320 and treatment element 321 can be independently advanced and retracted. The body lumen may be pressurized, such as by using one or more standard insufflation techniques and/or a technique as described in reference to FIGS. 5, 8A and 8B herebelow. Insufflation fluid may be introduced through one or more lumens of shaft 311, not shown but traveling proximally and connecting to a source of insufflation liquid or gas. Device 301 may have been inserted through an endoscope, not shown but described in detail in reference to FIG. 4 herebelow, and the insufflation fluid delivered through a lumen of the endoscope.

Device 301 may include one or more functional elements, such as functional element 315 mounted to shaft 311 as shown. Typical functional elements include but are not limited to: a sensor; a transducer; a vacuum port; a visualization element or device such as an ultrasound crystal or an optical assembly; and combinations of these. In one embodiment, a vacuum port is configured to remove ablated and debrided tissue. Alternatively or additionally, the vacuum port may be configured to bring shaft 311, treatment element 320 and/or treatment element 321 in contact with tissue. In another embodiment, a functional element is a visualization device such as a visible light camera; an ultrasound imager; and/or an optical coherence tomography visualization device.

Treatment elements 320 and 321 may be configured to perform similar or dissimilar tissue treatments. Treatment elements 320 and/or 321 may be configured to deliver multiple independent treatments such as a mechanical abrasion and another form of energy delivery, performed sequentially or simultaneously. Multiple independent tissue treatments (e.g. therapies), may be performed to improve therapeutic results and/or limit adverse events.

Treatment elements 320 and/or 321 may be expandable, such as by including an expandable cage, a balloon and/or one or more deployable arms configured to make contact with tissue to be treated, such as to deliver energy to tissue during contact with that tissue. Treatment elements 320 and/or 321 may comprise conforming or non-conforming structures, such as conforming or non-conforming balloons. Conforming treatment elements are constructed and arranged to conform to varying topography of the target tissue and tissue proximate the target tissue. Treatment elements 320 and/or 321 may be configured to expand or contract, such as when being advanced or retracted within larger and smaller diameter portions of a lumen. For gastrointestinal applications, treatment elements 320 and/or 321 are typically configured to expand to at least 1 cm in diameter, more typically at least 2 cm in diameter. Expansion of treatment elements 320 and/or 321 is typically performed after the distal portion of shaft 311 has exited a body access device such as an endoscope or laparoscopic port. Treatment elements 320 and/or 321 may be brought into contact with tissue via means other than expansion, such as when the distal portion of shaft 311 can be radially deflected such as through activation of deflecting element 318. Deflecting element 318 typically comprises a pull wire that is tensioned to deflect shaft 311 (e.g. by activating a lever or other control on the proximal end of device 301) or a curved mandrel inserted into shaft 311 (e.g. a Nitinol or other shaped memory alloy shaft configured to curve when transitioned from room temperature to body temperature).

Treatment elements 320 and/or 321 may be configured to deliver energy through a separation distance (e.g. distance between treatment element 320 and/or 321 and target tissue 10), such as with laser or ultrasound energy delivered through a gap, such a liquid or a gas between treatment elements 320 and/or 321 and the target tissue 10.

Energy may be delivered continuously and/or in varying forms and/or levels, so as to achieve different and/or desired therapeutic results. Energy delivery may be provided in a pulsed manner, such as by using pulse width modulation and/or time division multiplexing (TDM). Energy delivery may be varied during a single energy application, such as when an energy delivery element rotates and/or translates as is described in reference to FIG. 8A herebelow.

Figure 7:
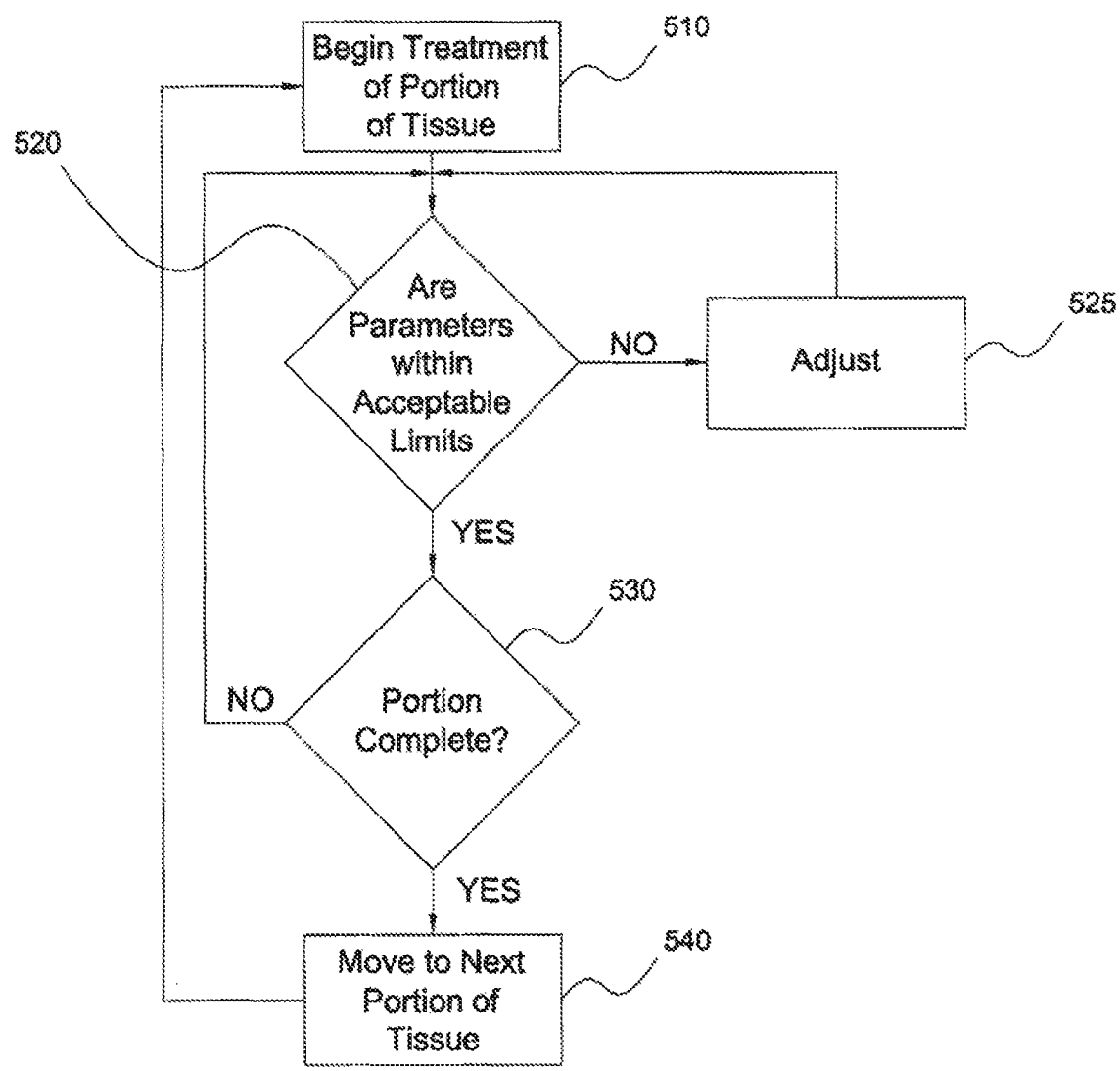
FIG. 7 illustrates a flow chart of a method for treating tissue, according to embodiments of the present inventive concepts.

Energy delivery may be provided in a closed loop manner, as is described in detail in reference to FIG. 7 herebelow. Energy delivery amounts and duration may be based on feedback from one or more sensors of system 300, such as functional element 315. Sensors may be configured to monitor one or more system or patient parameters including but not limited to: amount of energy delivered; cumulative amount of energy delivered; depth of energy penetration; depth of resultant treatment; tissue temperature; tissue physical characteristics such as color; and combinations of these.

Treatment elements 320 and/or 321 may be configured to deliver one or more forms of energy. Typical energies delivered include but are not limited to: electromagnetic energy such as radiofrequency (RF) and microwave energy; plasma energy such as argon plasma energy used for coagulation; sound energy such as ultrasound energy; light energy such as laser light energy, infrared light energy and visible light energy; chemical energy; thermal energy such as heat or cryogenic energies; mechanical energy such as mechanical energy delivered by one or more cutting and/or abrading elements: and combinations of these. Treatment elements 320 and/or 321 may be configured to perform iontophoresis such as irreversible iontophoresis. Treatment elements 320 and/or 321 may be configured to perform sonophoresis such as irreversible sonophoresis. Treatment elements 320 and/or 321 may include multiple energy delivering elements, such as multiple electrodes (e.g. RF electrodes), multiple crystals (e.g. ultrasound crystals), multiple cutting surfaces, and the like. The multiple energy delivery elements may be in the form of an array, such as the expandable arrays of hot balloons and RF electrodes described in reference to FIGS. 10 and 11, respectively, herebelow.

Electromagnetic energies, such as radiofrequency (RF) and microwave energy, may be delivered by one or more of treatment elements 320 and 321. Electromagnetic energy may be delivered through one or more electrodes, such as in a monopolar mode or bipolar mode, described in detail in reference to FIG. 4 herebelow. Bipolar energy may be used for delivery of energy that needs to be limited, such as to avoid damage to non-targeted tissue. The use of bi-polar techniques can reduce the chance of conducting tissue heating in an undesired area or otherwise preventing flow of current in an undesired area. Multiple energy applications may be performed, such as to treat increasingly deeper layer of tissue. The first, second (and possible subsequent) energy applications may be of different duration or power levels. The first application may involve higher energy for deeper penetration. A second application may involve lower energy and may allow greater spatial resolution of energy delivery. One or both applications may include monopolar delivery, bipolar delivery, or a combination of both. Non-ionizing radiation may be preferred, although ionizing radiation may be used.

Electromagnetic energy delivery may be used in the microwave frequency range. Use of microwave energy may be included when avoiding thermal conductivity to ablate tissue is desired. Microwave energy may be employed to achieve rapid and directional heating of tissue.

Tissue ablation (i.e. tissue removal), tissue shrinkage, and hemostasis can be performed using electromagnetic energy delivery that can range from low-voltage, non-plasma-forming tissue-heating conditions (causing tissue coagulation, for example) to higher voltage plasma-forming conditions that can cut or excise tissue rapidly with minimal necrosis of non-targeted tissue. Saline may be delivered proximate the target tissue 10 such as to cool one or more electrodes and/or to increase energy delivery (e.g. improve heating) due to greater conductance. RF energy delivery is typically delivered with a frequency between 100 kHz to 500 kHz. Non-plasma settings occur at lower voltages, typically below about 65 volts rms to 125 volts rms.

Figure 4:
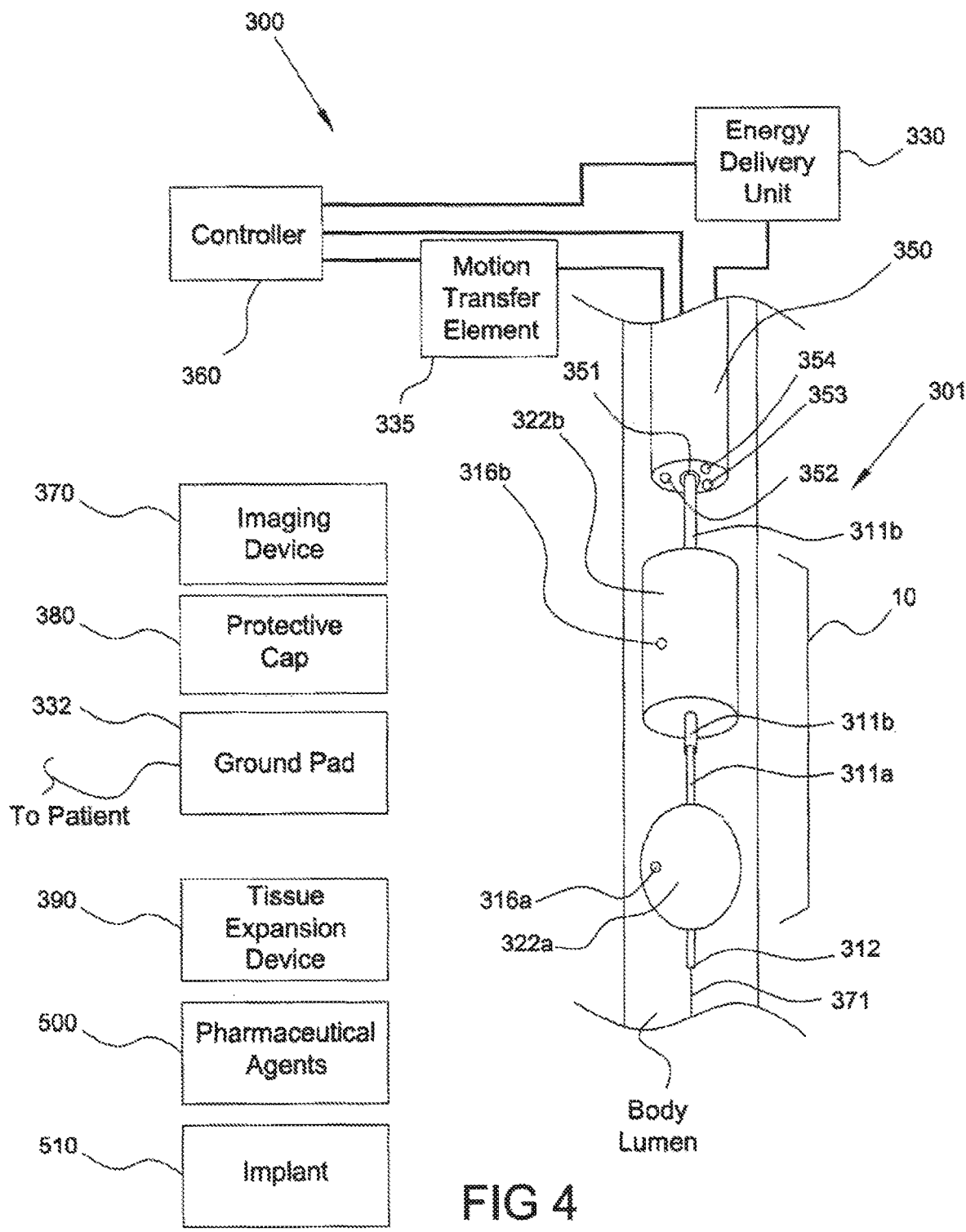
FIG. 4 illustrates a schematic view of a system for treating tissue, according to embodiments of the present inventive concepts.

The use of plasma generating technologies may include producing an electric field between a single or cluster of active electrodes located on the tip of a radiofrequency device and a return electrode (e.g. an electrode located more proximally on the same device or a skin electrode as described in reference to FIG. 4 herebelow). In this configuration, current typically flows through an electrically conductive solution, such as saline, infused proximate the target tissue location. A voltage, typically 150V to 350V is applied between the one or more tip electrodes and the return electrode. This electrical field interacts with underlying fluid (e.g. saline) to excite electrolytes and molecules in the fluid and create a high-density energy field called plasma. The plasma field contains energized particles with sufficient energy to break soft tissue molecular bonds, thus producing conditions that are effective in dissolving tissue at relatively low temperatures. The formation of a gas layer is an important process leading to the plasma-forming conditions. Gas formation at the electrode is the result of an electrochemical process at the surface of the electrodes. As a vapor layer forms (and high impedance of the vapor layer as compared with the saline occurs), the electric field across this area increases dramatically, ionizing and fragmenting the water molecules in the vapor layer and forming the plasma field. This treatment may be applied to treat large tissue surface areas with lower energy treatments. Plasma energy may be delivered by one or more of treatment elements 320 and 321.

Sound energy such as ultrasound energy or subsonic energy may be delivered by one or more of treatment elements 320 and 321. Certain ultrasonic devices, e.g., a harmonic scalpel, may be used for delivery of treatment. Ultrasonic elements may be configured to cause cavitation yielding heating of the tissue, water to rapidly expand and cells to eventually burst. A piezo element, crystal or other subsonic and/or ultrasonic transducer may be positioned close to the area required to be treated and allow for precise energy delivery and minimized thermal damage to non-target tissue. Treatment elements 320 and/or 321 may comprise High Intensity Focused Ultrasound (HIFU) delivery elements. In such embodiments, two or more ultrasound beams may intersect to give a confluence of energy, such as to treat target tissue below a surface.

Light energy such as laser light energy, infrared energy and/or visible light energy may be delivered by one or more of treatment elements 320 and 321. An agent may be applied to the target tissue and light energy may be delivered to the treated tissue. In one embodiment, the agent comprises an exogenous chromophore applied topically to the target tissue.

Laser energy may be delivered by one or more of treatment elements 320 and 321. Any EM spectrum laser may be used as an energy source. An exemplary laser is a $CO_2$ laser. A $CO_2$ laser may ensure high water absorption, such as to minimize undesired thermal damage to tissue. Use of a $CO_2$ laser may also ensure limited hemostasis, avoiding certain sub-mucosal layers to be kept unaffected such that new mucosa may more rapidly repopulate. 532 or KTP laser (Nd:Yag laser) 532 NM wavelength, which may be highly absorbed by blood, may be used in highly vascularized tissues. Short pulsing of laser energy may target vessels without impacting surrounding tissue. The laser may be configured to treat tissue by removing or otherwise affecting its blood supply. An Erbium:YAG or Erbium:YSGG laser, and the like (close to 2.94 microns of laser wavelength), may also be used. These lasers may provide higher water absorption, and may be used with target tissue portions that include thin or shallow segments, such as in when used for tissue resurfacing when thin layers of cells are removed at a time. These types of lasers may also result in minimal hemostasis. A pulsed holmium laser such as a 2 micron laser may be used. These lasers provide high water absorption. Pulsing of these lasers may require large amounts of input energy. CW lasers of approximately 2 microns may also be used. In one embodiment, a laser wavelength is chosen that is close to but not equal to the water peak, such as to provide increases thermal necrosis and increased hemostasis.

Generally, a laser having a wavelength that is on a peak or near a peak of the water absorption curve such as peak at 1.96 microns, peak at 2.94 microns, and peak at 10.6 microns may be chosen. Based on requirements, a combination of ablation and necrosis (thermal damage) may also be desired. The combined effect of thermal damage and ablation may be helpful in mitigating infection risk. Diode lasers of 800 nm, 980 nm, and various other wavelengths between 1300 nm and 2000 nm may be used to coagulate tissue. Nd:Yag lasers at 1064 nm may also be used to coagulate tissue. The depth of penetration may depend on the chosen wavelength of the laser. Excimer laser (PRK and Lasic), Xenon Chloride, and Argon Fluoride may be used for molecular dissociation. These lasers may ensure very precise zones of tissue treatment (e.g. ablation) with no thermal damage to non-target tissue, thereby achieving clean cuts. These lasers may assist in removal of endothelial layers or other tissue layers such as to promote rapid re-growth of target tissue layers from the adjacent areas (e.g. adjacent areas with different characteristics). Numerous types of lasers may be used including but not limited to: a rare earth doped crystal laser; a gas laser such as an argon or krypton gas laser; a liquid laser such as a dye laser; and combinations of these.

Infrared energy may be delivered to treatment elements 320 and/or 321, such as light between 700 nm and 2000 nm in wavelength, or combinations of these wavelengths that may give the desired tissue treatment. Visible light, approximately 530 nm could also be used. If a narrow waveband is desired, a non-laser source, such as a xenon lamp typically including a filter, may be included.

Agents, such as chemicals, and/or chemical energy may be delivered by one or more of treatment elements 320 and 321. In certain embodiments of the present inventive concepts, chemicals may used to remove or ablate the target tissue, such as the duodenal mucosa or its stem cells. Chemical peeling agents such as acids, phenols and phenol/crotons may be delivered by treatment elements 320 and/or 321, such as through a drug delivery element such as a nozzle, an outlet port or a membrane. Photodynamic therapy (creating a chemical reaction with exposure to light) may be used to activate one or more agents. Chemical agents can be delivered to enable or improve energy delivery. In one embodiment, the agent includes a tissue modifying agent, such as a dye or other agent applied to the target tissue surface or injected into the target tissue. This particular agent may be configured to be activated during an energy delivery procedure, such as to perform precise ablation of tissue. For example, target tissue could be stained with a chemical (e.g., methylene blue), and then an energy source could be used that is preferentially absorbed by that chemical dye. In this embodiment, heating is limited and thus the treatment area can be precise and limited to the narrow depth of the stained tissue. A chromophore that may be a target for photodynamic or ultrasound may be employed.

Thermal energies such as heat energies may be delivered by hot liquid filled balloons; heatable cages; heated cutters (e.g. scalpels) or wires; and the like. In one embodiment, treatment element 320 and/or 321 comprise a balloon filled with and/or fillable with hot fluid, such as hot water, saline or glycerin, or a hot gas such as steam. The balloon may be configured to easily conform to the target tissue surface. The expansive properties of the balloon allow for a low profile device (e.g. to be inserted through the lumen of an endoscope), while accommodating expansion into large lumens or other areas, such as the lumen of the duodenum. Heated and/or cooled fluids can be introduced into treatment elements 320 and/or 321 such as to create varied heating and cooling treatments for the target tissue. Precision of tissue treatment may be achieved with a varied temperature approach, such as when system 300 includes one or more temperature sensors monitoring tissue temperature, the temperature of treatment elements 320 and/or 321, and/or the temperature of a fluid delivered to treatment elements 320 and/or 321. Treatment may include multiple heat application steps, such as multiple steps performed at similar or dissimilar temperatures.

In one embodiment, magnetic particles are placed in, on or near the target tissue, and magnetic fields are used to heat the particles to ablate tissue. The particles may be configured as a solution of nanoparticles and may include a receptor that is expressed only in duodenal tissue. An MRI or other magnetic field producing device can be used to selectively heat these particles and thus selectively heat the duodenum 114. Molecular targeting within the duodenum 114 may also be performed, such as through the use of an MRI-absorbing particle attached to a targeting moiety, which preferentially binds to a molecular target. After delivery into the target tissue area or other patient body location, these particles bind to a target, and an MRI or other magnetic field may be applied to heat the target and surrounding cells.

Thermal energies such as cryogenic energies may be delivered by one or more of treatment elements 320 and 321. In these embodiments, a cryogenic sources such as a source of $CO_2$, argon, nitrous oxide, liquid nitrogen, and the like may be utilized to treat the target tissue.

Figure 12:
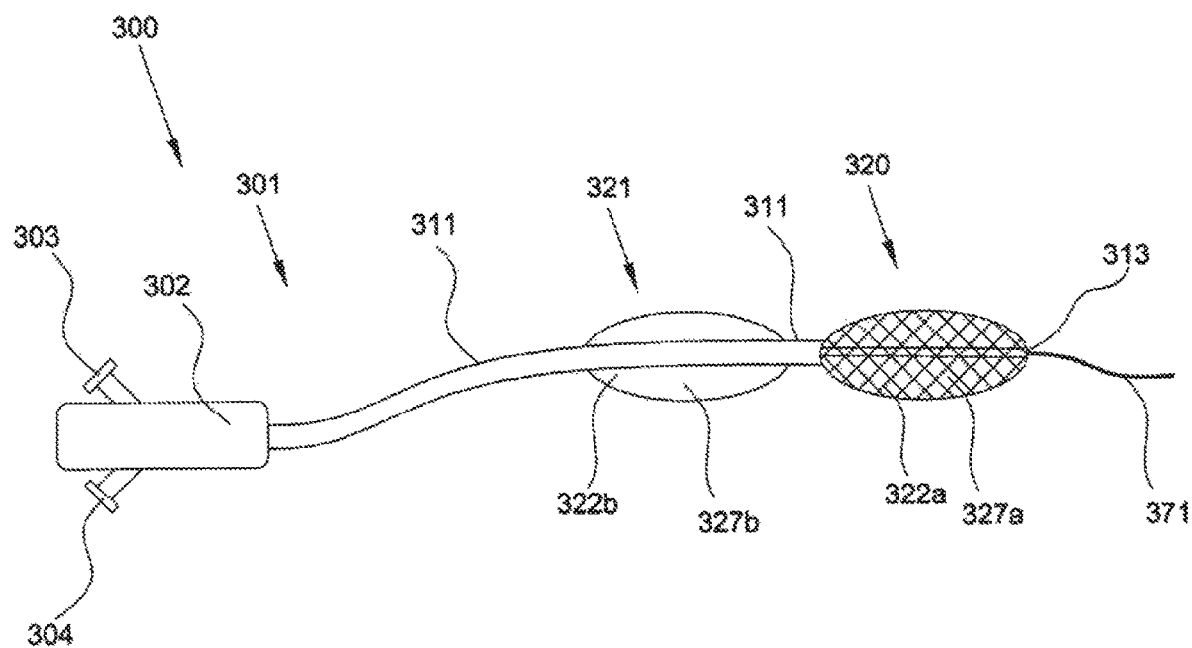
FIG. 12 illustrates a side view of a tissue treatment system including two tissue treatment elements, a balloon supported mesh abrader and a balloon configured for hot fluid containment, according to embodiments of the present inventive concepts.

Mechanical energies may be delivered by cutting balloons or cages; expandable elements with abrasive coatings, surface treatments and/or coverings (e.g. the balloon with abrasive mesh covering described in reference to FIG. 12 herebelow); and the like. In one embodiment, treatment elements 320 and/or 321 comprise a polyethylene terephthalate (PET) balloon with embedded abrasives. Abrasive elements or surfaces may comprise micro-abrasive elements or surfaces.

Numerous abrasion devices and elements (e.g. dermabrasion elements) may be included in treatment elements 320 and/or 321. These abrasive elements may be applied to the surface of the target tissue (e.g. apposed to the intestinal wall), and treat the target tissue when a rotational or translation motion is applied. In this application, abrasion includes rubbing a rough surface which is apposed to the wall of the intestine, or scraping a blade or semi-sharp element along the wall of the intestine. Cutting may be used to excise or otherwise remove tissue that has been previously treated, such as via ablation or a previous abrasion procedure.

In another embodiment, treatment elements 320 and/or 321 may comprise a high speed fluid jet nozzle, such as a nozzle configured to deliver a pulsed, directed spray of water, air, $CO_2$ and/or steam and configured to treat target tissue, such as to render target tissue cells non-functional. In this embodiment, the fluid jet may physically remove the target tissue layer and cells from their in-situ location.

System 300 of FIG. 3 does not include an implanted component or device, only body inserted devices that are removed at the end of the clinical procedure, such as devices removed within 8 hours of insertion, within 24 hours of insertion and/or within one week of insertion. In an alternative embodiment, an implant may be included. Implants include but are not limited to: a stent; a sleeve; a drug delivery device such as a coated stent, a coated sleeve and/or an implanted pump; and combinations of these.

The devices of the present inventive concepts include one or more treatment elements that are constructed and arranged to treat target tissue, such as treatment elements 320 and 321 of FIG. 3. Target tissue selected for treatment may depend on a number of factors including the one or more diseases or disorders of the patient to be treated. Patient anatomical or physiologic conditions may also impact the target tissue selected for treatment and/or particular tissue not to be treated (non-target tissue). Typical diseases and/or disorders to be treated include but are not limited to: diabetes including Type-1 and Type-2 diabetes; hypercholesterolemia; a metabolic syndrome; disease; celiac disease; obesity; cancer such as bronchoalveolar carcinoma; cystitis; and combinations of these. Such patient anatomical or physiologic conditions include but are not limited to: hyperglycemic hyperosmolar state (previously known as hyperosmolar non-ketotic coma); diabetic ketoacidosis; insulin resistance; pre-diabetes; hypertriglyceridemia; and combinations of these.

Figure 3A:
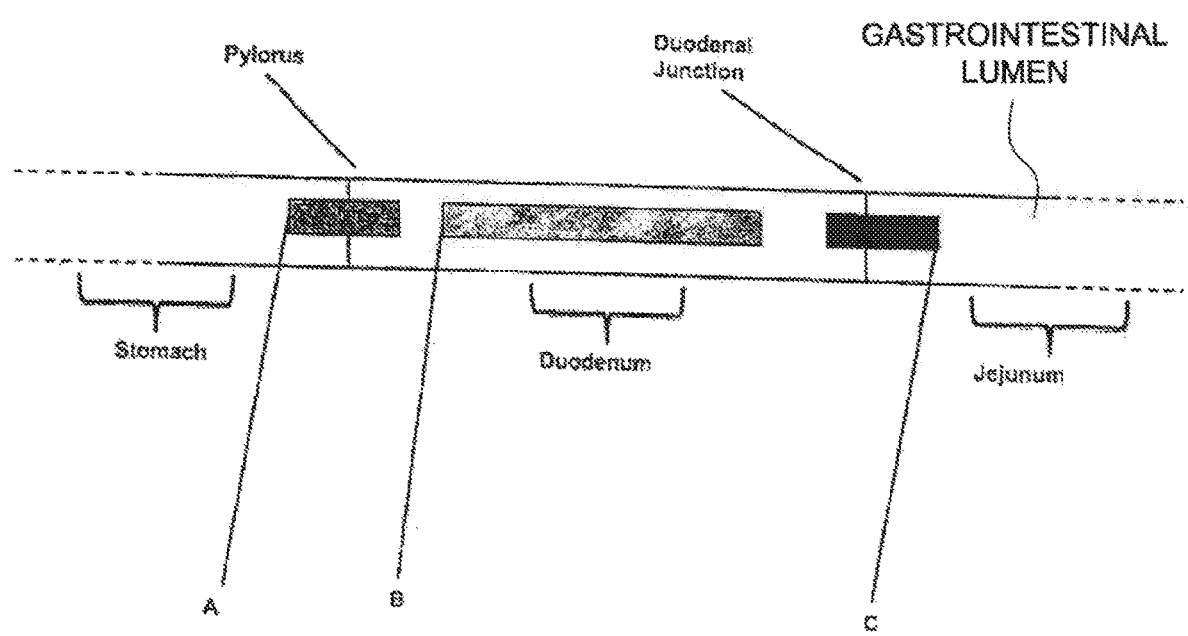
FIG. 3A illustrates potential treatment regions of the gastrointestinal tract, according to embodiments of the present inventive concepts.

FIG. 3A schematically illustrates longitudinal regions of the gastrointestinal tract which may be selected as target tissues for treatment. Other body locations may be additionally or alternatively chosen to treat one or more diseases or disorders. Other body locations may be hollow body organs like the stomach, duodenum and jejunum, and may include relatively flat (i.e. non-tubular) tissue surfaces. In one embodiment, the target tissue includes one or more segments of the gastrointestinal tract, such as to treat one or more of: diabetes; hypercholesterolemia; a metabolic syndrome and/or disease; obesity; and combinations of these. The target tissue may include at least a portion of the duodenum such as to treat a patient with Type-1 and/or Type-2 diabetes. Type-2 diabetes is characterized by insulin resistance, when the insulin-producing capability of the patient is functioning normally or near normally. Blood glucose does not respond as it would in a non-diabetic patient due to abnormal hormone production in the duodenal mucosa. Ingested glucose can lead to complex absorption and signaling patterns in various regions of the intestine as it passes through the alimentary canal. Treatments aimed at lowering blood sugar and treating Type-2 diabetes can be achieved by treating target tissue in one or more portions of the gastrointestinal tract. The target tissue treatment alters the absorption of glucose and/or alters the mucosal signaling from and/or between cells of the intestinal mucosa in response to a glucose signal. Treatment of the duodenal mucosa may reduce the insulin resistance of the Type-2 diabetic patient and improve blood glucose control.

The target tissue may include the terminal ileum and extend into the proximal ileum and/or the colon. Cholesterol and bile salts are absorbed into the body from the alimentary canal via cholesterol and bile receptors that are predominantly located in the terminal ileum. The treatment of the terminal ileum can alter the absorption of cholesterol and bile acids from this region of the intestine and alter all downstream signaling in significant ways. Because the absorption of cholesterol and bile salts in the terminal ileum is known to influence glucose homeostasis as well as cholesterol levels, treatment of the terminal ileum may be employed in the treatment of Type-2 diabetes as well as hypercholesterolemia. The target tissue may include gastric mucosa extending from regions that produce ghrelin and/or other hormones that regulate appetite, such as to treat obesity and/or an appetite disorder. In yet another embodiment, the target tissue may include bladder wall tissue, such as to treat interstitial cystitis, bladder cancer, bladder polyps, or pre-cancerous lesions of the bladder. The target tissue may include large or flat colonic polyps or marginal tissue after polypectomy, such as to eliminate residual cancer cells and improve likelihood of sufficient margins in cancer removal. The target tissue may include the lining of one or more airways, such as to treat bronchoalveolar carcinoma, other lung cancers, or pre-cancerous lesions. The treated airway lining may be replaced with a new cellular layer devoid of pathologic lesions. The target tissue may include segments of the intestinal tract afflicted with inflammatory bowel disease, such as Crohn's Disease or Ulcerative Colitis. The target tissue may include segments of the oral cavity to treat oral cancers or pre-cancerous lesions of the oral cavity. The target tissue may include the nasopharynx, to treat nasal polyps.

The target tissue may be selected such as to treat celiac disease. In celiac disease, the intestinal mucosa is characterized by blunted villi and a reduce ability to absorb nutrients. Treatment of the mucosa restores the absorptive function of the intestine. Celiac disease is also characterized by a failure of the intestinal barrier function, leading to intestinal wall permeability and the passage of macromolecules into the intercellular spaces, triggering an autoimmune response (Fasano 2005). Treatment of the intestinal mucosa improves the intestinal barrier function.

As shown in the embodiment of FIG. 3A, target tissue area A may include a longitudinal tissue portion spanning a distal portion of the stomach to a proximal portion of the duodenum, this target tissue area A including the pylorus. Target tissue area B includes a longitudinal portion spanning a segment of the duodenum. Target tissue area C includes a longitudinal portion spanning a distal portion of the duodenum. One aspect of an embodiment of the present inventive concepts includes the selection of the target tissue. The selection of the target tissue involves consideration of the gross anatomical and/or functional borders of the tissue to be treated, such as the anatomical and functional borders between the duodenum and other adjacent components of the GI tract, or the borders between the four parts of the duodenum itself. In one embodiment, the target tissue selected includes at least the entire length of the duodenum. A distal portion of the stomach and/or a proximal portion of the jejunum may also be included. In one embodiment, tissue between the pylorus and the ligament of Treitz (duodenum-jejunum junction) is treated.

In addition to its longitudinal location, the width or portion of circumference of tissue to be treated must be chosen. In a typical embodiment in which the target tissue includes a portion of the duodenum and/or the jejunum, a full circumferential (e.g. 360°) treatment is performed. In an alternative embodiment, at least a portion of the length of the target tissue receives a partial-circumferential (e.g. less than 360°) treatment. In one embodiment, the target tissue includes a majority of the length of the duodenum, and the depth of the target tissue includes a full 360° along the target length. In another embodiment, a partial circumferential portion is treated proximate the Ampulla of Vater, to prevent or reduce any damage to that anatomical location. In yet another embodiment, a partial circumferential treatment is performed in the portion of the duodenal wall that abuts or is otherwise proximate to the pancreas, to prevent overheating the pancreas and increasing the risk of pancreatitis.

In addition to the length (e.g. longitudinal portion) and width (e.g. circumferential portion) of the target tissue, a depth along the length and width locations must be chosen. The depth or depths chosen may be relatively uniform in magnitude (e.g. number of millimeters of depth), or the depths chosen may vary. The depths chosen may be related to tissue type, rather than actual distance, such as a depth representing the thickness of a tissue layer, such as a full or partial mucosal or submucosal layer, irrespective of actual thickness of those full or partial layers. In a typical embodiment in which the target tissue includes a portion of the duodenum and/or the jejunum, the layers or portions of layers of tissue are chosen. In one embodiment, the target tissue includes a majority of the length of the duodenum, and a full 360° circumferential treatment includes at least all of the mucosal layer along the target length, including the stem cells positioned at the base of the crypts and/or the transit amplifying cells. In one embodiment, such as for the treatment of diabetes, the full mucosal layer and at least a portion of the submucosal layer (layer 203 as shown in FIG. 2) is target tissue, such as at least 1%, at least 10%, at least 25%, or at least 50% of the submucosal layer 203.

Selection of target tissue location, length, width and/or depth is chosen in order to effect a desired treatment change, typically in the area of tissue to be treated. In one embodiment, tissue is treated such that replacement tissue performs in a different manner than the original target tissue. The target area may be treated such that in the subsequent healing process, new tissue alleviates and/or eliminates one or more patient diseases or disorders, such as diabetes in the various treatments of the duodenum and/or the portions of the gastrointestinal tract proximal and distal to the duodenum. Promoting or effecting regrowth of new mucosal tissue of the duodenum is a treatment goal in some embodiments of the present inventive concepts. Re-growth of duodenal mucosa may result in a "healthier" or "more normal" mucosa to come back in its place. In other such embodiments, re-growth of the treated area may comprise migration of new mucosa from the gastric mucosa on one side and the jejunal mucosa on the other side (e.g. due to the stem cells that populate the mucosa from either end may retain their native physiologic state and essentially replace the duodenal mucosa with one of or a mixture of gastric and jejunal mucosa). Accordingly, in such embodiments, the step of targeting involves selecting an area to treat that includes duodenal mucosa as well as a contiguous area up to and/or beyond the duodenal junction into a section of the jejunum thereby including jejunal mucosa. This target treatment area would promote the re-growth of jejunal-type mucosa in the place of the removed duodenal mucosa. Alternatively, re-growth of the treated area may comprise migration of new mucosa from proximal and/or distal portions of duodenal mucosa (e.g. due to the stem cells that populate the duodenal mucosa in these proximal and/or distal portions having preferred function than the treated duodenal mucosa). The systems and methods of the present inventive concepts treat target tissue such that modified tissue replaces it such as to treat a patient disease or disorder.

For certain applications, modification of the tissue's enteroendocrine properties is desired. While the new tissue may be mucosal tissue as is described hereabove, it alternatively may be fibrous or scarred tissue, or some hybrid of mucosal cells and other cells, or some other tissue type resulting from the healing process. For treatment of diabetes and/or obesity, the replacement tissue has different hormonal functions than the pre-treated tissue, as are determined by the quantities and secretions of different types of enteroendocrine cells in the new mucosal tissue. Alternatively or additionally, treatment of diabetes and/or obesity includes replacement tissue with different absorptive properties, For treatment of hypercholesterolemia, replacement tissue in the terminal ileum has different absorptive properties than the pre-treated tissue (e.g. different absorption of cholesterol), as determined by the quantities and types of absorptive cells in the new terminal ileum mucosal tissue.

In other such embodiments, the step of targeting involves selecting an area to treat that includes duodenal mucosa as well as a contiguous area up to and/or beyond the pylorus at the border with the stomach, thereby including the gastric mucosa. Targeting this area promotes the re-growth of gastric-type mucosa in the place of the removed duodenal mucosa.

In other such embodiments, it may be that promoting growth of duodenal mucosa from one part of the duodenum in the place of the treated duodenal mucosa (in another part) is desirable. In such embodiments, therefore, the step of targeting involves selecting an area to treat that includes duodenal mucosa as well as a contiguous area up to and/or beyond the border between the parts of the duodenum hereby including the duodenal mucosa from a different part of the duodenum. Combinations of any of the above targeting scenarios may also be performed.

Target Tissue treated may include continuous portions of tissue or discontinuous portions of tissue, including continuous or discontinuous lengths, widths (e.g. circumferential portions) or depths (e.g. layers) of tissue. Target tissue may include multiple lengths, multiple cross sectional portions and/or multiple depths. Target tissue may be treated in multiple steps. A first treatment length, width and/or depth of treated tissue may overlap a second treatment length width and/or depth of treated tissue. A first treatment may be similar or dissimilar to a second treatment, such as a difference selected from the group consisting of: target tissue area treated; target tissue depth treated; target tissue circumferential portion treated; energy delivery type; energy delivery rate and/or amount; and combinations of these.

In addition to treating target tissue, the treatment elements or other components of the systems of the present inventive concepts may be further constructed and arranged to avoid treating or otherwise adversely effecting non-target tissue. For treatment of the intestine, non-target tissue typically includes the outer layer of the intestine, the tunica serosa. Non-target tissue for intestinal treatment typically also includes the Ampulla of Vater and the pancreas. Non-target tissue may include the tunica muscularis and/or the outermost layer of the submucosal layer 203. Other locations for non-target tissue may include but are not limited to: bile duct; pylorus; one or more organs; and combinations of these.

Target tissue may include tissue whose treatment causes a desired therapeutic benefit, plus a safety margin comprising neighboring tissue to which treatment has no or minimal adverse effects. For example, in the treatment for diabetes, removal of all mucosal layers of the duodenum (or a segment of the duodenum), may achieve the desired therapeutic benefit without removal of the submucosal layer. However the target tissue may include all or part of the submucosal layer, since treatment of the submucosal layer has minimal adverse effects. At least the innermost partial layers of the submucosal layer are used as the safety margin, and its inclusion in the target tissue ensures that the full mucosal layer is treated. Required precision of treatment in the safety margin is thus reduced, simplifying the function of a treatment element such as an energy delivery treatment element. In this embodiment, the treatment tissue depth includes all of the mucosal layer plus at least a portion of the submucosal layer, and this depth of tissue is treated for the determined length (e.g. at least the full length of the duodenum) and the determined width (e.g. a full 360° along the determined length).

Layers beyond the submucosal layer, such as the tunica muscularis and the tunica serosa, may be determined to be non-target tissue as treatment in these areas may cause undesired effects (e.g. perforation of the intestine). Length of target tissue selected (e.g. length of gastrointestinal tract selected) for treatment may be similar to the depth of treatment selected as described above. Again for the treatment of diabetes, the complete length of the duodenum may achieve the desired therapeutic benefit without removal of the tissue proximal and distal to the duodenum. However target tissue may include a portion of the tissue proximal to the duodenum (i.e. all or a portion of the pylorus), and a portion of the tissue distal to the duodenum (i.e. a portion of the jejunum), such as to ensure that the entire length of the duodenum is treated. Such complete duodenal treatment may ensure that duodenal mucosal regrowth comprises only tissue migrating from the jejunum and the stomach or pylorus (i.e. not from any untreated duodenal mucosa). Treatment parameters, such as energy delivery parameters, may be adjusted along the length of a conduit of tissue to be treated, such as to accommodate varying tissue types and densities, varying wall thicknesses, etc. For example, the distal duodenum typically has thinner walls than the proximal duodenal walls. Treatment in the distal duodenum might be performed at a lower temperature, a lower energy level, and/or for a shorter duration than treatment in the proximal portion of the duodenum.

FIG. 4 illustrates a schematic view of a system for treating tissue, according to embodiments of the present inventive concepts. System 300 is constructed and arranged to treat target tissue 10, including one or more tissue portions as described above in reference to FIG. 3A. System 300 includes a multiple filament elongate device 301 comprising shafts 311a and 311b. Shaft 311a has a distal end 312. Shafts 311a and 311b are sized and configured such that shaft 311a is slidingly received by shaft 311b. Shafts 311a and 311b have been inserted through a working channel (e.g. a 6 mm working channel), lumen 351, of endoscope 350. Shafts 311a and 311b may be been inserted over a guidewire, such as guidewire 371 shown exiting distal end 312. Device 301 further includes two expandable tissue treatment elements, expandable abrasive element 322a, and expandable energy delivery element 322b, mounted to shafts 311a and 311b, respectively. Shafts 311a and 311b may include one or more lumens passing therethrough, and may comprise wires or optical fibers for transfer of data and/or energy.

Endoscope 350 may be a standard endoscope, such as a standard gastrointestinal endoscope, or a customized endoscope, such as an endoscope including sensor 353 configured to provide information related to the tissue treatment of the present inventive concepts. Sensor 353 and the other sensors of system 300 may be a sensor selected from the group consisting of: heat sensors such as thermocouples; impedance sensors such as tissue impedance sensors; pressure sensors; blood sensors; optical sensors such as light sensors; sound sensors such as ultrasound sensors; electromagnetic sensors such as electromagnetic field sensors; and combinations of these. Sensor 353 may be configured to provide information to one or more components of system 300, such as to monitor the treatment of target tissue 10 and/or to treat target tissue 10 in a closed loop fashion. Endoscope 350 may include camera 352, such as a visible light, ultrasound and/or other visualization device used by the operator of 300 prior to, during or after the treatment of target tissue 10, such as during insertion or removal of endoscope 350 and/or shafts 311a and 311b. Camera 352 may provide direct visualization of internal body spaces and tissue, such as the internal organs of the gastrointestinal tract. Endoscope 350 may be coupled with or otherwise include a guidewire, such as to allow insertion of endoscope 350 into the jejunum.

System 300 may be configured to perform insufflation of the body lumen. The body lumen may be pressurized, such as by using one or more standard insufflation techniques and/or a technique as described in reference to FIGS. 5, 8A and 8B herebelow. Insufflation fluid may be introduced through lumen 354 of endoscope 350. Lumen 354 travels proximally and connects to a source of insufflation liquid or gas, not shown, but typically a source of air, $CO_2$ and/or water. Alternatively or additionally, insufflation fluid may be delivered by device 301, such as through shaft 311a and/or 311b, or through a port in treatment element 322a and/or 322b, ports not shown but fluidly attached to a source of insufflation liquid or gas, also not shown. Alternatively or additionally, a separate device, configured to be inserted through endoscope 350 or to be positioned alongside endoscope 350, may have one or more lumens configured to deliver the insufflation fluid. System 300 may include one or more occlusive elements or devices, such as expandable treatment element 322a or another expandable device, not shown but configured to radially expand such as to fully or partially occlude the body lumen, such that insufflation pressure can be achieved and/or maintained over time (e.g. reduce or prevent undesired migration of insufflation fluid). The one or more occlusive elements or devices may be positioned proximal to and/or distal to the luminal segment to be insufflated.

The treatment elements of the present inventive concepts, such as treatment elements 322a and/or 322b of FIG. 4, may have a fixed diameter or they may be expandable. Expandable elements may comprise inflatable balloons, expandable cages, radially deployable arms, and the like. Treatment elements may include an energy delivery element or arrays of elements, such as an array of electrodes mounted to a deployable cage. Energy delivery elements may be configured to deliver one or more different forms of energy as has been described above in reference to FIG. 3. Energy may be delivered in constant or varied magnitudes or other energy levels. Energy may be continuous or pulsed, and may be delivered in a closed-loop fashion. Energy delivery may be varied from a first tissue location to a second location, such as a decrease in energy from a first treated location to a second treated location when the second treated location is thinner than the first treated location. Alternatively or additionally, energy delivery may be varied during a single application to a single tissue location, such as by adjusting the amount of energy delivered, or by moving a portion of the energy delivery element as is described in detail in reference to FIGS. 8A and 8B herebelow.

Treatment elements 322a and/or 322b may be configured to cause the complete or partial destruction of the target tissue, such as the complete or partial destruction of the duodenal mucosa. Treatment elements 322a and/or 322b may be configured to remove previously treated and/or untreated tissue. Pressure maintained within treatment elements 322a and/or 322b can be set and/or varied to adjust the treatment being performed such as to: adjust the depth of treatment; adjust the force applied by a mechanical abrasion device; adjust the amount of energy applied during RF energy delivery (e.g. by changing tissue impedance or electrode contact); and combinations of these.

Treatment elements 322a and 322b may include sensors 316a and 316b, respectively. Sensors 316a and 316b may each be one or more sensors as described hereabove. Sensor 316a may be a sensor configured to provide information related to the tissue treatment performed by abrasive element 322a, such as a visualization sensor mounted to abrasive element 322a that is configured to differentiate tissue types that are proximate abrasive element 322a, such as to differentiate mucosal and submucosal tissue. Sensor 316b may be a sensor configured to provide information related to the tissue treatment performed by energy delivery element 322b, such as a temperature sensor mounted to energy delivery element 322b and configured to monitor the temperature of energy delivery element 322b and/or tissue proximate energy delivery element 322b.

Energy Delivery Unit (EDU) 330 may be configured to deliver one or more forms of energy as have been described above in reference to FIG. 3. In one embodiment, EDU 330 is configured to deliver at least radiofrequency (RF) energy, and system 300 includes ground pad 332 configured to be attached to the patient (e.g. on the back of the patient), such that RF energy can be delivered in monopolar delivery mode. Alternatively or additionally, EDU 330 may be configured to deliver energy in a bipolar RF mode, such as when element 322b is configured to deliver RF energy and/or system 300 includes a second energy delivery element, not shown but typically including one or more electrodes or electrically conductive surfaces.

System 300 may include controller 360 which typically includes a graphical user interface, not shown but configured to allow one or more operators of system 300 to perform one or more functions such as entering of one or more system input parameters and visualizing and/or recording of one or more system output parameters. Typical system input parameters include but are not limited to: type of energy to be delivered such as RF energy, thermal energy and/or mechanical energy; quantity of energy to be delivered such as a cumulative number of joules of energy to be delivered or peak amount of energy to be delivered; types and levels of combinations of energies to be delivered; energy delivery duration; pulse width modulation percentage of energy delivered; number of reciprocating motions for an abrasive device to transverse; temperature for a treatment element such as target temperature or maximum temperature; insufflation pressure; insufflation duration; and combinations of these. System input parameters may include information based on patient anatomy or conditions such as pre-procedural or peri-procedural parameters selected from the group consisting of: mucosal density and/or thickness; mucosal "lift" off of submucosa after a submucosal injection; longitudinal location of target tissue within the GI tract; and combinations of these. Typical system output parameters include but are not limited to: temperature information such as tissue and/or treatment element temperature information; pressure information such as balloon pressure information or insufflation pressure information; force information such as level of force applied to tissue information; patient information such as patient physiologic information recorded by one or more sensors; and combinations of these.

Controller 360 and/or one or more other components of system 300 may include an electronics module, such as an electronics module including a processor, memory, software, and the like. Controller 360 is typically configured to allow an operator to initiate, modify and cease treatment of tissue by the various components of system 300, such as by controller energy delivery unit 330. Controller 360 may be configured to adjust the pressure within expandable treatment elements 322a and/or 322b, such as to vary the abrasion force and/or energy, respectively, applied to the target tissue. Controller 360 may be configured to initiate insufflation and/or to adjust insufflation pressure. Controller 360 may be configured to deliver energy (e.g. from EDU 330) or other tissue treatment in a closed-loop fashion, such as by modifying one or more tissue treatment parameters based on signals from one or more sensors of system 300. Controller 360 may be programmable such as to allow an operator to store predetermined system settings for future use.

Controller 360 and EDU 330 may be configured to deliver energy in constant, varied, continuous and discontinuous energy delivery profiles. Pulse width modulation and/or time division multiplexing (TDM) may be incorporated to achieve precision of energy delivery, such as to ensure ablation of target tissue while leaving non-target tissue intact.

System 300 may include a mechanism configured to apply motion to treatment elements 322a and/or 322b, such as motion transfer element 335. Motion transfer element 335 may be configured to rotate and/or axially translate shafts 311a and/or 311b such that treatment elements 322a and/or 322b, respectively, are rotated and/or translated. Motion transfer element 335 may be configured to rotate treatment elements 322a and 322b independently or in unison. Motion transfer element 335 may include one or more rotational or linear drive assemblies, such as those including rotational motors, magnetic and other linear actuators, and the like which are operably connected to shaft 311a and/or 311b. Shafts 311a and/or 311b are constructed with sufficient column strength and/or torque transfer properties to sufficiently rotate and/or translate treatment elements 322a and/or 322b, respectively, during associated tissue treatment. Motion transfer element 335 may be in communication with controller 360, such as to activate, adjust and/or otherwise control motion transfer element 335 and thus the motion of abrasion element 322a and/or energy delivery element 322b. Motion transfer element 335 may be manually driven and/or automatically (e.g. motor) driven.

In one embodiment, after placing abrasive element 322a in a distal position in the intestine, abrasive element 322a is rotated at a constant rate and pulled back (i.e. moved proximally) at a constant rate for a fixed distance, forming a spiral path including a substantially uniform amount of tissue abraded from the intestinal wall. Alternately, abrasive element 322a may be oscillated rotationally, longitudinally, or both, for a fixed duration, so that the abrasive element 322a repeatedly abrades a defined portion of the intestinal wall for a fixed treatment period (e.g., time, pressure, etc). In another embodiment, controller 360 comprises a simple handle which the user moves back and forth repeatedly to affect a back and forth abrading of a luminal wall. Controller 360 may include both manual and motorized features, enabling the user to apply motorized treatments periods (e.g. at a fixed time and/or pressure) for some portion of the intestine and apply manual treatment periods for other intestinal areas. Controller 360 may be programmable so that, for example circumferential abrasion is achieved in certain portions of the intestine, and only a portion of the circumference is abraded in other portions of the intestine, such as locations at the Ampulla of Vater.

Controller 360 may be configured to control energy delivery, such as energy delivery to energy delivery element 322b. For example, if ablative element 322b is an RF electrode array, and energy delivery unit 330 comprises an RF generator, controller 360 may be programmed to provide a specific amount of RF energy for a defined period of time. In another example, if energy delivery element 322*b* is a heated saline balloon, then controller 360 can be configured to provide and withdraw heated saline to energy delivery element 322*b*, such as through an energy transfer tube not shown, at a desired temperature and for a desired time period. Controller 360 may be configured for manual control, so that the operator first initiates the energy delivery, then allows the energy delivery element 322*b* to ablate the tissue for some time period, after which the operator terminates the energy delivery.

System 300 may further include one or more imaging devices, such as imaging device 370. Imaging device 370 may be configured to be inserted into the patient and may comprise a visual light camera; an ultrasound imager; an optical coherence domain reflectometry (OCDR) imager; and/or an optical coherence tomography (OCT) imager, such as when integral to, attached to, contained within and/or proximate to shaft 311*a* and/or 311*b*. Imaging device 370 may be inserted through a separate working channel of endoscope 350, lumen not shown. In one embodiment, imaging device 370 is an ultrasound transducer connected to a shaft, not shown but surrounded by shaft 311*a* and typically rotated and/or translated to create a multi-dimensional image of the area surrounding imaging device 370. Alternatively or additionally, imaging device 370 may be external to the patient, such as an imaging device selected from the group consisting of: an X-ray; a fluoroscope; an ultrasound image; an MRI; a PET Scanner; and combinations of these.

System 300 may further include protective cap 380, configured to be positioned proximate tissue to prevent damage to certain tissue during energy delivery or other tissue treatment event. Protective cap 380 may be fitted with endoscope 350 or another elongate device such that cap 380 can be placed over and then positioned to protect the Ampulla of Vater, as is described in detail herebelow in reference to FIG. 18. In a typical embodiment, protective cap 380 is removed within 24 hours of placement, such as by being removed during the procedure after treatment of the target tissue.

System 300 may further include a tissue expanding device 390, configured to expand the target tissue area, such as tissue expanding device 390 of FIG. 13 described in detail herebelow. Tissue expansion can greatly alleviate the need for precision of treatment, such as precision of energy delivery, due to the increased size (e.g. increased depth) of the target and associated safety zone of tissue to which treatment causes no significant adverse event (e.g. the submucosal layer of a mucosal layer ablation).

System 300 may further include one or more pharmaceutical or other agents 500, such as an agent configured for systemic and/or local delivery to a patient. These agents may be delivered, pre-procedurally, peri-procedurally and/or post-procedurally. The agents may be configured to improve healing, such as agents selected from the group consisting of: antibiotics, steroids, mucosal cytoprotective agents such as sucralfate, proton pump inhibitors or other acid blocking drugs; and combinations of these. Alternative or in addition to these agents, pre-procedural and/or post-procedural diets may be employed. Pre-procedural diets may include food intake that is low in carbohydrates and/or low in calories. Post-procedural diets may include food intake that comprise a total liquid diet or a diet that is low in calories and/or low in carbohydrates.

In a typical embodiment, system 300 does not include a chronically implanted component or device, only body inserted devices that are removed at the end of the clinical procedure or shortly thereafter, such as devices removed within 8 hours of insertion, within 24 hours of insertion and/or within one week of insertion. In an alternative embodiment, implant 510 may be included. Implant 510 may comprise one or more of: a stent; a sleeve; and a drug delivery device such as a coated stent, a coated sleeve and/or an implanted pump.

Each of the components of system 300 may be removably attached to another component, particularly controller 360, energy delivery unit 330, motion transfer element 335, ground pad 332 and endoscope 350 and elongate device 301.

Figure 5:
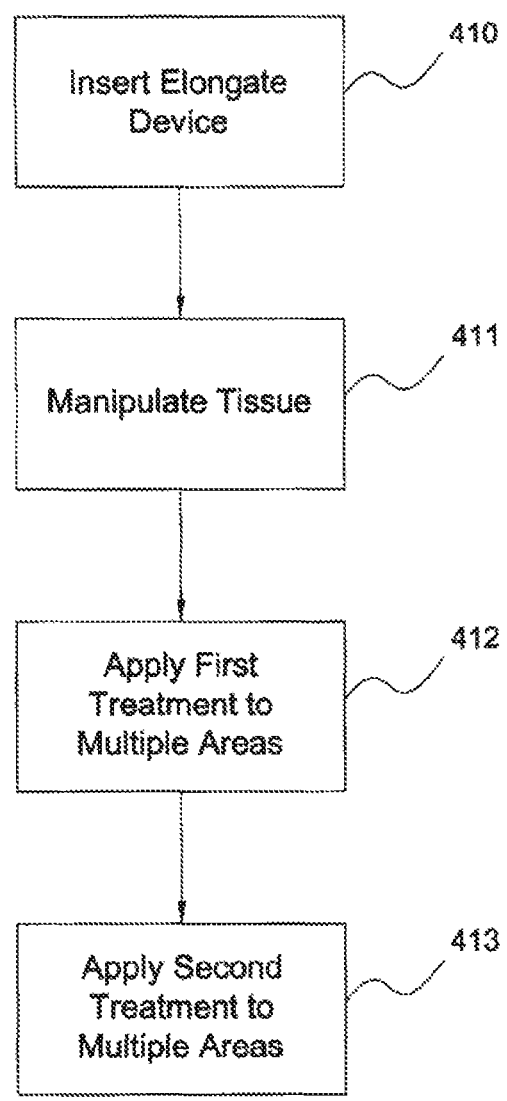
FIG. 5 illustrates a flow chart of a method for treating tissue, according to embodiments of the present inventive concepts.

FIG. 5 illustrates a flow chart of a method for treating tissue, according to embodiments of the present inventive concepts. STEPs 410 through 413 describe a method of treating target tissue, such as duodenal tissue or other tissue, to treat a patient disease or disorder such as diabetes. In this particular embodiment, the target tissue comprises multiple tissue portions. The multiple tissue portions may comprise multiple adjacent tissue areas, such as multiple contiguous circumferential segments of the duodenum or other gastrointestinal lumen. A first treatment is applied to a first set of tissue portions, and subsequently a second treatment is applied to a second set of tissue portions. The first set of tissue portions typically includes all or some of the second set of tissue portions. The first and/or second treatments may treat one or more tissue areas that overlap each other (e.g. the borders of the tissue portions overlap preventing untreated tissue locations between treated areas).

In STEP 410, an elongate device is inserted into the body of a patient, such as through a lumen of a previously inserted device such as through the lumen of an endoscope. The elongate device may be inserted such as to treat duodenal tissue, such as with access through the stomach via the esophagus; through the jejunum; through the stomach via a laparoscopic tool; surgically through the side wall of the intestine; through the stomach and jejunum, simultaneously or sequentially, from each end, in the same or different procedures; and combinations of these. The elongate device may be an endoscope; may be inserted through an endoscope; may be inserted through a laparoscopic port; may be inserted through a gastric port or tube; and combinations of these.

In STEP 411, the target tissue and/or tissue proximate the target tissue, such as tissue on either side of the target tissue, may be positioned, tensioned or otherwise manipulated, such as by the elongate device placed in STEP 410. Manipulating includes but is not limited to: axial straightening such as straightening of the duodenum or other intestinal tissue; tensioning such as axial and/or radial tensioning; thickness expansion such as expansion of the submucosa of the intestine with an injected fluid (e.g. injected liquid or gas); applying an axial force to tissue; applying opposing axial forces to tissue; applying a radial force to tissue; compressing tissue such as compressing the villi of the duodenum; inducing localized edema or angioedema; expanding the duodenum radially such as to reduce the protrusions of plicae circulares and prevent or reduce under treatment of plicae due to folding over of those plicae by a treatment element; and combinations of these. Manipulation of tissue may be performed to cause one or more of the following to occur: straightening of a length of tubular tissue; compressing of tissue layers; compression of projections into the lumen of tubular tissue (e.g. compression of villi into the intestine); tensioning of tissue; expansion of one or more tissue layers; increasing overall thickness of intestinal wall;

removal of mucus and intestinal contents from the tissue wall; and combinations of these.

Tissue manipulation can be accomplished in various ways. Tissue tensioning can be achieved by application of force upon one or more tissue contacting devices, such as one or more expandable elements as is described in detail in reference to FIGS. 8A and 8B. In one embodiment, opposing forces are applied to two tissue manipulators positioned within a body lumen, such as within the duodenum or other gastrointestinal lumen. Tissue manipulation can be performed through insufflation, such as when a distal expanding element occludes the body lumen, and insufflation pressure applies straightening and other manipulating forces to the tissue proximal to the expanding element. Insufflation fluid can be introduced by one or more devices, including but not limited to the tissue treatment devices and endoscopes of the present inventive concepts. In one embodiment, a pressure of at least 0.5 cm of $H_2O$ imposed on the internal lumen of the duodenum is employed. In another embodiment, a pressure of less than 15.0 cm of $H_2O$ is imposed on the internal lumen of the duodenum. Tissue manipulation can be performed through the introduction of fluid into tissue, such as the fluid placed via a needle into submucosal tissue, as is described in detail in reference to FIG. 13 hereinbelow.

Insufflation is used to expand the lumen of the gastrointestinal tract, such as to more easily visualize the mucosa, to ease advancement and/or retraction of devices such as endoscopes and treatment devices of the present inventive concepts, and to more easily manipulate and/or treat tissue. Insufflation can be delivered as a fluid, such as air, $CO_2$ and/or water, and may be introduced, removed, and reintroduced, such as after repositioning one or more devices. There are plicae and other folds of tissue within a gastrointestinal lumen that may complicate the apposition of one or more treatment elements to the target tissue. Insufflation can reduce or eliminate the majority of these tissue folds such as via distension of the mucosal lining. Insufflation can also be used to elongate and/or straighten a portion of a body lumen such as the duodenum.

In STEP 412, a first treatment is applied to multiple tissue portions sequentially. The first treatment may be applied by the elongate device introduced in STEP 410, or another inserted device. The first treatment may include one or more treatments such as application of energy such as RF energy, thermal energy, or another tissue treatment.

In STEP 413, a second treatment is applied to multiple tissue portions sequentially, typically the same tissue portions treated in STEP 412. The second treatment may be applied by the device used to manipulate tissue in STEP 411, the first treatment device of STEP 412, or another treatment device. The second treatment may be similar or dissimilar to the first treatment. Differences include but are not limited to: device used to deliver the treatment; type of energy delivered; quantity or level of energy delivered such as power level, temperature level, duration of energy application; types and levels of combinations of energies delivered; and combinations of these. Prior to or during STEP 413, a second tissue manipulating step may be performed, such as a different tissue manipulation in the same tissue area or a similar or dissimilar tissue manipulation in a different tissue area. In some embodiments, combinations of tissue ablation and tissue abrasion are employed. Abrasion may follow ablation, such as to debride ablated tissue. Abrasion of villi may be followed by ablation of remaining mucosa. Multiple applications of abrasion and/or ablation may be employed, in one or more tissue portions, until treatment of the complete target area is complete.

After completion of STEP 413, the tissue treatment may be completed or additional tissue treatments may be performed. The tissue treatments of STEPs 412 and/or 413 may be repeated, or a different tissue treatment may be performed. Prior to and/or during any additional tissue treatment steps, another tissue manipulating STEP 411 may be performed.

One or more additional clinical procedures may be included in the methods of the present inventive concepts. Typical adjunctive and/or supportive procedures include but are not limited to: mucosal transplantation; natural orifice surgery; mucosal scarring procedure; antibiotic therapy; drug therapies configured to prevent or promote re-growth of mucosal tissue; implants such as physical barriers configured to cause scarring or to limit absorption through mucosal tissue; therapies to treat obesity and/or diabetes; diet; exercise; and combinations of these.

STEPs 412 and 413 are typically performed in a single clinical procedure, such as during a single sterile procedure. Alternatively or additionally, repeat treatments may be performed days, weeks or months later. In one embodiment, the target tissue treated includes the stem cells at the base of the crypts of the duodenal mucosa. In this embodiment, the mucosa does not re-grow for an extended period of time, and secondary procedures, similarly treating these stem cells, may be repeated as frequently as necessary, such as to provide a durable effect on a diabetic patient.

Figure 6:
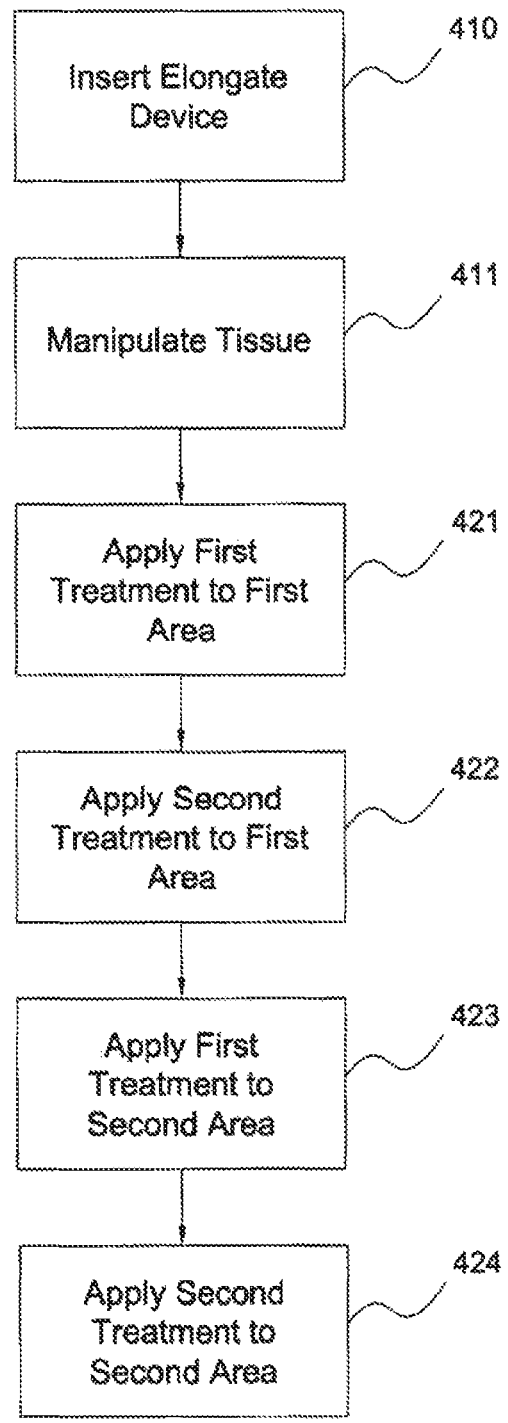
FIG. 6 illustrates a flow chart of a method for treating tissue, according to embodiments of the present inventive concepts.

FIG. 6 illustrates a flow chart of a method for treating tissue, according to embodiments of the present inventive concepts. STEPs 410 through 424 describe a method of treating target tissue, such as duodenal tissue or other tissue, to treat a patient disease or disorder such as diabetes. The target tissue comprises multiple tissue portions, which are each treated by a first treatment followed by a second treatment, such as treatment of a first segment of duodenum followed by a treatment of a second segment of duodenum. The multiple tissue portions may comprise multiple adjacent tissue areas, such as multiple contiguous circumferential segments of the duodenum. The first and/or second treatments may treat one or more tissue areas that overlap each other (e.g. the borders of the tissue portions overlap preventing untreated tissue locations between treated areas). Treatment of multiple areas may be accomplished by repositioning of one or more treatment elements, such as repositioning of one or more energy delivering expandable structures such as balloons. Alternatively or additionally, an expandable device may be positioned and a treatment element axially translated to treat multiple areas, continuously or segmentally. First and second treatments may include treatment of two full circumferential segments of a conduit. Alternatively, first and second treatments may includes a first partial circumferential segments (e.g. less than 360° of a conduit segment) followed by a second partial circumferential segment, such as the remaining circumferential portion of the conduit.

In STEP 410, an elongate device is inserted into the body of a patient, such a through a lumen of a previously inserted device such as through the lumen of an endoscope.

In STEP 411, the target tissue and/or tissue proximate the target tissue, such as tissue on either side of the target tissue, may be manipulated, as has been described in reference to STEP 411 in reference to FIG. 5 hereabove.

In STEP 421, a first treatment is applied to a first tissue portion. The first treatment may be applied by the elongate device introduced in STEP 410, or another inserted device. The first treatment may include one or more treatments such as application of energy such as RF energy or another treatment described in this application.

In STEP 422, a second treatment is applied to the first tissue portion. The second treatment may be applied by the device used to manipulate tissue in STEP 411, the first treatment device of STEP 421, or another treatment device. The second treatment may be similar or dissimilar to the first treatment. Differences include but are not limited to: device used to deliver the treatment; type of energy delivered; value of an energy delivery amount such as energy level, temperature level, and duration of application; combinations of energies delivered; and combinations of these.

In STEP 423, a first treatment is applied to a second tissue portion. This treatment is typically similar to the treatment of STEP 421, but may be varied such as varied energy delivery due to the first tissue portion and the second tissue portion having different tissue characteristics such as thickness of tissue to be treated.

In STEP 424, the second treatment is applied to the second tissue portion. This treatment is typically similar to the treatment of STEP 422, but may be varied such as varied energy delivery due to the first tissue portion and the second tissue portion having different tissue characteristics such as thickness of tissue to be treated.

Numerous combinations and varied orders of tissue treatment modalities can be employed without departing from the spirit and scope of the present inventive concepts. Treatment modalities include but are not limited to: type of energy used; depth of treatment; tissue surface area treated including length and/or width of tissue surface area; duration of treatment; manipulation of target tissue and tissue proximate target tissue such as via a tensioning device or a submucosal injection as is described in reference to FIG. 13 herebelow; and combinations of these. In one embodiment, a treatment includes: a submucosal injection; inflation of one or more balloons proximal and/or distal to the target tissue area such as to create a relatively fluid-tight seal; an abrasion of tissue; and an ablation of tissue. In another embodiment, a treatment includes: ablation by a hot fluid balloon; ablation by direct contact of a hot fluid with target tissue; an ablation by an RF energy delivery device; and mechanical removal of tissue such as via an abrasion device. In yet another embodiment, one or more tissue manipulation steps (e.g. submucosal injection or target tissue tensioning via one or more balloons) is performed in combination with energy delivery (e.g. ablation with hot fluid or RF energy) combined with mechanical tissue removal (e.g. abrasion). Sequencing between energy delivery and mechanical tissue removal may be repeated, and vice versa. Each of these and other tissue treatment steps may be included in any combination and in any order.

Prior to or during each of STEPs 422, 423 and 424, one or more additional tissue manipulating steps may be performed, such as a different tissue manipulating in the same tissue area or a similar or dissimilar tissue manipulating in a different tissue area.

After completion of STEP 424, the tissue treatment may be completed or additional tissue treatments may be performed. The tissue treatments of STEPs 421 and 422 may be repeated, or a different tissue treatment may be performed. Prior to and/or during any additional tissue treatment steps, another tissue manipulating STEP 411 may be performed.

FIG. 7 illustrates a flow chart of a method for treating tissue, according to embodiments of the present inventive concepts. STEPs 510 through 540 describe a method of treating target tissue, such as duodenal tissue or other tissue, to treat a patient disease or disorder such as diabetes. The target tissue may comprise multiple tissue portions, which are treated by one or more types of tissue treatments configured to treat the target tissue. The method includes monitoring of one or more parameters and adjusting the tissue treatment based on the one or more parameters being between acceptable limits, such as pre-determined limits.

In STEP 510, the treatment of a portion of tissue is initiated. The tissue is typically treated by a device including one or more treatment elements. The treatment elements may deliver energy (e.g. RF or thermal energy) or may be configured to allow an operator to deliver energy (e.g. mechanical energy delivered by a reciprocating abrasive device).

In STEP 520, as treatment continues, one or more parameters are measured and compared to one or more thresholds, such as one or more quantitative values.

If the measured parameters are not within acceptable limits, STEP 525 is performed in which one or more treatment parameters are adjusted. Adjustable treatment parameters include but are not limited to: type of energy to be delivered such as RF energy, thermal energy and/or mechanical energy; quantity of energy to be delivered such as a cumulative number of joules of energy to be delivered or peak amount of energy to be delivered; types and levels of combinations of energies to be delivered; energy delivery duration; pulse width modulation percentage of energy delivered; number of reciprocating motions for an abrasive device to transverse; temperature for a treatment element such as target temperature or maximum temperature; and combinations of these; and combinations of these. After adjustment, the monitoring of STEP 520 continues.

If the measured parameters are within acceptable limits, STEP 530 is performed in which the tissue treatment for the current tissue portion is checked for completion, such as by an algorithm of the system of the present inventive concepts. In one embodiment, the completion check is time or action based. Time-based checks may simply indicate completion after a fixed time period has been reached (e.g. open loop), such as a fixed time period for one or more energy deliveries to treat target tissue. Action-based checks may be selected from the group consisting of: an energy level is achieved; a power level is achieved; a level of energy has been delivered (e.g. a pre-determined number of joules of RF energy); a number of mechanical cycles such as a set of reciprocating motions has been achieved; a tissue change has occurred such as a color change, a texture change or other visual change has occurred; tissue impedance and/or a change is tissue impedance has reached a threshold; a temperature and/or a change is temperature (e.g. a temperature and/or change of tissue temperature) has reached a threshold; blood flow and/or a change in blood flow has reached a threshold; a serum hormone level and/or a change in a serum hormone level has reached a threshold; blood sugar level and/or a change in blood sugar level has reached a threshold; submucosal connective tissue is exposed (e.g. as detected by visual inspection or chemical and/or biological detection mechanisms); and combinations of these. Numerous forms of closed-looped checks may be performed in STEP 520, such as by measuring one or more system or patient parameters with one or more sensors. Sensors may monitor and provide information related to system parameters, such as the sensors listed in reference to FIG. 4 hereabove. Sensors of the present inventive concepts may be placed in one or more locations, typically to be positioned within the body of the patient. Sensors may be positioned within a body lumen such as on a device positioned within the duodenum such that the sensor contacts the duodenal wall. Alternatively or additionally, one or more sensors may be placed within a tissue wall, such as within the submucosal space after a submucosal injection has occurred. Alternatively or additionally, the sensor may be positioned outside of the gastrointestinal tract, such as in the extra-intestinal space or in surrounding structures. In one embodiment, a sensor is positioned in or proximate to the Ampulla of Vater, such as to monitor temperature of the pancreas. In another embodiment, a sensor is positioned to monitor the temperature of a vascular structure such as the inferior vena cava. Sensors may monitor and provide information related to patient parameters, such as parameters selected from the group consisting of: temperature information such as tissue temperature information or treatment element temperature; impedance information such as tissue impedance information; pressure information; blood flow information; blood sugar levels; insulin levels; glucagon levels; GIP, GLP-1, GLP-2 and/or other gastrointestinal hormone levels; and combinations of these. In one embodiment, a heat and/or impedance sensor is included, and sensor information is used to regulate energy delivery such as RF energy delivery.

If treatment of the current tissue portion is complete, STEP 540 is performed where one or more tissue treatment devices are re-positioned to treat an additional tissue portion of the target tissue, after which STEP 510 is repeated. If the entire tissue portion has been treated, the tissue treatment is complete and the one or more devices used may be removed from the patient or used to perform a secondary procedure.

Prior to initiating treatment in step 510, one or more parameters may be measured, such as one or more system or patient parameters. In one embodiment, a tissue parameter is measured, such as tissue thickness measured with a visualization sensor or device such as a visualization sensor or device using ultrasound, optical coherence domain reflectometry (OCDR) and/or optical coherence tomography (OCT). Based on the results of the pre-treatment parameter measurement, one or more treatments may be adjusted, such as an increase or decrease in energy to be delivered based on measured tissue thickness at a particular tissue location. The one or more parameters measured prior to tissue treatment may by measured again (e.g. continuously or intermittently monitored in real time), prior to or during one or more subsequent tissue treatment steps. In another embodiment, a parameter (e.g. a tissue parameter measured by an imaging sensor or device) is measured to select a treatment modality. Typical treatment modalities include but are not limited to: energy type to be delivered; selection of a tissue treatment parameter to allow re-growth or prevent re-growth of one or more cell types.

Treatment may be conducted and monitored until a substantial amount of the mucosal cells or cells from the crypts and villi producing hormones are rendered non-functional. Treatment monitoring may include monitoring the depth of penetration of treatment, such as during RF energy delivery or other ablative tissue treatment. In one aspect of the inventive concepts, the cells rendered non-functional are unable to reproduce, that is, the re-growth and regeneration of the cells rendered non-functional is substantially eliminated. The cells that become non-functional may include a fraction of the mucosal cells, such as less than 100% of the mucosal cells. In another embodiment, the cells that become non-functional include all of the mucosal cells (i.e. 100% of the mucosal cells). In this embodiment, a fraction of the submucosal cells may be targeted (i.e. made non-functional) to assure all of the mucosal cells are impacted. In another embodiment, a tissue treatment, for example, an ablative step may target stem cells of the base of the crypts. The removal of these particular stem cells may prevent re-growth of the stem cells of the mucosa. Multiple ablations, of similar or dissimilar energies deliveries, may be performed. In yet another embodiment, the tissue treatment may extend to the level of the stem cells by ablating the surface mucosa and intestinal villi, shaving or mechanically disrupting the tissue to eliminate the killed cells, and then re-ablating the mucosal surface to target the stem cells at the base of the crypts. Detailed descriptions of target tissue and non-target tissue are provided hereabove in reference to FIG. 3A.

Monitoring of one or more system or patient parameters, such as tissue thickness and/or depth of penetration of tissue treatment, may be used to reduce or minimize formation of strictures, bleeding, scarring and/or perforation. In one embodiment, the tissue treatment may be stopped or otherwise modified if an ulcer, cancer and/or thin walled tissue location is detected. Depth of penetration of tissue treatment may be monitored by one or more system sensors, such as a visual sensor such as an ultrasound sensor or other cellular structure sensor; an impedance sensor such as a tissue impedance sensor, and/or other sensor from which depth information can be correlated. Depth of penetration may be monitored in real-time, or with minimal delay such as to prevent an undesired clinical events selected from the group consisting of: prevention of undesired strictures or scarring; perforation; bleeding; and combinations of these. The depth of penetration information obtained by the one or more sensors may be used to automatically treat tissue or simply provided to a clinician or other operator of the system for their interpretation and subsequent adjustment of treatment.

Numerous patient and/or system parameters can be measured prior to, during, or after one or more tissue treatment steps, such as by using one or more sensors or sensing devices of the system of the present inventive concepts. Electromyographic sensors may be used, such as to perform electromyography of the muscularis mucosa. A clinician may sense contraction of the muscularized mucosa as a way of achieving proper treatment depth. Depth of penetration may be controlled by measuring the change in impedance to electrical current delivered to tissue. Energy delivery is reduced or stopped when the impedance changes from that which may be expected for the mucosa to that which may be expected for the muscularis mucosa or submucosa. A probe configured to monitor the electrical or contractile activity of the muscularis mucosa may be inserted, such as to assess the influence of energy delivery on muscle function. Quantitative calorimetry may be used to monitor changes in tissue or tissue characteristics, such as to monitor tissue characteristics before, during and/or after tissue treatment as has been described hereabove. One or more sensors or sensing devices may be configured to provide serum analysis, such as hormonal release data or glucose responsiveness data.

One or more visual sensors or devices may be used to measure one or more system or patient parameters. Visual interrogation of the mucosa, such as during ablation, may be used to control depth of energy delivery. Light scattering spectroscopy can be used to perform tissue surface evaluation, such as to identify dysplasia or to evaluate a villi characteristic such as length or color. Since the villi are typically a lighter color than the mucosa, spectroscopy can be used to monitor the progress of treatment (e.g. removal of villi). Characterization of tissue color changes can identify level of desiccation of tissue (e.g. reddening or whitening). Identification and/or quantification of edema; tissue perfusion and/or tissue oxygenation may be monitored using visual sensors or visualization devices. Imaging of the mucosa may be performed to determine the types of enteroendocrine cells present.

Sensors and sensing devices of the present inventive concepts can be positioned at one or more locations internal and/or external to the patient's body. Imaging device can be used to measure numerous parameters, including but not limited to: body temperature; thickness and temperature of tissue; and vascularity within or proximal to target tissue. In one embodiment, an external imaging device is used to detect the "ice ball" found when cryogenic treatment is being formed. Various imaging modalities may be used such as an imaging modality selected from the group consisting of: X-Ray such as fluoroscopy; CT imaging; MRI; Ultrasound imaging; Molecular Imaging; Nuclear Imaging such as Nuclear imaging with or without glucose tolerance testing; OCT; Spectroscopy such as Tera-Hertz spectroscopy; and combinations of these. Imaging devices may be external or they may be placed into the body such as by being inserted through an endoscope such as an endoscope inserted into the gastrointestinal tract; a percutaneous intravascular device; a laparoscopic probe; and combinations of these.

Figure 8A:
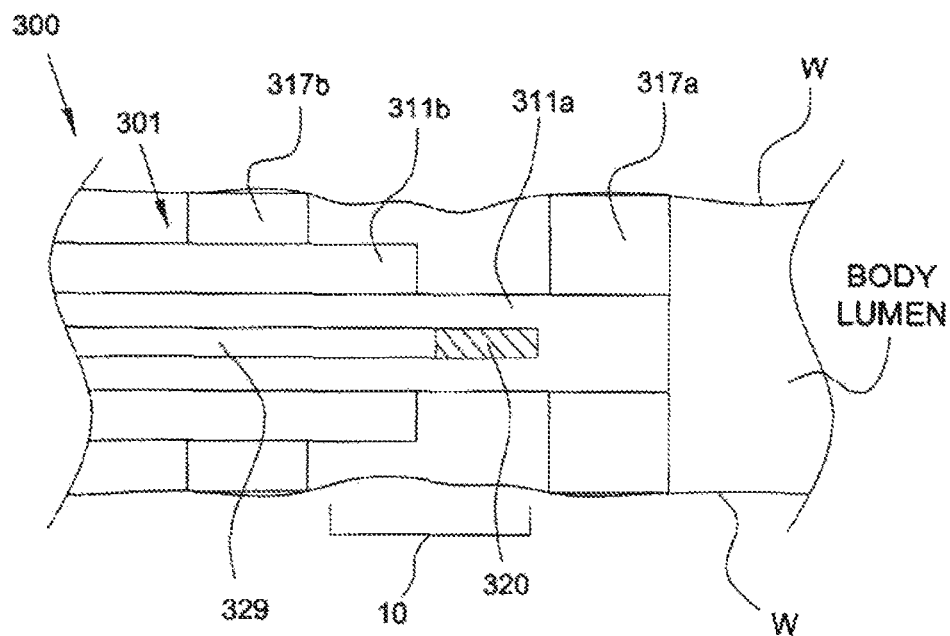
FIGS. 8A and 8B illustrate side sectional views of a distal portion of a tissue treatment system including two tissue manipulating elements, prior to and after applying an axial force to target tissue, respectively, according to embodiments of the present inventive concepts.
Figure 8B:
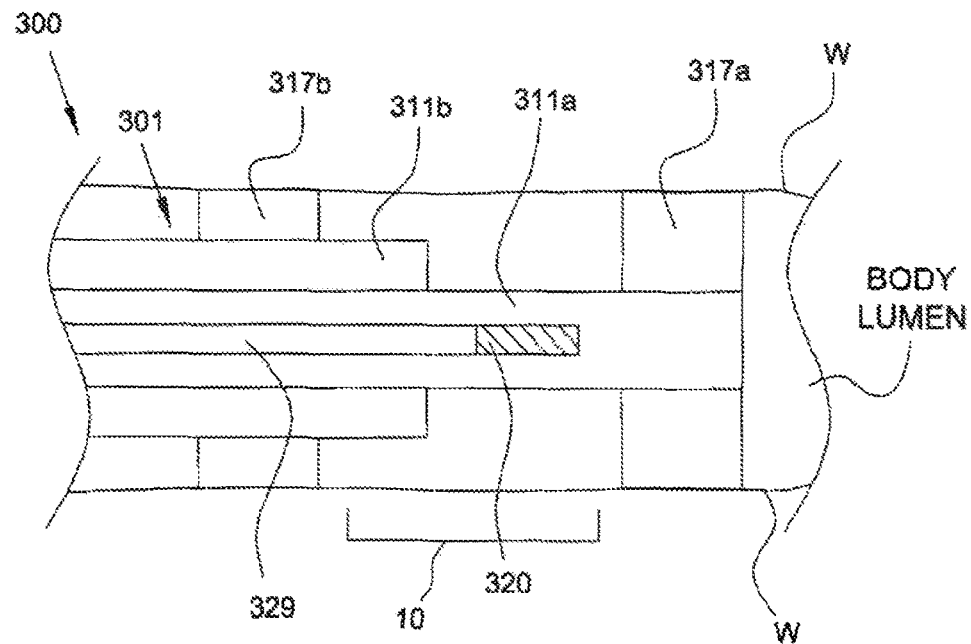

FIGS. 8A and 8B illustrate side sectional views of a distal portion of a tissue treatment system including two tissue manipulating elements, prior to and after applying an axial force to target tissue, respectively, according to embodiments of the present inventive concepts. System 300 is constructed and arranged to treat target tissue 10, including one or more tissue portions as described above in reference to FIG. 3A. System 300 includes device 301 which has been inserted into a body lumen, such as the duodenum, which includes walls W and target tissue 10, typically a 360° segment of intestinal tissue. Device 301 includes shaft 311a which is slidingly received by shaft 311b. Mounted to a distal end of shaft 311a is manipulating element 317a, typically an expandable balloon or expandable cage configured to operably engage luminal wall tissue without penetration. Mounted to a distal end of shaft 311b is manipulating element 317b, also typically an expandable balloon or expandable cage. In an alternative embodiment, engagement by elements 317a and/or 317b is achieved with some penetration of tissue, such as via projections that penetrate to a depth of approximately the mucosa-submucosal interface, such as to ensure adequate grasping force when positioned in the intestine. Shaft 311b may be configured to be slidingly passed through a separate device, such as an endoscope, after which manipulating elements 317a and 317b are expanded to engage luminal walls W.

Positioned within a lumen of shaft 311b is treatment element 320. Treatment element 320 may be configured to apply energy through the walls of shaft 311b into the luminal wall tissue, such as through the application of laser or ultrasound energy. In these directed energy delivering configurations, treatment element 320 may be operably connected to an energy source such as a source of laser or ultrasound energies. Treatment element 320 may include one or more energy delivering or directing elements such as piezo crystals, lenses, mirrors, filters and the like. Alternatively or additionally, treatment element 320 may be configured to radially expand, such as through an opening in shaft 311b (opening not shown), and contact wall W in order to enable treatment of tissue 10 via contact, such as when treatment element 320 contains a hot fluid and or one or more RF energy delivering electrodes. Alternatively or additionally, treatment element 320 may be configured to deliver energy through an opening in shaft 311b, not shown but typically an opening configured to allow a fluid jet to pass therethrough, the fluid jet configured to contact and ablate target tissue 10.

Treatment element 320 is connected to shaft 329, which may comprise an optical fiber, a fluid carrying lumen, and/or one or more electrically conductive wires, and may be configured to rotate such as to cause treatment element 320 to rotate such as when energy is being transmitted to walls W. Alternatively or additionally, shaft 329 may be configured to translate axially, back and forth, such as to move along a tissue area to be treated. Rotation and/or axial translation may be accomplished via a motion transfer element described in reference to FIG. 4 hereabove. Energy may be applied evenly over the target tissue or there may be discontinuous or otherwise uneven energy delivered. Energy may be applied over the full circumference of a lumen, such as along a pre-determined length of the duodenum.

In certain applications, it may be desirable to manipulate target tissue 10 prior to applying energy or other tissue treatment. In a typical embodiment, tissue manipulating elements 317a and 317b are expanded and positioned proximate target tissue 10 as shown in FIG. 8A, such as when elements 317a and 317b are positioned to straighten approximately 2 cm to 5 cm of the duodenum. Walls W may include multiple folds or curved portions as shown in FIG. 8A. In FIG. 8B, shafts 311a has been advanced and/or shaft 311b retracted, such as via one or more controls on the proximal end of shafts 311a and/or 311b, not shown but typically incorporated into a handle on the proximal end of device 301. The advancement of shaft 311a and/or the retraction of shaft 311b causes manipulating element 317a to apply a force to the right of the page as shown and/or manipulating element 317b to apply a force to the left of the page as shown, respectively, to target tissue 10. These forces cause target tissue 10 to be in tension, such as to remove or reduce one or more folds in target tissue 10; to straighten target tissue 10; to position target tissue 10; to support target tissue 10; and combinations of these. Treatment element 320 can be activated prior to, during, or after application of the tensioning (i.e. axial) forces by manipulating elements 317a and/or 317b. Alternatively or additionally, an insufflation fluid can be introduced, proximal to manipulating element 317a (e.g. between elements 317a and 317b which form a relative seal with the luminal wall), causing the luminal wall tissue to radially expand, straighten and/or otherwise be manipulated due to the increased intraluminal pressure.

Treatment of target tissue 10 may include multiple tissue manipulating steps, such as when target tissue 10 is longer than that shown in FIGS. 8A and 8B. In these embodiments, manipulating elements 317a and 317b may apply a force to a first tissue segment, after which they are radially compacted, advanced, and radially expanded such as to apply a force to a second tissue segment. Tissue treatment is typically performed after each tensioning by manipulating elements 317a and 317b, and may be repeated for multiple tissue segments. In certain embodiments, after a sequence of advancing of shafts 311a and 311b, a sequence of retractions is performed, also operating manipulators 317a and 317b to tension tissue segments and activating treatment element 320 to treat these tissue segments.

The systems of the present inventive concepts may treat tissue in a single step or multiple steps. Devices including tissue treatment elements may be positioned a single time for a single treatment, or repositioned multiple times for multiple treatments. Devices including tissue manipulating elements may have one or more tissue manipulating elements positioned a single time, or multiple times. Tissue manipulations may be performed a single time, or multiple times. Energy delivery or other tissue treatment may remain relatively constant through a tissue treatment or over multiple treatments. Alternatively, energy delivery may be varied through a tissue treatment and/or over multiple treatments.

In one embodiment, the tissue manipulating elements 317a and 317b of FIGS. 8A and 8B are positioned a single time in a single location, after which energy is applied by tissue treatment element 320. In this embodiment, energy may be applied without moving tissue treatment element 320 (e.g. in a single energy delivery application or in multiple applications at the same location). The single step delivery may require a large amount of energy to be delivered, such as by tissue treatment elements configured to deliver cryogenic energy; thermal energy such as hot fluid energy; RF energy such as RF energy delivered through multiple electrode arrays. Alternatively, tissue treatment element 320 may be rotated and/or translated back and forth, still without repositioning manipulating elements 317a and 317b (i.e. delivering energy to tissue between elements 317a and 317b). In a different embodiment, tissue manipulating elements 317a and 317b are positioned in multiple locations, and tissue treatment element 320 may deliver a single position energy delivery or multiple position energy delivery accomplished with rotation and/or translation. During movement of treatment element 320, energy or other treatment parameters may be varied or remain constant.

Movement of treatment element 320 combined with modification of energy delivery may be used to achieve one or more of: vary depth of treatment and/or maintain depth of treatment; minimize peak energy levels that need to be delivered to properly treat the target tissue; monitor previously treated tissue for potential re-treatment or modified re-treatment; monitor tissue to be treated to set treatment parameter such as energy level; overlap tissue treatment areas; and combinations of these.

Tissue manipulating elements 317a and/or 317b may be of numerous forms including but not limited to: inflatable balloons; expandable cages; deployable arms such as radially deployable arms; and combinations of these. Tissue manipulating elements 317a and/or 317b may be configured to occlude or partially occlude a lumen such as the intestine, such as during an insufflation procedure. Tissue manipulating elements 317a and/or 317b may be further configured to treat tissue, such as to complement or replace tissue treatment element 320.

In one embodiment, tissue manipulating elements 317a and 317b are balloons or other radially expandable structures (e.g. expandable cages) configured to be pressurized to a level sufficient to exert a traction force on an intestinal wall, such as the wall of the duodenum. Alternatively or additionally, manipulating elements 317a and 317b may be balloons or other occlusive structures configured to allow insufflation of a luminal volume between elements 317a and 317b. In a typical embodiment, manipulating elements 317a and 317b are balloons of approximately 2 inches to 4 inches in length, and manipulated (e.g. pulled apart longitudinally) to position target tissue in a laminar and/or uniform working surface configuration.

In an alternative embodiment, corkscrew stretching may be employed. This stretching may involve an enteroscopy system, such as a spiral enteroscopy system that is rotated into position. These systems can be used that to re-shape target tissue such as the duodenum, such as when the ablation or other target tissue treatment devices advance or retract along the duodenum.

Figure 9:
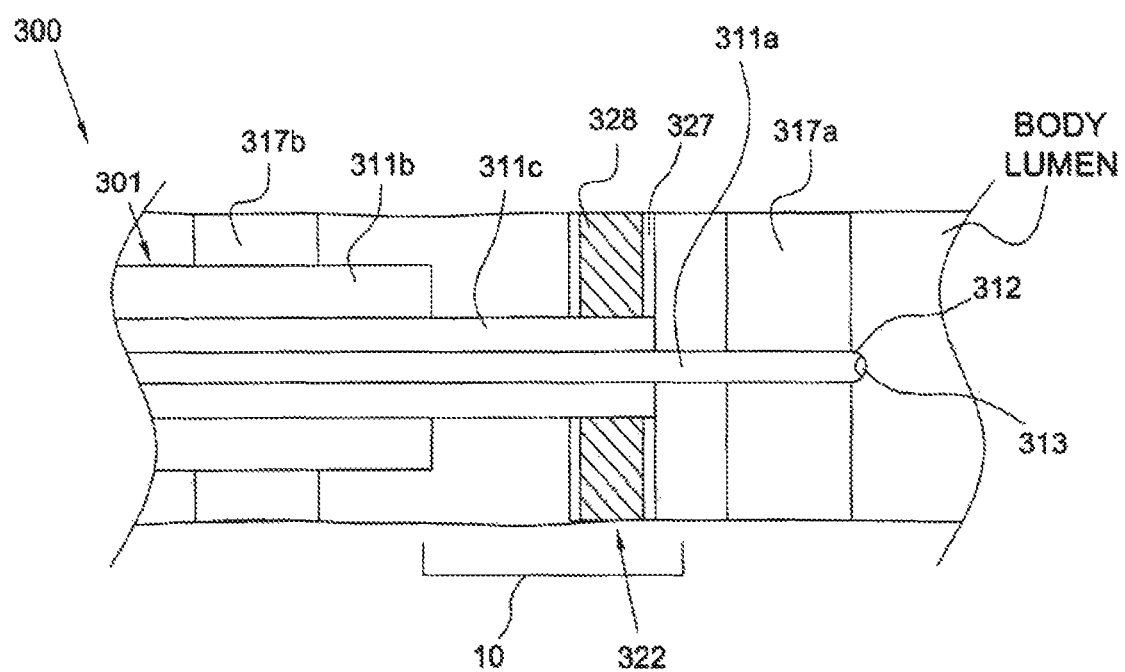
FIG. 9 illustrates a side sectional view of a distal portion of a tissue treatment system including an expandable treatment element and two tissue manipulating elements, according to embodiments of the present inventive concepts.

FIG. 9 illustrates a side sectional view of a distal portion of a tissue treatment system including an expandable treatment element and two tissue manipulating elements, according to embodiments of the present inventive concepts. System 300 is constructed and arranged to treat target tissue 10, including one or more tissue portions as described above in reference to FIG. 3A. System 300 includes device 301 which has been inserted into a body lumen, such as the duodenum or other gastrointestinal lumen, which includes walls W and target tissue 10, typically a 360° segment of intestinal tissue. Device 301 includes shaft 311a which is slidingly received by shaft 311c. Shaft 311c is slidingly received by shaft 311b. Shafts 311a and 311b include manipulating elements 317a and 317b, respectively, of similar construction and arrangement as manipulating elements 317a and 317b of FIGS. 8A and 8B. Shaft 311b may be configured to be slidingly passed through a separate device, such as an endoscope, after which manipulating elements 317a and 317b are expanded to engage luminal walls W. Shaft 311a may include a lumen 313, such as a guidewire lumen, which exits shaft 311a at distal end 312.

Mounted to shaft 311c is ablation element 322 which includes expandable element 327, typically a balloon such as a conformal or non-conformal balloon configured to operably expand to contact, compress and/or otherwise engage luminal wall tissue W. Mounted to expandable element 327 is electrode 328, typically a flexible conductive strip, such as a platinum iridium strip adhesively attached to expandable element 327. Electrode 328 may be attached to an energy delivery unit, not shown, but typically configured similar to EDU 330 of FIG. 5 described hereabove, such as via one or more wires, not shown. Electrode 328 may be configured to deliver monopolar RF energy, such as to a ground pad electrode. Electrode 328 may be configured to deliver bipolar RF energy, such as when device 301 includes a separate electrode, not shown, or when electrode 328 comprises multiple segmented electrodes along the circumferential surface of expandable element 327. System 300 may include an electrically and/or thermally conductive gel, not shown but configured to energy delivery and/or compensate for any non-uniform surfaces such as the crenulations and intestinal villi of the duodenum. Alternatively, light energy may be delivered through expandable element 327. In this embodiment, an optically transmissive gel may be used to improve coupling between element 327 and target tissue.

Expandable element 327 may be configured to apply pressure to the luminal wall W such that sufficient and uniform contact between electrode 328 and the target tissue 10 is present. Application of pressure may be performed to "squeeze out" blood, thus reducing the heat sinking effect of the flowing bodily fluid within or proximate to the tissue to be treated. Applied pressure may also thin (e.g. compress) the tissue wall to be treated, such that the radiative transfer of applied energy is improved and thermal conduction reaches into deeper layers of tissue.

Expandable element 327 and electrode 328 are configured such that multiple energy deliveries may be performed to treat target tissue 10. After a first energy delivery is performed and prior to a second energy delivery, one or more manipulations may be performed such as: rotating electrode 328; advancing or retracting electrode 328; advancing or retracting manipulating elements 317a and/or 317b; and combinations of these. Multiple energy or other tissue treatments are performed until target tissue 10 is sufficiently treated, such as is described in reference to FIGS. 5, 6 and/or 7 hereabove.

In certain applications, it may be desirable to manipulate target tissue 10 prior to applying energy or other tissue treatment, such as has been described in detail hereabove in reference to FIGS. 8A and 8B. Treatment of target tissue 10 may include multiple tissue manipulating steps, such as when target tissue 10 is longer than that shown in FIG. 9. In these embodiments, manipulating elements 317a and 317b may apply a force to a first tissue segment, after which they are radially compacted, advanced, and radially expanded such as to apply a force to a second tissue segment. Tissue treatment is typically performed after each tensioning by manipulating elements 317a and 317b, and may be repeated for multiple tissue segments. In certain embodiments, after a sequence of advancing of shafts 311a and 311b, a sequence of retractions is performed, also operating manipulators 317a and 317b to tension tissue segments and activating treatment element 320 to treat these tissue segments.

Energy delivery steps described in reference to system 300 of FIGS. 8A and 8B hereabove may be performed using system 300 of FIG. 9, where tissue manipulating elements 317a and 317b of FIG. 9 may be placed a single time or multiple times. Expandable element 327 and electrode 328 may be positioned for single or multiple energy deliveries, with or without the repositioning of manipulating elements 317a and 317b. During any movement of treatment element 320, energy or other treatment parameters may be varied or remain constant. Movement of treatment element 320 combined with modification of energy delivery may be used in a similar fashion to that described above in reference to FIGS. 8A and 8B.

FIG. 10 illustrates side and end views of a distal portion of a tissue treatment system including an expandable treatment element comprising a multiple lobed balloon, according to embodiments of the present inventive concepts. System 300 is constructed and arranged to treat target tissue, including one or more tissue portions as described above in reference to FIG. 3A. System 300 includes device 301 which includes a multi-lobed treatment element 320. Device 301 includes shaft 311 upon which treatment element 320 is mounted. Lobes 326 of treatment element 320 are fluidly connected to a lumen of shaft 311, lumen not shown but traveling proximally to an inflation port typically mounted to a handle of device 301. Shaft 311 may be configured to be slidingly passed through a separate device, such as an endoscope, after which treatment element 320 is expanded to engage the target tissue, such as the walls of a lumen. Shaft 311 may include a lumen 313, such as a guidewire lumen, which exits shaft 311 at distal end 312.

Treatment element 320 is shown in its radially expanded state, sized to engage the walls of a body lumen such as walls of the duodenum. Lobes 326 are constructed and arranged such that a separate device (e.g. an imaging or treatment device of system 300) can be passed between one or more of lobes 326 when treatment element 320 is positioned in a body lumen and expanded. Lobes 326 are typically filled with a fluid at an elevated temperature, such as saline at approximately 65° C. to 90° C., such that target tissue can be ablated or otherwise treated by treatment element 320. Temperature and duration of treatment may be selected such that tissue located between lobes 326 is also sufficiently treated. Alternatively, shaft 311 and lobes 326 may be rotated between successive energy applications in order to perform a 360° ablation. Successive deployments of treatment element 320 may be performed with treatment of target tissue at one or more locations. Prior to and/or during each tissue treatment, target tissue and/or tissue proximate target tissue may be manipulated, such as has been described hereabove. Alternatively or additionally, lobes 326 may include one or more electrodes, such as electrodes configured to deliver electromagnetic energy such as RF energy.

FIG. 11 illustrates a side view of a distal portion of a tissue treatment system including an expandable treatment element comprising a multi-electrode cage, according to embodiments of the present inventive concepts. System 300 is constructed and arranged to treat target tissue, including one or more tissue portions as described above in reference to FIG. 3A. System 100 comprises device 301 which includes a multi-electrode treatment element 320. Device 301 includes shaft 311 upon which treatment element 320 is operably mounted. Shaft 311 may be configured to be slidingly passed through a separate device, such as an endoscope, after which treatment element 320 is expanded to engage the target tissue, such as the walls of a lumen. Shaft 311 may include a lumen 313, such as a guidewire lumen, which exits shaft 311 at distal end 312.

Treatment element 320 includes cage 325, shown in its radially expanded state and sized to engage the walls of a body lumen such as walls of the duodenum. Cage 325 is operably attached to one or more deployment shafts or cables, not shown, but typically configured to deploy (i.e. radially expand) cage 325 when placed in tension through retraction, and to compact (i.e. undeploy) cage 325 when advanced. Cage 325 is constructed and arranged such that a separate device can be passed between one or more arms of cage 325 when treatment element 320 is positioned in a body lumen and expanded.

Electrodes 324 of treatment element 320 are mounted to cage 325 and are electrically connected to one or more wires, not shown but traveling proximally to an electrical connected typically mounted to a handle of device 301. An energy delivery unit, also not shown but of similar construction to EDU 330 of FIG. 5, is configured to deliver monopolar and/or bipolar energy to one or more of electrodes 324. Energy, typically RF energy, may be delivered to electrodes 324 such that target tissue can be ablated or otherwise treated by treatment element 320. Energy, temperature and/or duration of treatment may be selected such that tissue located between electrodes 324 is also sufficiently treated. Energy delivery to electrodes 324 may be configured to do a full circumferential tissue treatment after a single positioning step, with one or more energy deliveries. Alternatively, shaft 311 and electrodes 324 may be rotated between successive energy applications in order to perform a 360° ablation. Successive deployments of treatment element 320 may be performed with treatment of target tissue at one or more locations. Prior to and/or during each tissue treatment, target tissue and/or tissue proximate target tissue may be manipulated, such as has been described hereabove.

FIG. 12 illustrates a side view of a tissue treatment system including two tissue treatment elements, a balloon supported mesh abrader and a balloon configured for hot fluid containment, according to embodiments of the present inventive concepts. System 300 is constructed and arranged to treat target tissue, including one or more tissue portions as described above in reference to FIG. 3A. System 100 comprises device 301 which includes a first tissue treatment element 320 and second tissue treatment element 321. Device 301 includes shaft 311 upon which treatment elements 320 and 321 are operably mounted. Shaft 311 may be configured to be slidingly passed through a separate device, such as an endoscope, after which treatment elements 320 and 321 sequentially or simultaneously expanded to engage target tissue, such as the walls of a lumen. System 300 may include guidewire 371, and shaft 311 may include a lumen 313 configured to slidingly receive guidewire 371 for over-the-wire advancement of device 301 and/or other body-insertable devices of system 300 such as endoscope or second tissue treatment device.

Treatment element 320, shown in its radially expanded state, is sized to engage the walls of a body lumen such as walls of the duodenum. Treatment element 320 includes expandable element 327a (e.g. an expandable balloon), which is surrounded by an abrasive element 322a (e.g. a mesh abrader with the diamond pattern shown in FIG. 12). Abrasive element 322a may include a roughened surface and/or may be impregnated with abrasive material such as a grit or other abrasive material. Expandable element 327a is fluidly connected to a lumen within shaft 311, not shown but in fluid connection with inflation port 303 (e.g. a standard luer connector) mounted to handle 302. Inflation fluid such as air, $CO_2$, or saline can be introduced through shaft 311 to radially expand abrasive element 322a. Tissue treatment is accomplished by translating shaft 311 back and forth and/or rotating shaft 311 while abrasive element 322a is in contact with luminal wall tissue. The treatment may be adjusted by the radial force applied to expandable element 327a (i.e. the pressure within element 327a), the axial force applied to expandable element 327a, a rotational force applied to expandable element 327a, and combinations of these.

Treatment element 321, also shown in its radially expanded state, is sized to engage the walls of a body lumen such as walls of the duodenum. Treatment element 321 includes expandable element 327b (e.g. an expandable balloon), which is configured to be filled with hot fluid 322b (e.g. saline heated to a temperature of approximately 65° C. to 90° C.). Expandable element 327b is fluidly connected to a lumen within shaft 311, not shown but in fluid connection with inflation port 304 (e.g. a standard luer connector), such that heated saline can be introduced through shaft 311 to radially expand expandable element 327b and treat target tissue proximate hot fluid 322b. Tissue treatment is achieved by heat transfer from hot fluid 322b to tissue through expandable element 327b. In some embodiments, expandable element 327b may be moved relative to the target tissue during the tissue treatment, such as axial or rotational movement to deliver heat to a tissue surface area longer than expandable element 327b.

Successive deployments of treatment elements 320 and 321 may be performed with treatment of target tissue at one or more locations. Prior to and/or during each tissue treatment, target tissue and/or tissue proximate target tissue may be manipulated, such as has been described hereabove.

Figure 13A:
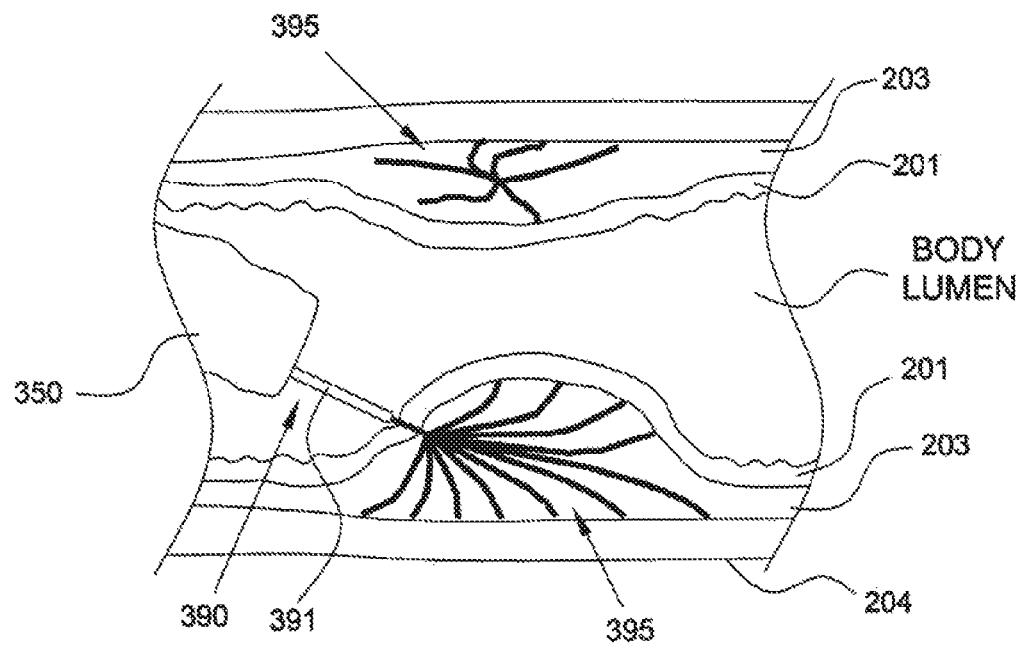
FIGS. 13A and 13B illustrates side sectional views of a target tissue expansion device, according to embodiments of the present inventive concepts.

FIG. 13A illustrates a side sectional view of a target tissue expansion device positioned within the gastrointestinal tract according to embodiments of the present inventive concepts. Endoscope 350 has been advanced to a location within a body lumen such as the duodenum. Fluid expansion device 390 has been inserted into and is shown exiting from endoscope 350. Expansion device 390 includes an elongate shaft 391 positioned proximate the duodenal mucosa 201. Fluid 395 is shown exiting a lumen of shaft 391. Shaft 391 and device 390 are configured to deliver fluid 395 in a waterjet fashion, such as through use of high pressure delivery through a nozzle, pressurization means and nozzle, not shown. Submucosal layer 203 has begun its expansion, circumferentially as shown in FIG. 13A. Expansion of submucosal layer 203 may be performed to increase the target area for treatment by one or more devices of the present inventive concepts, such as one or more devices described hereabove. The increased target area may be advantageous in preventing non-target tissue from being treated (e.g. ablated or abraded), such as by expanding a safety margin of target tissue.

Figure 13B:
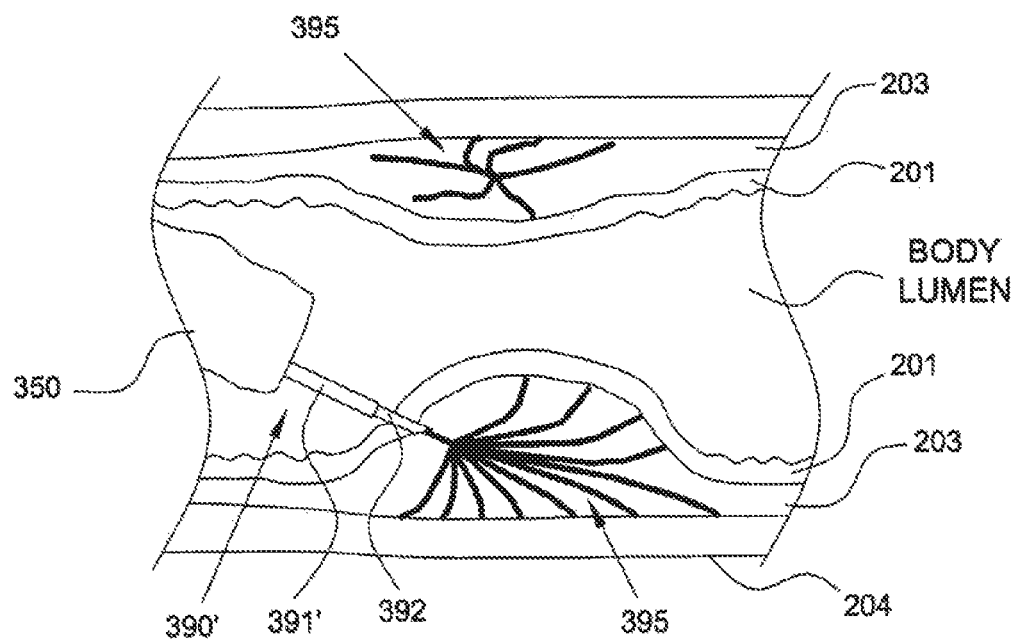

FIG. 13B illustrates a side sectional view of another target tissue expansion device positioned within the gastrointestinal tract, according to embodiments of the present inventive concepts. Device 390' of FIG. 13A has been inserted into and is shown exiting from endoscope 350. Device 390' is similar in form and function to device 390 of FIG. 13A other than shaft 391' includes an advanceable needle 392. Advanceable needle 392, instead of the water jet of FIG. 13A, is configured to penetrate into tissue such that fluid 395 can be delivered into and expand tissue.

Figure 14:
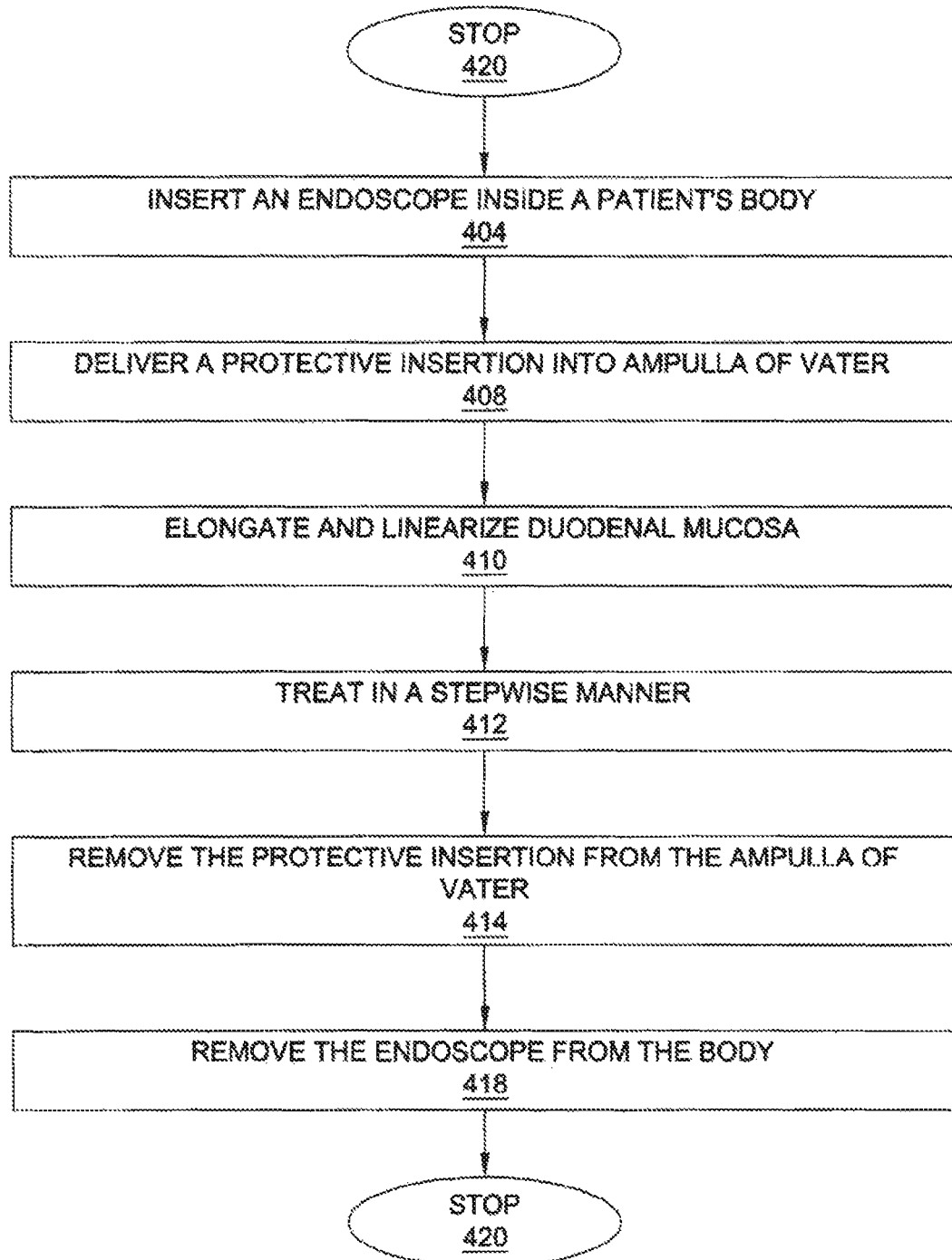
FIG. 14 illustrates a flow chart describing procedural steps for the treatment of diabetes, according to embodiments of the present inventive concepts.
Figure 15:
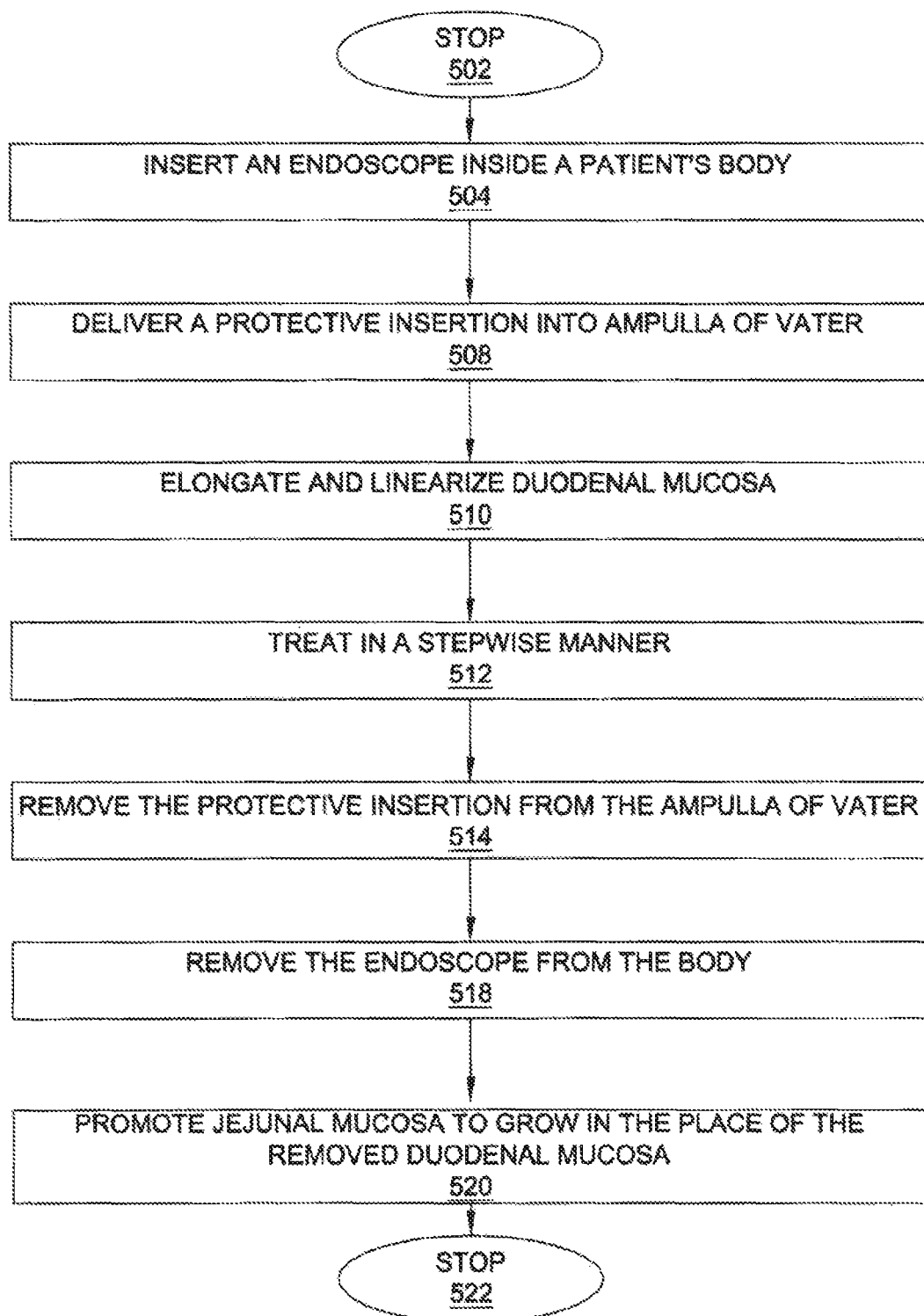
FIG. 15 illustrates a flow chart describing procedural steps for the treatment of diabetes, according to embodiments of the present inventive concepts.

FIGS. 14 thru 15 illustrate procedural steps 400 of embodiments of the inventive concepts where a target area of the duodenum is treated. Note that the step of determining the target area may be applicable to each embodiment discussed in connection with FIGS. 14-16. The procedure may start at step 402. At step 404, the endoscope 302 may be inserted inside a patient's body after a patient is under the effect of anesthesia such as general anesthesia or intravenous conscious sedation. The endoscope 302 may fit into the existing lumen of the scope over the guidewire. Thereafter, at step 408, a protective insertion may be delivered into the Ampulla of Vater 118. At step 410, the RF balloon 304 and the cutting balloon 308 may be used to elongate and linearize the duodenal mucosa. At step 412, any manner of therapy described above to treat, destroy, or remove tissue may be applied in a stepwise manner. At step 414, the protective insertion may be removed from the Ampulla of Vater 118. Finally, the endoscope 302 may be removed from the body at step 418. The procedure may finish at step 420. In accordance with an embodiment of the present inventive concepts, the procedure for the treatment of diabetes may also include monitoring the depth of treatment. In accordance with this embodiment, a placeholder may be provided with the endoscope 302. Monitoring the depth of ablation or scraping may be done with the use of the sensors that may be fitted along with the endoscope 302.

In accordance with certain embodiments of the present inventive concepts, relevant physiological parameters such as glucose, insulin, and the like in the ensuing days, weeks or months may also be monitored with the use of the sensors. The method described above may be utilized not only to treat diabetes, but also to improve diabetes symptoms, treat metabolic syndrome, improve glucose tolerance, reduce insulin-resistance in a patient, as well as reducing weight or obesity, and the like.

In some embodiments of the inventive concepts, the method described herein attempts and achieves altered hormonal signaling. Accordingly, the device used in accordance with an embodiment of the inventive concepts may be coupled with the monitoring of this hormonal signaling as a measure of efficacy. This may be accomplished by sampling the blood or lymphatic channels or endoluminal contents themselves for hormones released into the GI tract, or by some other manner.

Referring to FIG. 15, an embodiment of the present inventive concepts for the treatment of Type-2 diabetes is described. The procedure may start at step 502. At step 504, an endoscope 302 may be inserted inside a patient's body after a patient is under the effect of anesthesia such as general anesthesia or spinal anesthesia. Thereafter, at step 508, a protective insertion may be delivered into the Ampulla of Vater 118. At step 510, the RF balloon 304, and the cutting balloon 308 may be used to elongate and linearize the duodenal mucosa. At step 512, energy may be applied to the treatment areas causing treatment of the duodenal mucosa which can be, for example, in a stepwise manner. The treated duodenal mucosa may be shaved with the use of the cutting balloon 308 that may be equipped with a cutting device. The removal of the patient's duodenal mucosa may keep the rest of the patient's duodenum 114 anatomically intact. Further, elimination of stem cells may also be done to prevent re-growth. The process of applying energy and using mechanical device to abrade or cut the mucosa may include multiple treatments in series alternating between energy and abrading or it can include multiple energy steps with fewer abrading or multiple abrading steps with fewer energy steps. At step 514, the protective insertion may be removed from the Ampulla of Vater 118. Finally, the endoscope 302 may be removed from the body at step 518. At step 520, the patient's jejunal mucosa may be promoted to grow from the jejunal stem cells that are present in the place of the removed duodenal mucosa. Such promotion may be achieved by selecting a target area in accordance with pattern C on FIG. 3A.

The method described above may be utilized to treat diabetes as well as to improve diabetes symptoms, treat metabolic syndrome, improve glucose tolerance, reduce insulin-resistance in a patient, as well as reducing weight or obesity, and the like. The particulars of any treatment protocol for any of the above treatments can vary significantly and still be within the scope of this inventive concepts.

Figure 16:
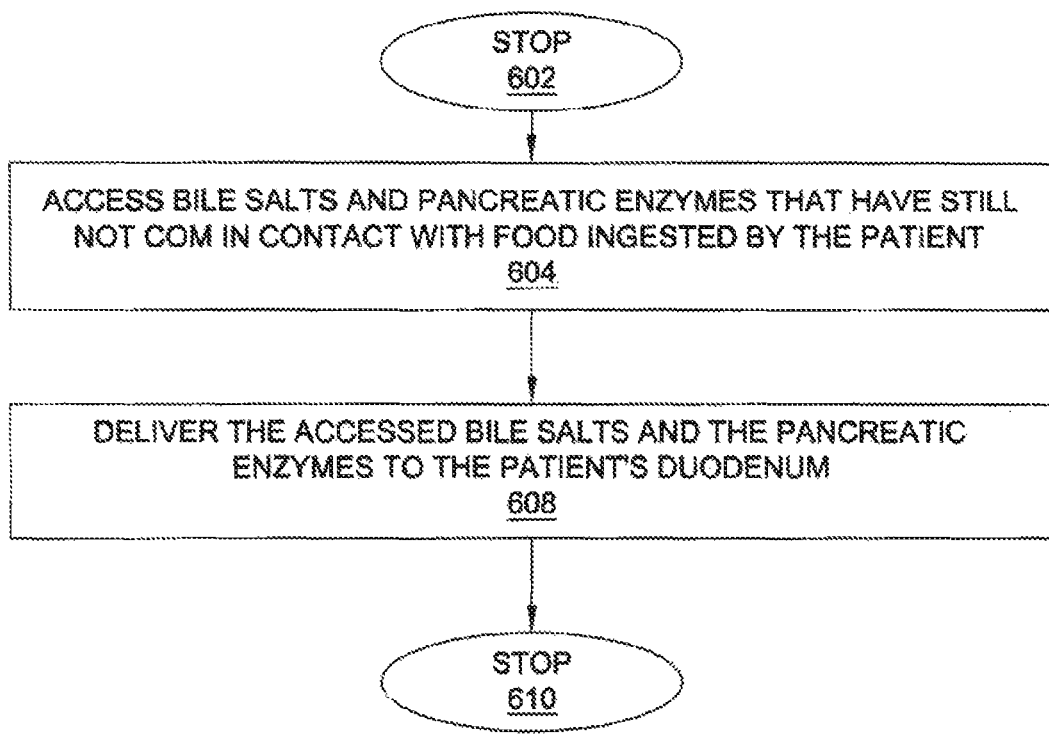
FIG. 16 illustrates a flow chart describing procedural steps for the treatment of diabetes, according to embodiments of the present inventive concepts.

Referring to FIG. 16, procedures of treatment of Type-2 diabetes are described, in accordance with another embodiment of the present inventive concepts. FIG. 16 illustrates a flow chart describing procedural steps 600 of the treatment of diabetes, in accordance with the third embodiment. The procedure may start at step 602. At step 604, a patient's bile salts and pancreatic enzymes that have still not come in contact with food ingested by the patient may be accessed. At step 608, the accessed bile salts and the pancreatic enzymes may be delivered to the patient's duodenum 114. The procedure may end at step 610. In accordance with this embodiment, the treatment may be based on direct routing of the unreacted (with the ingested food) bile salts and pancreatic enzymes to the duodenum 114 from the pancreatic ducts and bile ducts. The method described in this embodiment may be utilized not only to treat diabetes but also to improve diabetes symptoms, treat metabolic syndrome, improve glucose, reduce insulin-resistance in a patient, as well as reducing weight or obesity, and the like. Various modifications can be made to the procedure and still be within the scope of the inventive concepts.

Figure 17:
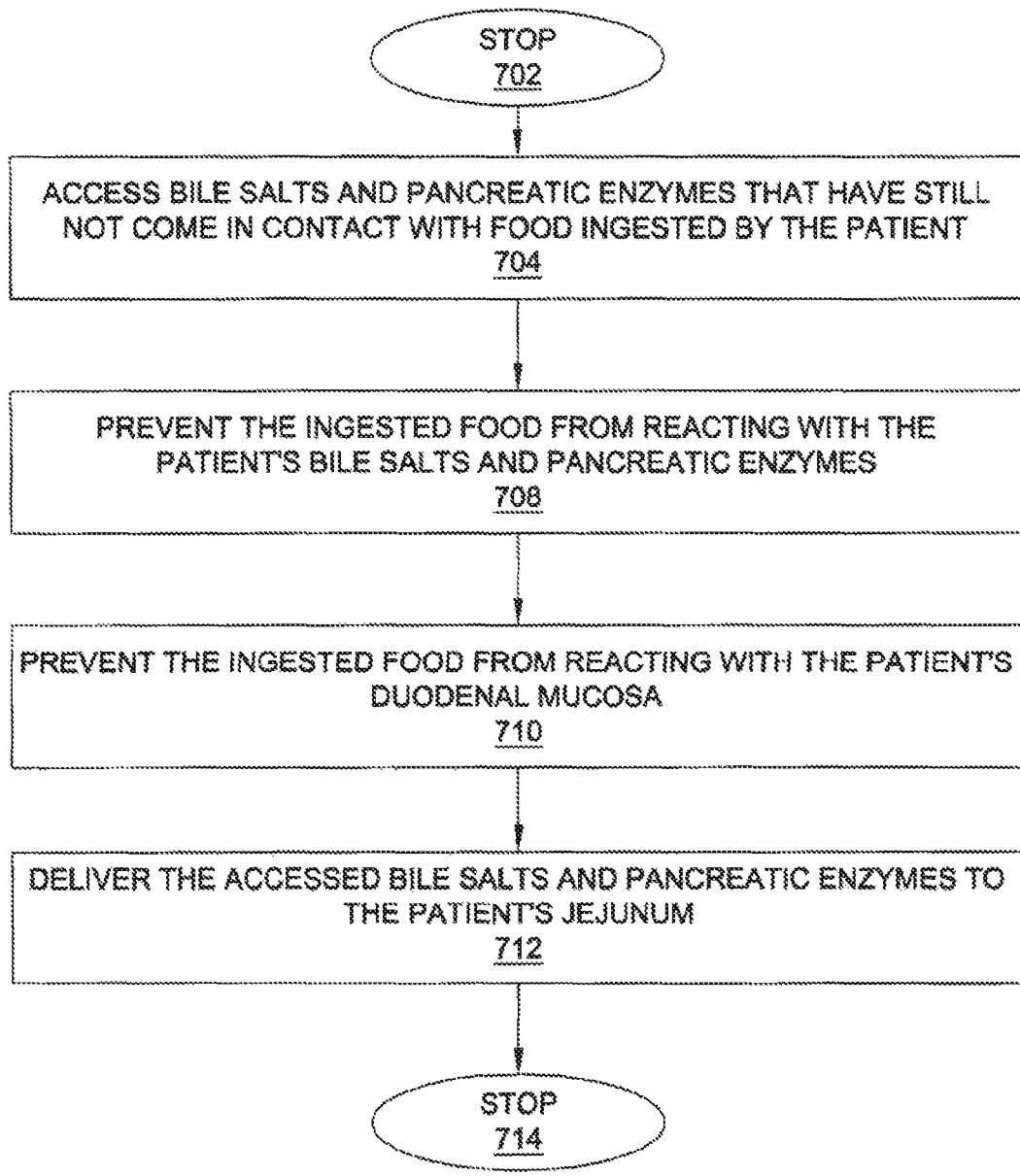
FIG. 17 illustrates a flow chart describing procedural steps for the treatment of diabetes, according to embodiments of the present inventive concepts.

Referring to FIG. 17, procedures of treatment of Type-2 diabetes are described, in accordance with still another embodiment of the present inventive concepts. FIG. 17 illustrates a flow chart describing procedural steps 700 of the treatment of diabetes, in accordance with the fourth embodiment. The procedure may start at step 702. At step 704, a patient's bile salts and pancreatic enzymes that have still not come in contact with food ingested by the patient may be accessed. At step 708, the ingested food may be prevented from reacting with the patient's bile salts and pancreatic enzymes. This may occur in a number of ways, for example, the energy treatments and mechanical treatments above. Additionally, other energy delivery or mechanical techniques to prevent the patient's bile salts and pancreatic enzymes may be used and still be within the scope of the inventive concepts. At step 710, the ingested food may be prevented from reacting with the patient's duodenal mucosa. This may occur using the energy delivery and mechanical treatments described above. Additionally, other energy delivery or mechanical techniques may be used and still be within the scope of the inventive concepts. At step 712, the accessed bile salts and pancreatic enzymes may be delivered to the patient's jejunum. The procedure may complete at step 714.

In accordance with this embodiment, the treatment may be based on direct routing of the unreacted bile salts and pancreatic enzymes (with the ingested food) to the jejunum from the pancreatic ducts and bile ducts. The method described in this embodiment may be utilized not only to treat diabetes but also to improve diabetes symptoms, treat metabolic syndrome, improve glucose tolerance, reduce insulin-resistance in a patient, as well as reducing weight or obesity, and the like. The treatment protocols for each of these treatments may be different and still be within the scope of the present inventive concepts.

The above-described procedures may provide alteration of the mucosa in the proximal small intestine itself, leaving an altered substrate that may consequently change the hormonal milieu in such a way as to ameliorate the diabetes. Further, the therapeutic, endoscopic approach may be utilized to alter gastrointestinal mucosa in order to alter hormonal balance for treating metabolically mediated conditions, such as diabetes. In addition, the therapeutic, endoscopic approach may facilitate altering of gastrointestinal mucosa to alter cholesterol transport and treat hypercholesterolemia. In accordance with various other embodiments, other conditions and factors may be treated by altering the duodenal mucosa. These conditions and factors may include energy expenditure; weight, appetite, insulin resistance; absorptive syndromes and disorders (celiac); and getting jejunum mucosa to grow back over.

The treatment of duodenal mucosa in accordance with the described procedures may allow growth of local proximal and/or distal mucosa that may have different and more beneficial hormonal characteristics in the management of diabetes. For example, treatment of distal jejunal tissue may be performed to allow ileum to grow proximally. As in another example, treatment of terminal ileum mucosa may be performed to replace it with more proximal ileal mucosa and/or colonic mucosa and therefore, prevent bile salts and cholesterol from being ingested. This may therefore serve as a treatment for hypercholesterolemia. In accordance with an embodiment, this may be achieved by the transplantation of mucosa/stem cells from one region of the intestinal lumen to another in order to encourage changes in the mucosal behavior due to the presence of different stem cells. The treatment procedure may also include explanation of mucosal tissue from distal ileum and transplant the cells to the treated duodenum to induce ileal mucosal growth more proximally in the small intestine since certain hormonal cells from the distal small intestine (L cells) are considered to release anti-diabetic hormones in response to a food bolus.

The mucosa may also be treated to a specific depth. For example, a top level may be removed and the lower level left as it is, e.g., partially damaged. This procedure may be done via ablation with RF, lasers, cryo such as microwave, and the like.

Because much of the hormonal signaling activity occurs at the level of duodenal bulb, the present treatment may preferably be performed in this region without causing any damage or inflammation/stricture to the Ampulla of Vater 118 or sphincter of Oddi 120 that deliver bile salts and pancreatic enzymes to the intestinal lumen. This may facilitate in improving diabetes and related syndromes, changing hormonal signals, protecting the sphincter of Oddi 120, preserving peristaltic functions, protecting pancreatic ducts, and the like.

The procedure described in conjunction with the above embodiments (FIGS. 14-17) may be followed by post-procedure care. The post-procedure care may involve monitoring for strictures and perforation, monitoring for malabsorption, nutrient and/or vitamin supplementation, and the like.

Embodiments of the present inventive concepts, as described above, may provide a method of treatment of Type-2 diabetes through a non-implant and non-surgical procedure. An advantage of the described embodiments of the present inventive concepts may be that the treatment through the endoscopic solution to diabetes may not leave an implant behind, may not ablate enough of the intestinal tract so as to cause malabsorption of nutrients, may not prevent entry of bile salts or pancreatic enzymes in the tract, and may not reroute food either through a device within the lumen or a device or region of human anatomy outside the traditional lumen to avoid interaction with the mucosal surface.

Embodiments of the present inventive concepts may improve glucose responsiveness and reduce insulin sensitivity. Further, the endocrine cells may release hormones that may enter the body from the duodenal mucosa and have effects such as affecting insulin resistance. In addition, different amounts of hormones may be released and cells may respond differently to stimulus than after the present treatment procedure is performed. The present inventive concepts may also enable blood glucose control and prevention of re-growth.

In order to alter the duodenal mucosa, one can use locally delivered drugs, such as (but not limited to) mitomycin C or a diluted acid. This can be combined with the procedure described herein in any number of ways (to prevent mucosal regrowth, to alter the local histology/architecture, to induce scarring, to prevent scarring, or to induce metaplasia). Many vehicles in which or with which these drugs can be applied or administered.

The therapies may also be coupled with oral medicines. These may include (but are not limited to) vitamin supplements, acid blocking drugs, mucosal healing agents, bile/pancreatic enzyme supplements, Mitomycin C, diluted acid, 5-FU, Cyclosporin (M-tor inhibitors), Sirolimus, FK506, a "-Limus" drugs, and anything used for drug-eluding stents. Toxins may also be injected into the submucosa (area between muscularized mucosa and epithelium). In addition, agents that cut off the mucosa from the blood flow or nutrients below it may be used. Sclerotherapy (injecting scarring agents into tissue) and altering mucosal re-growth may be used.

The present inventive concepts also contemplate that other techniques that may be combined with the ones described above. For example, polymer coatings could be applied to a treatment area after (or before) a particular treatment. When using a polymer coating, the cells may be treated, e.g., rendered inactive, and then coated. Additionally, a coating or sleeve may be painted on a treatment area. Again, this could occur after (or before) a particular treatment. Other treatments may include a scaffold and/or stent that could be used to cause a hypertropic reaction and/or encourage fibrosis. Additionally spray material, e.g., Nitinol, may be used to coat a treatment area. Further, a mucosal/epithelial graft may be used. In this embodiment, for example, a piece of jejunal or iliac tissue (or even esophageal tissue) is obtained, grown, and placed in the duodenum to create a new type of tissue in the duodenum. For example a graft of iliac tissue could be used to create a whole region of ileum in a treatment location of the duodenum.

In one embodiment, an ablation is undertaken and then a sleeve is implanted for a time period when the epithelium is growing back. This may be necessary in order to prevent improper wound healing or infection.

Figure 18:
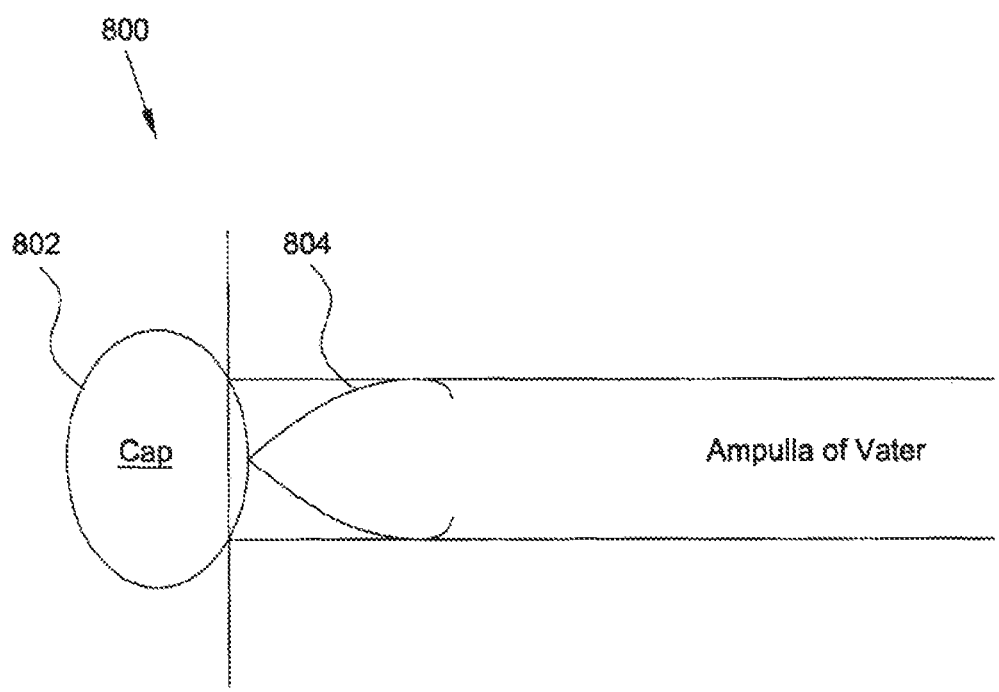
FIG. 18 illustrates a protective cap for the Ampulla of Vater, according to embodiments of the present inventive concepts.

In certain embodiments mentioned above, a protective cap 802 is used, as is illustrated in FIG. 18. This is a safety mechanism to protect a region, e.g., the Ampulla of Vater or Sphincter of Oddi. This technique includes inserting a wide-brimmed cap into a duct. There are many ways in which the cap can be inserted, held in place, and removed. For example, the cap 802 may be held in place with springs 804 that exert an outward pressure against the walls of the duct. After completion of the entire procedure, the cap can be removed with a snare and removed through the endoscope. When temporarily in place, it prevents bile salts from emptying into the duodenum. Sphincter of Oddi and ducts from bile and pancreatic enzymes enter the second portion of the duodenum. A sleeve, e.g., GI Dynamics device/sleeve, is installed just distal from that sphincter (so food mixes with pancreatic enzymes and the bile salts) before going into the sleeve. This limits the area of therapy to second portion of duodenum and beyond. Ablation may be done across the entire duodenum. Because no damage can occur to Sphincter of Oddi or the bile ducts, it is recommended to place a cap that would protect those elements from the effect of ablation. This may involve mechanically insulating, thermally insulating, electrically insulating, or rendering it optically opaque.

The systems and devices of the present inventive concepts include one or more treatment elements constructed and arranged to treat target tissue. A treatment element may be tissue contacting, such a hot or cold (e.g. cryogenic) fluid filled balloon or am expandable cage including one or more electrodes configured to deliver radiofrequency energy. The treatment elements may be expandable and/or they may be mounted to an expandable element. Expandable elements include but are not limited to: balloons; deployable cages; radially deployable arms; and combinations of these. The expandable elements may be configured to contact tissue, engage with tissue, and potentially to compress or otherwise exert a force upon tissue.

A treatment element or another component of a device or system of the present inventive concepts may include one or more coatings, such as a coating applied to a shaft, a balloon or an expandable cage. The coating may be configured to be released, such as throughout the procedure, or remain intact such as a lubricious coating configured to improve advancement or retraction of a device or component.

While the preferred embodiments of the devices and methods have been described in reference to the environment in which they were developed, they are merely illustrative of the principles of the inventive concepts. Modification or combinations of the above-described assemblies, other embodiments, configurations, and methods for carrying out the inventive concepts, and variations of aspects of the inventive concepts that are obvious to those of skill in the art are intended to be within the scope of the claims. In addition, where this application has listed the steps of a method or procedure in a specific order, it may be possible, or even expedient in certain circumstances, to change the order in which some steps are performed, and it is intended that the particular steps of the method or procedure claim set forth herebelow not be construed as being order-specific unless such order specificity is expressly stated in the claim.

What is claimed is:

1. A treatment system for treating diabetes in a patient, the system comprising:

a body access device having a viewing component constructed and arranged to access the patient's native duodenum and allow the duodenal mucosa to be evaluated, the viewing component comprising an imaging device mounted on the body access device, the imaging device configured to provide direct visualization of internal body spaces and tissue;

a controller constructed and arranged to select a target area of the patient's duodenal mucosa to treat;

a treating component constructed and arranged to treat a treatment area of the patient's native duodenal mucosa, such that the treatment leaves the patient's duodenum anatomically intact with respect to the patient's stomach and jejunum, the treating component comprising (a) a first treatment element positioned on a distal portion of a first elongate tube, said treatment element configured to treat mucosal tissue, wherein the treatment element comprises a balloon constructed and arranged to receive a hot fluid to circumferentially deliver energy to a wall of the patient's native duodenum for controlled depth ablation of the mucosal tissue, the controller constructed and arranged to provide the hot fluid to the balloon and to adjust the pressure within the balloon and (b) a second treatment element configured to treat mucosal tissue by abrasion or ablation positioned on a second elongate tube; and a tissue expansion device including a plurality of fluid injection needles configured to expand a full circumferential portion of submucosal tissue to increase a target treatment volume.

2. The system of claim 1, wherein the treating component is adapted to remove the patient's duodenal mucosa and the treatment comprises eliminating stem cells in the duodenal mucosa.

3. The system of claim 1, wherein the balloon comprises an ablative subcomponent for ablating the duodenal mucosa.

4. The system of claim 1, wherein the treating component further comprises a shaver and/or scraper for shaving at least a portion of the duodenal mucosa.

5. The system of claim 1, wherein the treatment element is constructed and arranged to treat one or more of: Diabetes; Type-1 Diabetes; Type-2 Diabetes; hypercholesterolemia; a metabolic syndrome; disease; celiac disease; obesity; cancer such as bronchoalveolar carcinoma; and cystitis.

6. The system of claim 1, wherein the first elongate tube has a lumen configured to deliver the hot fluid to the balloon.

7. The system of claim 1, wherein the treatment element is constructed and arranged to radially expand and/or radially extend to a diameter of at least 1 cm.

8. The system of claim 1, wherein the controller is constructed and arranged to deliver the hot fluid to the balloon at a temperature of approximately 65° C. to 90° C.

9. The system of claim 1, wherein the treatment element is constructed and arranged for closed loop energy delivery.

10. The system of claim 1, further comprising a sensor, wherein the system is constructed and arranged to deliver energy based on signals recorded by the sensor.

* * * * *